US011098052B2

(12) United States Patent
Pettit et al.

(10) Patent No.: US 11,098,052 B2
(45) Date of Patent: Aug. 24, 2021

(54) 4-AZAPODOPHYLOTOXINS COMPOUNDS

(71) Applicant: George Robert Pettit, Paradise Valley, AZ (US)

(72) Inventors: George Robert Pettit, Paradise Valley, AZ (US); Justin Searcy, Loveland, CO (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/081,683

(22) PCT Filed: Mar. 2, 2017

(86) PCT No.: PCT/US2017/020488
§ 371 (c)(1),
(2) Date: Aug. 31, 2018

(87) PCT Pub. No.: WO2017/151947
PCT Pub. Date: Sep. 8, 2017

(65) Prior Publication Data
US 2019/0077808 A1    Mar. 14, 2019

Related U.S. Application Data

(60) Provisional application No. 62/302,236, filed on Mar. 2, 2016.

(51) Int. Cl.
*C07D 491/048* (2006.01)
*C07D 491/14* (2006.01)
*C07D 491/153* (2006.01)
*A61P 35/00* (2006.01)

(52) U.S. Cl.
CPC .......... *C07D 491/048* (2013.01); *A61P 35/00* (2018.01); *C07D 491/14* (2013.01); *C07D 491/153* (2013.01)

(58) Field of Classification Search
CPC .... C07D 491/048; C07D 491/14; A61P 35/00
USPC .......................................................... 546/65
See application file for complete search history.

(56) References Cited

U.S. PATENT DOCUMENTS

| 6,214,345 | B1 | 4/2001 | Firestone et al. | |
|---|---|---|---|---|
| 6,548,515 | B1* | 4/2003 | Husson | A61P 35/00 514/284 |
| 7,745,394 | B2 | 6/2010 | Doronina et al. | |
| 2004/0198981 | A1 | 10/2004 | Husson et al. | |
| 2008/0113994 | A1* | 5/2008 | Velten | A01N 43/90 514/252.04 |
| 2015/0017188 | A1 | 1/2015 | Eigenbrot, Jr. et al. | |

FOREIGN PATENT DOCUMENTS

| EP | 1103554 A1 * | 5/2001 | ............. A61P 35/00 |
|---|---|---|---|
| WO | WO 1997/09984 | 3/1997 | |
| WO | WO-2005097802 A1 * | 10/2005 | ............. A01N 43/90 |

OTHER PUBLICATIONS

Atsuo Babs et al Studies on disease-modifying antirheumatic Drugs. . . (Year: 1999).*
Yukio Hitotsuyanagi et al , A facile Synthesis of the 4-Aza-analogs of 1-arylnaphthalene Lignans Chinensis, Justicidin B, and Taiwanin C (Year: 1997).*
Yukio Hitotsuyanagi et al 4-Aza-2,3-dehydro-4-deoxypodophyllotoxins: Simple Aza-podophyllotoxin Analogues Possessing Potent Cytotoxicity. (Year: 2000).*
Ajay Kumar et al (Year: 2010).*
Mirko Andreoli et al , Identification of the first Inhibitor of the GBP1:PIM1 interaction. (Year: 2014).*
English abstract, Caplus of EP 1103554 (Year: 2001).*
George Pettit et al. Journal of Natural Products , Antineoplastic Agents, 585. Isolation of Bridelia ferruginea Anticancer Podophyllotoxins and Synthesis of 4-Aza-podophyllotoxin Structural Modifications, (Year: 2016).*
Zhang, Z. W.; Zhang, J. Q.; Hui, J.-Q.; Chen, L. H.; Chen, S.-W.; Tian, X. Eur. J. Med. Chem. 2010, 45, 1673-1677.
Addae-Mensah, I.; Achenbach, H. Phytochemistry 1985, 24, 1817-1819.
Addae-Mensah, I.; Munenge, R. W. Fitoterapia 1989, 60, 359-362.
Beletskaya, I. P.; Cheprakov, A. V. Coord. Chem. Rev. 2004, 248, 2337-2364.
Botes, M. G.; Pelly, S. C.; Blackie, M. A. L.; Kornienko, A.; van Otterlo, W. A. L. Chem. Heterocycl. Compd. 2014,50, 119-137.
Broomhead, A. J.; Dewick, P. M. Phytochemistry 1990, 29, 3831-3837.
Castro, A. M.; del Corral, J. M. M.; Garcia, P.A.; Rojo, M. V.; de la Iglesia-Vicente, J.; Mollinedo, F.; Cuevas, C.; San Feliciano, A. J. Med. Chem. 2010, 53, 983-993.
Chang, L. C.; Song, L. L.; Park, E. J.; Luyengi, L.; Lee, K. J.; Farnsworth, N. R.; Pezzuto, J. M.; Kinghorn, A. D. J. Nat. Prod. 2000, 63, 1235-1238.
Che, Z.; Yu, X.; Zhi, X.; Fan, L.; Yao, X.; Xu, H. J. Agric. Food. Chem. 2013, 61,8148-8155.
Cimanga, K.; Ying, L.; De Bruyne, T.; Apers, S.; Cos, P.; Hermans, N.; Bakana, P.; Tona, L.; Kambu, K.; Kalenda, D. T.; Pieters, L.; Vanden Berghe, D.; Vlietinck, A. J. J. Pharm. Pharmacol. 2001,53, 757-761.
Dong, W.; Zhang, L.; Niu, Y.; Fan, D.; Wu, X.; Tang, X.; Cai, C. Expert Opin. Drug. Deliv. 2013, 10, 559-571.
Dossena, A.; Marchelli, R.; Pochini, A. J. Chem. Soc., Chem. Commun. 1974, 771-772.
Eyberger, A. L.; Dondapati, R.; Porter, J. R. J. Nat. Prod. 2006, 69, 1121-1124.
Giorgi-Renault, S. Ann. Pharm. Fr. 2005, 63, 63-68.
Hanauske, A. R.; Wuester, K. C.; Lehmer, A.; Rotter, M.; Schneider, P.; Kaeser-Froelich, A.; Rastetter, J.; Depenbrock, H. Eur. J. Cancer, Part A 1995, 31 A, 1677-1681.

(Continued)

*Primary Examiner* — Rita J Desai
(74) *Attorney, Agent, or Firm* — Byrne Poh LLP; Nina R. Horan

(57) ABSTRACT

The present disclosure relates to 4-azapodophylotoxins compounds, pharmaceutical compositions comprising such compounds, kits, and methods for using such compounds or pharmaceutical compositions.

4 Claims, No Drawings

(56) References Cited

OTHER PUBLICATIONS

Hartwell, J. L.; Schrecker, A. W. In Fortschritte der Chemie organischer Naturstoffe, vol. XV; Zechmeister, L., Ed.; Springer-Verlag: Vienna, 1958, 83.
Hearon, W. M.; MacGregor, W. S. Chem. Rev. 1955, 55, 957-1068.
Hitotsuyanagi, Y.; Fukuyo, M.; Tsuda, K.; Kobayashi, M.; Ozeki, A.; Itokawa, H.; Takeya, K. Bioorg. Med. Chem. Lett. 2000, 10, 315-317.
Ikeda, R.; Nagao, T.; Okabe, H.; Nakano, Y.; Matsunaga, H.; Katano, M.; Mori, M. Chem. Pharm. Bull. 1998, 46,871-874.
International Search Report and Written Opinion dated Jul. 14, 2017 in International Patent Application No. PCT/US2017/020488.
Iwu, M. M.; Court, W. E. Planta Med. 1980, 38, 260-263.
Jin, Y.; Liu, J.; Huang, W.-T.; Chen, S. W.; Hui, L. Eur. J. Med. Chem. 2011, 46, 4056-4061.
Kamal, A.; Mallareddy, A.; Suresh, P.; Nayak, L.; Shetti, R. V. C. R. N. C.; Rao, N. S.; Tamboli, J. R.; Shaik, T. B.; Vishnuvardhan, M. V. P. S.; Ramakrishna, S. Eur. J. Med. Chem. 2012, 47, 530-545.
Kamal, A.; Suresh, P.; Ramaiah, M. J.; Mallarddy, A.; Kumar, B. A.; Raju, P.; Gopal, J. V.; Pushpavalli, S. N. C. V. L.; Lavanya, A.; Sarma, P. Bioorg. Med. Chem. 2011,19, 4589-4600.
Kumar, A.; Alegria, A. E. J. Heterocycl. Chem. 2010, 47, 1275-1282.
Labruere, R.; Hautier, B.; Testud, M.; Seguin, J.; Lenoir, C.; Desbene-Finck, S.; Helissey, P.; Garbay, C.; Chabot, G. G.; Vidal, M.; Giorgi-Renault, S. Chern. Med. Chem., 2010, 5, 2016-2025.
Lee, C. C.; Huang, T. S. Pharm. Res. 2001,18, 846-851.
Ley, S. V.; Thomas, A. W. Angew. Chem. Intl. Ed. 2003, 42, 5400-5449.
Li, W.-Q.; Wang, X.-L.; Qian, K.; Liu, Y.-Q.; Wang, C.-Y.; Yang, L.; Tian. J.; Morris-Natschke, S. L.; Zhou, X.-W.; Lee, K.-H. Biorg. Med. Chem. 2013, 21, 2363-2369.
Marchelli, R.; Dossena, A.; Pochini, A.; Dradi, E. J. Chem. Soc., Perkin Trans. 1 1977, 713-717.
Mider, G. B. J. Nat. Cancer Inst. 1957, 19, 191-223.
Monks, A.; Scudiero, D.; Skehan, P.; Shoemaker, R.; Paull, K.; Vistica, D.; Hose, C.; Langley, J.; Cronise, P.; Viagro-Wolff, A.; Gray-Goodrich, M.; Campbell, H.; Mayo, J.; Boyd, M. J. Natl. Cancer Inst. 1991, 83, 757-766.
Passarella, D.; Peretto, B.; Yepes, R. B.; Cappellettit, G.; Cartelli, D.; Ronchi, C.; Snaith, J.; Fontana, G.; Danieli, B.; Borlak, J. Eur. J. Med. Chem. 2010, 45, 219-226.
Pettit, G. R. J. Nat. Prod. 1995, 58, 359-364.
Pettit, G. R.; Alkalay, D. S. J. Org. Chem. 1960, 25, 1363-1365.
Pettit, G. R.; Baumann, M. F.; Rangammal, K. N. J. Med. Pharm. Chem. 1962, 5, 800-808.
Pettit, G.R et al.; Journal of Natural Products, 2016, 507-518.
Pinney, K. G.; Jelinek, C.; Edvardsen, K.; Chaplin, D. J.; Pettit, G. R. In Anticancer Agents from Natural Products; Cragg, G. M.; Kingston, D. G. I.; Newman, D. J.; Eds.; Taylor and Francis: Boca Raton, FL, 2005; pp. 23-46.
Rashid, M. A.; Gustafson, K. R.; Cardellina, J. H., II; Boyd, M. R. Nat. Prod. Lett. 2000, 14, 285-292.
Salerno, S.; Da Settuni, F.; Taliani, S.; Sunirubu, F.; La Motta, C.; Fornaciari, G.; Marini, A. M. Curr. Med. Chem. 2010, 17, 4270-4290.
Seliger, H. Der Krebsarzt 1955, 10, 357-360.
Singh, P.; Faridi, U.; Srivastava, S.; Kumar, J. K.; Darokar, M.P.; Luqman, S; Shanker, K.; Chanotiya, C. S.; Gupta, A.; Gupta, M.M.; Negi, A.N. Chem. Pharm. Bull. 2010, 58, 242-246.
Snyder, H. R.; Konecky, M. S.; Lennarz, W. J. J. Am. Chem. Soc. 1958, 80, 3611-3615.
Tratrat, C.; Georgi-Renault, S.; Husson, H.-P. Org. Lett. 2002, 4, 3187-3189.
Utsugi, T.; Shibata, H.; Kumio, S.; Aoyagi, K.; Wierzba, K.; Kobunai, T.; Terada, T.; Oh-hara, T.; Tsuruo, T.; Yamada, Y. Cancer Res. 1996, 56, 2809-2814.
Wang, C.; Wu, Z.; Zhao, Y.; Ni, C.; Zhao, X.; Zhu, L. Arch. Pharm. Chem. Life Sci. 2011, 344, 735-740.
Wang, J. Z.; Tian, X.; Tsumura, H.; Shimura, K.; Ito, H. Anticancer Drug Des. 1993, 8, 193-202.
Wilstermann, A. M.; Bender, R. P.; Godfrey, M.; Choi, S.; Anklin, C.; Berkowitz, D. B.; Osheroff, N.; Graves, D. E. Biochemistry 2007, 46, 8217-8225.
Wu, Y.; Zhao, J.; Chen, J.; Pan, C.; Li, L.; Zhang, H. Org. Lett. 2009, 11, 597-600. (b) Wu, Y.; Zhang, H.; Zhao, Y.; Zhao, J.; Chen, J.; Li, L. Org. Lett. 2007, 9, 1199-1202.
Xu, H.; He, X. Q.; Bioorg. Med. Chem. Lett. 2010, 20, 4503-4506.
Yong, Y.; Shin, S. Y.; Lee, Y. H.; Lim, Y. Bioorg. Med. Chem. Lett. 2009, 19, 4367-4371.
Zhang, Y.-J.; Litaudon, M.; Bousserouel, H.; Martin, M.-T.; Thoison, O.; Léonce, S.; Dumontet, V.; Sévenet, T.; Guéritte, F. J. Nat. Prod. 2007, 70, 1368-1370.
Zhang, Z.-J.; Tian, J.; Wang, L.-T.; Wang, M.-J.; Nan, X.; Yang, L.; Liu, Y-Q.; Morris-Natschke, S. L.; Lee, K.-H.; Biorg. Med. Chem. 2014, 22, 204-210.
Zhi, X.; Yu, X.; Yang, C.; Ding, G.; Chen, H.; Xu, H. Bioorg. Med. Chem. Lett., 2014, 24, 765-722.

* cited by examiner

4-AZAPODOPHYLOTOXINS COMPOUNDS

FEDERALLY SPONSORED RESEARCH OR DEVELOPMENT

This invention was made with government support under R01 CA090441 awarded by the National Institutes of Health. The government has certain rights in the invention.

BACKGROUND

The African sub-tropical medicinal plant *Bridelia ferruginea* Benth. (family Euphorbiaceae) has found use in African traditional medicine for the treatment of diarrhea, dysentery, female sterility, and rheumatic pains. The genus contains some 60 species. One of the early biological studies of this plant showed that crude extracts lowered the fasting blood sugar levels of rats and humans.[2] Later, more extensive studies reported in 1985[3] involving the chemical composition confirmed the presence of several already known terpenoids and flavonoids. This was followed by the discovery of compounds thought to be responsible for the medicinal effects of this plant such as xanthine oxidase inhibition, related to liver disorders, and superoxide-scavenging activity of phenolic compounds possibly related to the rheumatic pain relief[4] associated with the traditional use of *B. ferruginea*. The glucoside flavonoid rutin[5] was also discovered in 1989 and thought to be the source of the hypoglycemic effects.

As a continuation of long-term research directed at discovery and development of new natural products with anticancer and other biological activities, one of the co-inventors undertook an evaluation of the *B. ferruginea* cancer cell growth inhibitory constituents. Initial investigations were limited to only 3.24 g of a dichloromethane-methanol extract but later augmented by a 34.5 kg recollection of the dry plant. Crude extracts of *B. ferruginea* displayed quite significant in vitro cancer cytostatic activity ($ED_{50}$ 0.02 µg/mL) in the P388 murine lymphocytic leukemia cell line. Those results prompted an extensive P388 cell line bioassay-guided fractionation which afforded four substantially active cancer cell growth inhibitors, but proved to be all previously known compounds, namely, deoxypodophyllotoxin (1), β-peltatin-5-O-β-D-glucopyranoside (3a), and the indole neoechinulin (4).

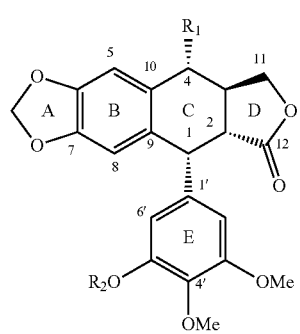

1, $R_1$ = H, $R_2$ = Me, Deoxypodophyllotoxin
1a, $R_1$ = OH, $R_2$ = Me, Podophyllotoxin

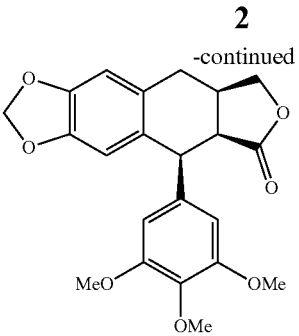

2, Isopicrodeoxypodophyllotoxin

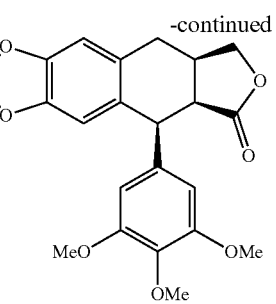

3, $R_1$ = H, β-Peltatin
3a, $R_1$ = 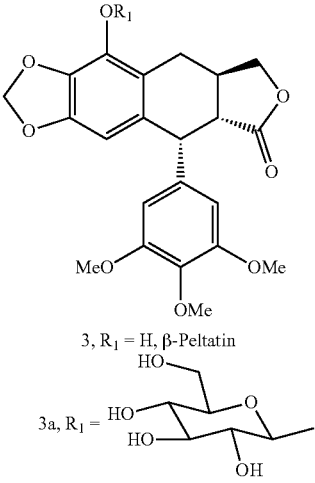 β-Peltatin-5-O-β-D-glucopyranoside

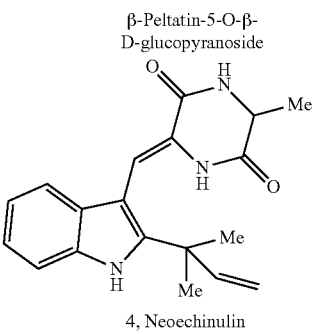

4, Neoechinulin

While Boyd and colleagues[6] had already expertly reported the bioassay-guided fractionation of *B. ferruginea* extracts, the initial sample collections were limited to a relatively small (10-480 g)[6] amount of plant material. On the assumption that a large-scale collection would lead to the isolation of active constituents occurring at very low concentrations in this plant, we proceeded as summarized above with a recollection of the dry plant. Although no new cancer cell growth inhibitors were found, the scale-up approach did provide isopicrodeoxypodophyllotoxin (2), which is a new constituent of *B. ferruginea*. The scale up results were largely consistent with those reported by the Boyd group[6] in 2000, who summarized the isolation and characterization of deoxypodophyllotoxin (1), β-peltatin (3), β-peltatin-5-O-β-D-glucopyranoside (3a), and 5'-demethoxy-β-peltatin-5-O-β-D-glucopyranoside.

By about 1955, the early research of Dr. Jonathan L. Hartwell at the NCI had led to preclinical development of podophyllotoxin (1a) from the dried roots and rhizomes of certain *Podophyllum* species, especially the "Mayapple" (*Podophyllum peltatum*) used by the Penobscot native Americans of Maine.[13-15] These pioneering advances led to the present well-known anticancer drugs and lead compounds ranging from etoposide (5) to tenoposide (6), 7, 8, 9 and GL-331 (10).[16] Indeed, until the development of taxol (paclitaxel), etoposide, on a worldwide basis, was the most widely prescribed anticancer drug. High-dose etoposide remains a useful drug in combination with other small-molecule anticancer drugs for the treatment of refractory Hodgkin's lymphoma, non-Hodgkin's lymphoma, acute leukemia, and other refractory hematological-type cancers.[17]

The need for producing podophyllotoxin (1a)-derived anticancer drugs has stimulated the exploration of other higher plant sources,[18] a number of total synthetic approaches including a recent 12-step route (29% overall)[19a,b] and a microbiological approach utilizing two endophyte fungi from rhizomes of *P. peltatum* that, interestingly, provided podophyllotoxin (1a), albeit in low yield.[16] In parallel, a large number of attempts at successful (simple) structural modifications of 1a have been ongoing over the past nearly 55 years where some of the most recent appear in Ref 20 directed at anticancer,[20a-i] anti-insect,[20j-l] antiparisitic,[20k] DNA damaging,[20l-o] and vascular disrupting[20p] targets. Two of the earliest arose when one of the co-inventors began to modify the 1a aromatic system beginning in 1958.[21]

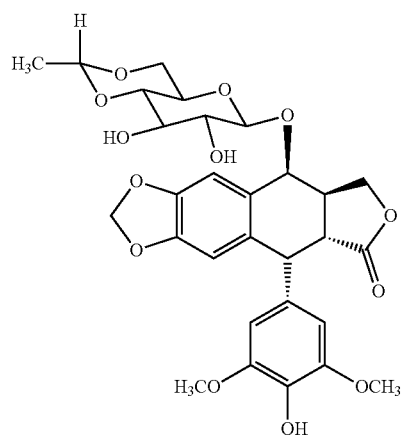

5, Etoposide

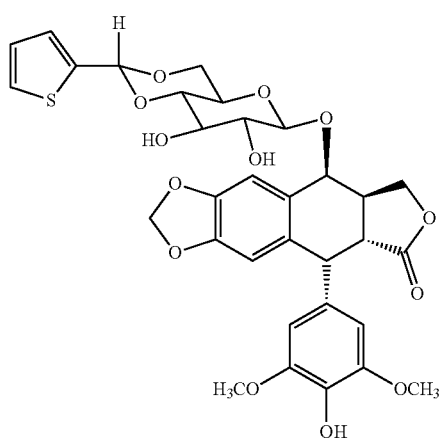

6, Tenoposide

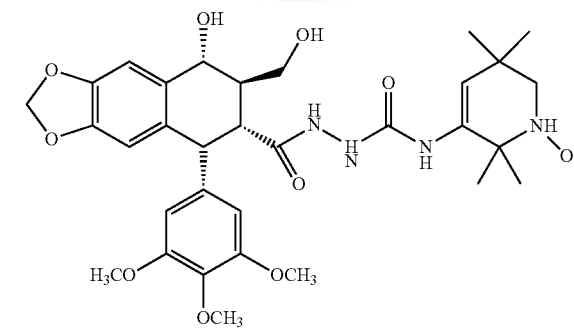

7, GP-11

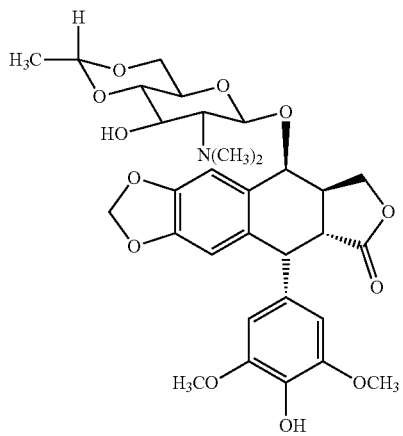

8, NK-611

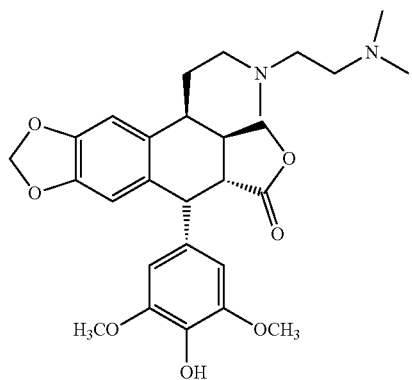

9, TOP-53

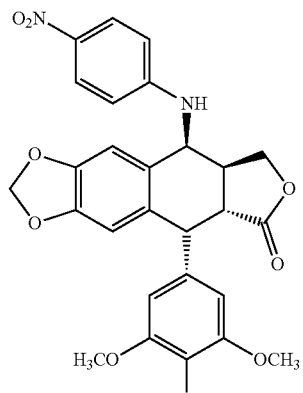

10, GL-331

Accordingly, there is a need to provide new podophyllotoxin compounds that have suitable cancer cell growth inhibition values and that contain an easily derivatizable group for conjugation to monoclonal antibodies.

Citation of any reference in this section is not to be construed as an admission that such reference is prior art to the present disclosure.

SUMMARY

The present disclosure relates to 4-azapodophylotoxins, pharmaceutical compositions comprising such compounds, kits, and methods for using such compounds or pharmaceutical compositions. The compounds of the present disclosure contain an easily derivatizable group for conjugation to monoclonal antibodies. The compounds have, or are believed to have, suitable cancer cell growth inhibition values.

In a first embodiment, the present disclosure provides a compound of formula (I):

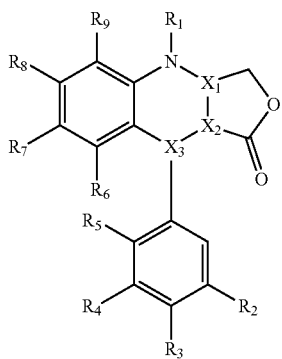

(I)

or a pharmaceutically acceptable salt thereof, wherein $R_1$ is selected from H, $(C_1-C_6)$alkyl, $(C_3-C_7)$cycloalkyl, a lone pair of electrons when N and $X_1$ form a double bond, or a Linker Unit;

wherein the alkyl is unsubstituted or substituted with a substituent selected from $OR_{10}$, $NR_{10}R_{11}$, (5- or 6-membered)heterocyclic ring comprising one or two heteroatoms selected from N, O and S, $(C_3-C_7)$cycloalkyl, $(C_6-C_{14})$aryl, (5- or 6-membered)heteroaryl comprising one, two or three heteroatoms selected from N, O and S, or a Linker Unit;

where $R_{10}$ and $R_{11}$ are independently H, $(C_1-C_6)$alkyl, a Protecting Group, or a Linker Unit;

wherein the aryl is unsubstituted or substituted with one to three substitutents selected from halo, nitro, cyano, $(C_1-C_6)$alkoxy, $NR_{10}R_{11}$, $(C=O)(C_1-C_6)$alkyl, $CO_2R_{10}$, $CONR_{10}R_{11}$, or a Linker Unit;

$R_2$, $R_3$ and $R_4$ are independently selected from H, $(C_1-C_6)$alkoxy, halo, $OR_{10}$, or $NR_{10}R_{11}$;

$R_5$ is H;

or $R_4$ and $R_5$ are taken together with the carbons to which they are attached to form a 1,3-dioxolo ring;

$R_6$ is selected from H or $(C_1-C_6)$alkoxy;

$R_7$ is $(C_1-C_6)$alkoxy;

$R_8$ is $(C_1-C_6)$alkoxy;

or $R_7$ and $R_8$ are taken together with the carbons to which they are attached to form a 1,3-dioxolo ring;

$R_9$ is H;

$X_1$, $X_2$ and $X_3$ are carbon and either (a) $X_1$ and N form a double bond and $X_2$ and $X_3$ form a double bond; or (b) $X_1$ and $X_2$ form a double bond.

In a second embodiment, the present disclosure provides a compound of formula (Ia):

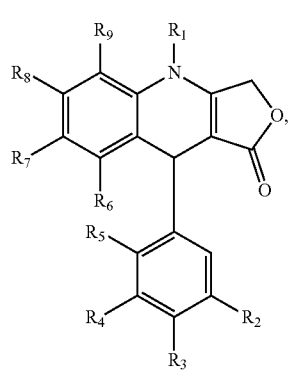

(Ia)

wherein $R_1$, $R_2$, $R_3$, $R_4$, $R_5$, $R_6$, $R_7$, $R_8$ and $R_9$ are as defined above in connection with a compound of formula (I).

In a third embodiment, the present disclosure provides a compound of formula (Ib):

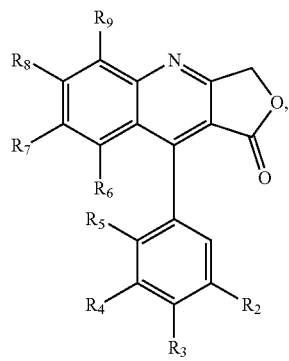

(Ib)

wherein $R_1$, $R_2$, $R_3$, $R_4$, $R_5$, $R_6$, $R_7$, $R_8$ and $R_9$ are as defined above in connection with a compound of formula (I).

DETAILED DESCRIPTION

In one or more embodiments, the compound includes the following:

(1.) A compound of formula (I),

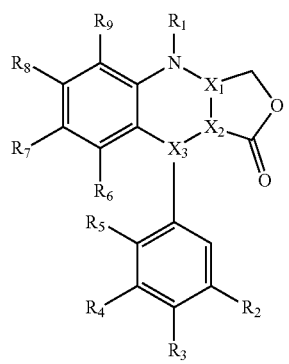

(I)

or a pharmaceutically acceptable salt thereof, wherein $R_1$ is selected from H, $(C_1-C_6)$alkyl, $(C_3-C_7)$cycloalkyl, a lone pair of electrons when N and $X_1$ form a double bond, or a Linker Unit;

wherein the alkyl is unsubstituted or substituted with a substituent selected from $OR_{10}$, $NR_{10}R_{11}$, (5- or 6-membered)heterocyclic ring comprising one or two heteroatoms selected from N, O and S, $(C_3-C_7)$cycloalkyl, $(C_6-C_{14})$aryl, (5- or 6-membered)heteroaryl comprising one, two or three heteroatoms selected from N, O and S, or a Linker Unit;

where $R_{10}$ and $R_{11}$ are independently H, $(C_1-C_6)$alkyl, a Protecting Group, or a Linker Unit;

wherein the aryl is unsubstituted or substituted with one to three substitutents selected from halo, nitro, cyano, $(C_1-C_6)$alkoxy, $NR_{10}R11$, $(C=O)(C_1-C_6)$alkyl, $CO_2R_{10}$, $CONR_{10}R_{11}$, or a Linker Unit;

$R_2$, $R_3$ and $R_4$ are independently selected from H, $(C_1-C_6)$alkoxy, halo, $OR_{10}$, or $NR_{10}R_{11}$;

$R_5$ is H;

or $R_4$ and $R_5$ are taken together with the carbons to which they are attached to form a 1,3-dioxolo ring;

$R_6$ is selected from H or $(C_1-C_6)$alkoxy;

$R_7$ is $(C_1-C_6)$alkoxy;

$R_8$ is $(C_1-C_6)$alkoxy;

or $R_7$ and $R_8$ are taken together with the carbons to which they are attached to form a 1,3-dioxolo ring;

$R_9$ is H;

$X_1$, $X_2$ and $X_3$ are carbon and either (a) $X_1$ and N form a double bond and $X_2$ and $X_3$ form a double bond;

or (b) $X_1$ and $X_2$ form a double bond.

(2.) The compound of the above (1.), wherein $R_2$ is selected from H or $(C_1-C_6)$alkoxy;

$R_3$ is selected from H, $(C_1-C_6)$alkoxy, hydroxyl, O-Protecting Group, or O-Linker Unit;

$R_4$ is selected from $(C_1-C_6)$alkoxy, halo, hydroxyl, O-Protecting Group, or O-Linker Unit.

(3.) The compound of the above (1.) or the above (2.), wherein the compound has formula (Ia)

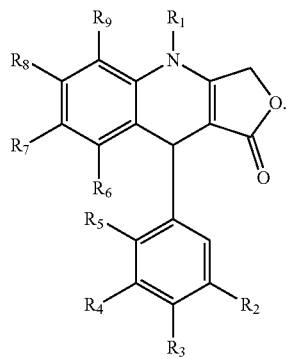

(4.) The compound of any one of the above (1.) to (3.), wherein $R_1$ is selected from H, $(C_1-C_3)$alkyl, $(C_4-C_6)$cycloalkyl, a lone pair of electrons when N and $X_1$ form a double bond, or Linker Unit;

wherein the alkyl is unsubstituted or substituted with a substituent selected from $OR_{10}$, $NR_{10}R_{11}$, (5- or 6-membered)heterocyclic ring comprising one or two heteroatoms selected from N, O and S, $(C_3-C_7)$cycloalkyl, $(C_6-C_{14})$aryl, (5- or 6-membered)heteroaryl comprising one, two or three heteroatoms selected from N, O and S, or a Linker Unit;

where $R_{10}$ and $R_{11}$ are independently H, $(C_1-C_3)$alkyl, a Protecting Group, or a Linker Unit;

wherein the aryl is unsubstituted or substituted with one to three substitutents selected from halo, nitro, cyano, $(C_1-C_6)$alkoxy, $NR_{10}R_{11}$, $(C=O)(C_1-C_6)$alkyl, $CO_2R_{10}$, $CONR_{10}R_{11}$, or a Linker Unit;

(5.) The compound of any one of the above (1.) to (3.), wherein $R_1$ is $(C_1-C_6)$alkyl, wherein the alkyl is unsubstituted or substituted with a substituent selected from $OR_{10}$, $NR_{10}R_{11}$, (5- or 6-membered)heterocyclic ring comprising one or two heteroatoms selected from N, O and S, $(C_3-C_7)$cycloalkyl, $(C_6-C_{14})$aryl, (5- or 6-membered)heteroaryl comprising one, two or three heteroatoms selected from N, O and S, or a Linker Unit.

(6.) The compound of the above (5.), wherein $R_1$ is $(C_1-C_3)$alkyl, wherein the alkyl is unsubstituted or substituted with a substituent selected from $OR_{10}$, $NR_{10}R_{11}$, (5- or 6-membered)heterocyclic ring comprising one or two heteroatoms selected from N, O and S, $(C_3-C_7)$cycloalkyl, $(C_6-C_{14})$aryl, (5- or 6-membered)heteroaryl comprising one, two or three heteroatoms selected from N, O and S, or a Linker Unit.

(7.) The compound of any one of the above (1.) to (6.), wherein the alkyl is unsubstituted.

(8.) The compound of any one of the above (1.) to (6.), wherein the alkyl is substituted.

(9.) The compound of the above (8.), wherein the alkyl is substituted with a substituent selected from hydroxyl, $NR_{10}R_{11}$, piperidinyl, morpholinyl, phenyl, pyridinyl, imidazolyl, and furyl;

wherein $R_{10}$ and $R_{11}$ are independently $(C_1-C_6)$alkyl; and phenyl is unsubstituted or substituted with a substituent selected from halo and nitro.

(10.) The compound of any one of the above (1.) to (3.), wherein $R_1$ is H.

(11.) The compound of any one of the above (1.) to (3.), wherein $R_1$ is $(C_4-C_6)$cycloalkyl.

(12.) The compound of any one of the above (1.) to (11.), wherein $R_2$ is selected from H or $(C_1-C_3)$alkoxy.

(13.) The compound of any one of the above (1.) to (11.), wherein $R_2$ is selected from H or methoxy.

(14.) The compound of the above (13.), wherein $R_2$ is H.

(15.) The compound of the above (13.), wherein $R_2$ is methoxy.

(16.) The compound of any one of the above (1.) to (15.), wherein $R_3$ is selected from H, $(C_1-C_3)$alkoxy, hydroxyl, O-Protecting Group, and O-Linker Unit.

(17.) The compound of any one of the above (1.) to (16.), wherein $R_3$ is selected from H, $(C_1-C_3)$alkoxy and hydroxyl.

(18.) The compound of the above (17.), wherein $R_3$ is selected from H, methoxy and hydroxyl.

(19.) The compound of the above (17.), wherein $R_3$H.

(20.) The compound of the above (17.), wherein $R_3$ is methoxy.

(21.) The compound of the above (17.), wherein $R_3$ is hydroxyl.

(22.) The compound of any one of the above (1.) to (21.), wherein $R_4$ is selected from $(C_1-C_3)$alkoxy, halo, hydroxyl, O-Protecting Group, and O-Linker Unit.

(23.) The compound of the above (22.), wherein $R_4$ is selected from $(C_1-C_3)$alkoxy, halo, O-Protecting Group and hydroxyl.

(24.) The compound of the above (22.), wherein $R_4$ is selected from methoxy, halo, O-Protecting Group and hydroxyl.

(25.) The compound of the above (22.), wherein $R_4$ is methoxy.

(26.) The compound of the above (22.), wherein $R_4$ is halo.

(27.) The compound of the above (22.), wherein $R_4$ is hydroxyl.

(28.) The compound of any one of the above (1.) to (27.), wherein $R_5$ is H.

(29.) The compound of any one of the above (1.) to (21.), wherein $R_4$ and $R_5$ are taken together with the carbons to which they are attached to form a 1,3-dioxolo ring.

(30.) The compound of any one of the above (1.) to (29.), wherein $R_6$ is H or $(C_1$-$C_3)$alkoxy.

(31.) The compound of any one of the above (1.) to (29.), wherein $R_6$ is H or methoxy.

(32.) The compound of any one of the above (1.) to (29.), wherein $R_6$ is H.

(33.) The compound of any one of the above (1.) to (29.), wherein $R_6$ is methoxy.

(34.) The compound of any one of the above (1.) to (33.), wherein $R_7$ is $(C_1$-$C_3)$alkoxy.

(35.) The compound of any one of the above (1.) to (33.), wherein $R_7$ is methoxy.

(36.) The compound of any one of the above (1.) to (35.), wherein $R_8$ is $(C_1$-$C_3)$alkoxy.

(37.) The compound of any one of the above (1.) to (35.), wherein $R_8$ is methoxy.

(38.) The compound of any one of the above (1.) to (33.), wherein $R_7$ and $R_8$ are taken together with the carbons to which they are attached to form a 1,3-dioxolo ring.

(39.) The compound of the above (1.) or the above (2.), wherein the compound has formula (Ib)

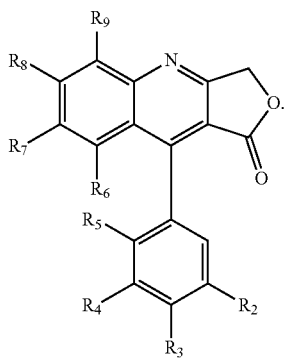

(40.) The compound of the above (39.), wherein $R_2$ is $(C_1$-$C_6)$alkoxy.

(41.) The compound of the above (39.), wherein $R_2$ is $(C_1$-$C_3)$alkoxy.

(42.) The compound of the above (39.), wherein $R_2$ is methoxy.

(43.) The compound of any one of the above (39.) to (42.), wherein $R_3$ is $(C_1$-$C_6)$alkoxy.

(44.) The compound of any one of the above (39.) to (42.), wherein $R_3$ is $(C_1$-$C_3)$alkoxy.

(45.) The compound of any one of the above (39.) to (42.), wherein $R_3$ is methoxy.

(46.) The compound of any one of the above (39.) to (45.), wherein $R_4$ is $(C_1$-$C_6)$alkoxy.

(47.) The compound of any one of the above (39.) to (45.), wherein $R_4$ is $(C_1$-$C_3)$alkoxy.

(48.) The compound of any one of the above (39.) to (45.), wherein $R_4$ is methoxy.

(49.) The compound of any one of the above (39.) to (48.), wherein $R_5$ is H.

(50.) The compound of any one of the above (39.) to (49.), wherein $R_6$ is H.

(51.) The compound of any one of the above (39.) to (50.), wherein $R_7$ and $R_8$ are taken together with the carbons to which they are attached to form a 1,3-dioxolo ring.

(52.) A compound selected from:
6,7-Methylenedioxy-4-(2-hydroxy-ethyl)-9-(3,4,5-trimethoxyphenyl)-4,9-dihydro-3H-furo[3,4-b]quinolin-1-one;
6,7-Methylenedioxy-4-(3-hydroxy-propyl)-9-(3,4,5-trimethoxyphenyl)-4,9-dihydro-3H-furo[3,4-b]quinolin-1-one;
6,7,8-Trimethoxy-9-(3,4,5-trimethoxyphenyl)-4,9-dihydro-3H-furo[3,4-b]quinolin-1-one;
6,7,8-Trimethoxy-9-(3-bromo-4,5-trimethoxyphenyl)-4,9-dihydro-3H-furo[3,4-b]quinolin-1-one;
6,7,8-Trimethoxy-9-(3-OTBDMS-4-methoxyphenyl)-4,9-dihydro-3H-furo[3,4-b]quinolin-1-one;
6,7,8-Trimethoxy-9-(3-hydroxy-4-methoxyphenyl)-4,9-dihydro-3H-furo[3,4-b]quinolin-1-one;
6,7-Methylenedioxy-9-(2,3-methylenedioxyphenyl)-4,9-dihydro-3H-furo[3,4-b]quinolin-1-one;
6,7-Methylenedioxy-9-(3,4,5-trimethoxyphenyl)-4,9-dihydro-3H-furo[3,4-b]quinolin-1-one;
6,7-Dimethoxy-9-(3,4,5-trimethoxyphenyl)-3H-furo[3,4-b]quinolin-1-one;
6,7-Methylenedioxy-4-methyl-9-(3,4,5-trimethoxyphenyl)-4,9-dihydro-3H-furo[3,4-b]quinolin-1-one;
6,7-Methylenedioxy-4-(cyclobutyl)-9-(3,4,5-trimethoxyphenyl)-4,9-dihydro-3H-furo[3,4-b]quinolin-1-one;
6,7-Methylenedioxy-4-(cyclopentyl)-9-(3,4,5-trimethoxyphenyl)-4,9-dihydro-3H-furo[3,4-b]quinolin-1-one;
6,7-Methylenedioxy-4-(cyclohexyl)-9-(3,4,5-trimethoxyphenyl)-4,9-dihydro-3H-furo[3,4-b]quinolin-1-one;
6,7-Methylenedioxy-4-(2-dimethyamino-ethyl)-9-(3,4,5-trimethoxyphenyl)-4,9-dihydro-3H-furo[3,4-b]quinolin-1-one;
6,7-Methylenedioxy-4-(2-piperidin-1-yl-ethyl)-9-(3,4,5-trimethoxyphenyl)-4,9-dihydro-3H-furo[3,4-b]quinolin-1-one;
6,7-Methylenedioxy-4-(2-morpholin-4-yl-ethyl)-9-(3,4,5-trimethoxyphenyl)-4,9-dihydro-3H-furo[3,4-b]quinolin-1-one;
6,7-Methylenedioxy-4-(4-fluoro-benzyl)-9-(3,4,5-trimethoxyphenyl)-4,9-dihydro-3H-furo[3,4-b]quinolin-1-one;
6,7-Methylenedioxy-4-(2-pyridin-2-yl-ethyl)-9-(3,4,5-trimethoxyphenyl)-4,9-dihydro-3H-furo[3,4-b]quinolin-1-one;
6,7-Methylenedioxy-4-[2-(4-fluorophenyl)-ethyl]-9-(3,4,5-trimethoxyphenyl)-4,9-dihydro-3H-furo[3,4-b]quinolin-1-one;
6,7-Methylenedioxy-4-[2-(4-chlorophenyl)-ethyl]-9-(3,4,5-trimethoxyphenyl)-4,9-dihydro-3H-furo[3,4-b]quinolin-1-one;
6,7-Methylenedioxy-4-[2-(4-nitrophenyl)-ethyl]-9-(3,4,5-trimethoxyphenyl)-4,9-dihydro-3H-furo[3,4-b]quinolin-1-one;
6,7-Methylenedioxy-4-(3-imidazol-1-yl-propyl)-9-(3,4,5-trimethoxyphenyl)-4,9-dihydro-3H-furo[3,4-b]quinolin-1-one;
6,7-Methylenedioxy-9-(4-hydroxy-3,5-dimethoxy-phenyl)-4,9-dihydro-3H-furo[3,4-b]quinolin-1-one;

6,7-Methylenedioxy-4-(cyclopentyl)-9-(4-hydroxy-3,5-dimethoxy-phenyl)-4,9-dihydro-3H-furo[3,4-b]quinolin-1-one;

6,7-Methylenedioxy-4-[2-(4-fluorophenyl)-ethyl]-9-(4-hydroxy-3,5-dimethoxy-phenyl)-4,9-dihydro-3H-furo[3,4-b]quinolin-1-one; or 6,7-Methylenedioxy-4-(furan-2-ylmethyl)-9-(4-hydroxy-3,5-dimethoxy-phenyl)-4,9-dihydro-3H-furo[3,4-b]quinolin-1-one; and a pharmaceutically acceptable salt thereof.

(53.) A compound, wherein the compound is:

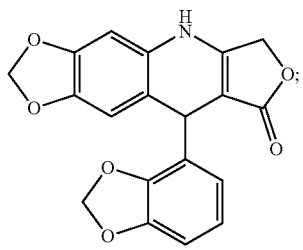 [SMILES: O=C1OCC2=C1C(c1cccc3c1OCO3)c1cc3c(cc1N2)OCO3]

or a pharmaceutically acceptable salt thereof.

(54.) A compound, wherein the compound is:

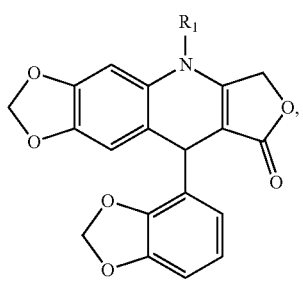

or a pharmaceutically acceptable salt thereof, wherein $R_1$ is a Linker Unit.

(55.) A compound, wherein the compound is:

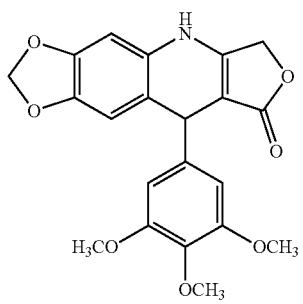 [SMILES: COc1cc(C2C3=C(COC3=O)Nc3cc4c(cc32)OCO4)cc(OC)c1OC]

or a pharmaceutically acceptable salt thereof.

(56.) A compound, wherein the compound is:

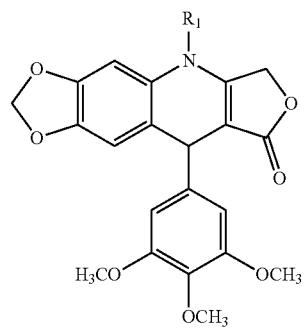

or a pharmaceutically acceptable salt thereof, wherein R1 is a Linker Unit.

(57.) A compound, wherein the compound is:

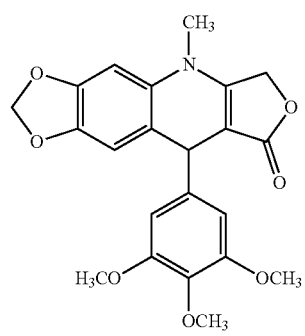 [SMILES: COc1cc(C2C3=C(COC3=O)N(C)c3cc4c(cc32)OCO4)cc(OC)c1OC]

or a pharmaceutically acceptable salt thereof.

(58.) A compound, wherein the compound is:

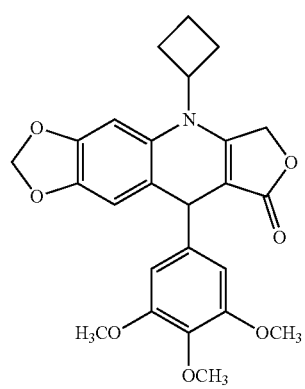 [SMILES: COc1cc(C2C3=C(COC3=O)N(C3CCC3)c3cc4c(cc32)OCO4)cc(OC)c1OC]

or a pharmaceutically acceptable salt thereof.

(59.) A compound, wherein the compound is:

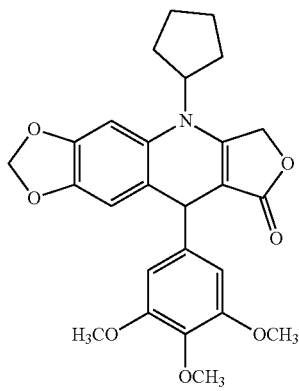 [SMILES: COc1cc(C2C3=C(COC3=O)N(C3CCCC3)c3cc4c(cc32)OCO4)cc(OC)c1OC]

or a pharmaceutically acceptable salt thereof.

(60.) A compound, wherein the compound is:

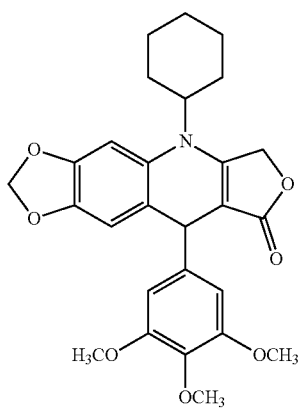 [SMILES: COc1cc(C2C3=C(COC3=O)N(C3CCCCC3)c3cc4c(cc32)OCO4)cc(OC)c1OC]

or a pharmaceutically acceptable salt thereof.

(61.) A compound, wherein the compound is:

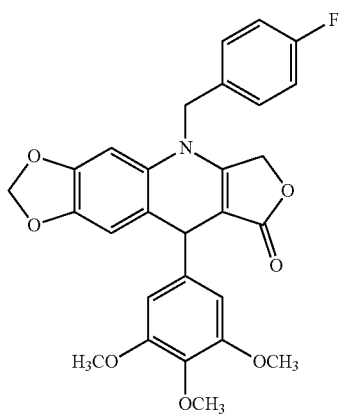 [SMILES: COc1cc(C2C3=C(COC3=O)N(Cc3ccc(F)cc3)c3cc4c(cc32)OCO4)cc(OC)c1OC]

or a pharmaceutically acceptable salt thereof.

(62.) A compound, wherein the compound is:

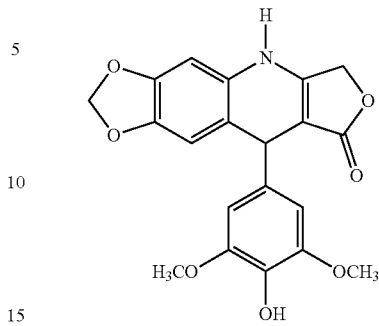

or a pharmaceutically acceptable salt thereof.

(63.) The compound of any one of the above (1.) to (51.), wherein the Linker Unit comprises a cleavable linker.

(64.) The compound of the above (63.), wherein the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage.

(65.) The compound of the above (63.), wherein the cleavable linker comprises a glycosidic bond, a hydrazone, a cathepsin-B-cleavable peptide, a disulfide or an ester bond.

(66.) The compound of the above (63.), wherein the cleavable linker comprises glucuronide.

(67.) The compound of the above (63.), wherein the Linker Unit is represented by formula (II):

$$A_a\text{-}W_w\text{-}Y_y \tag{II}$$

wherein:
A is a Stretcher Unit;
a is 0 or 1,
each -W- is independently an Amino Acid Unit,
w is an integer ranging from 0 to 12,
Y is a Spacer Unit, and
y is 0, 1 or 2.

(68.) The compound of the above (67.), wherein $A_a$ is maleimidocaproyl.

(69.) The compound of the above (67.) or (68.), wherein $W_w$ is Valine-Citrulline.

(70.) The compound of any one of the above (67.) to (69.), wherein $Y_y$ is p-aminobenzyloxycarbonyl.

(71.) The compound of any one of the above (63.) to (65.) and (67.) to (70.), wherein the Linker Unit comprises a monoclonal antibody.

(72.) A pharmaceutical composition comprising a compound of any one of the above (1.) to (71.) or a pharmaceutically acceptable salt thereof and a pharmaceutically acceptable carrier.

(73.) A pharmaceutical composition comprising a combination of compounds of any one of the above (1.) to (71.) or pharmaceutically acceptable salts thereof and a pharmaceutically acceptable carrier.

(74.) The pharmaceutical composition of the above (72.) or (73.), further comprising a therapeutically effective amount of chemotherapeutic agent selected from the group consisting of a tubulin-forming inhibitor, a topoisomerase inhibitor, and a DNA binder.

(75.) A method for killing or inhibiting the proliferation of tumor cells or cancer cells comprising treating tumor cells or cancer cells with a compound of any one of the above (1.) to (71.), or a pharmaceutical composition of any one of the above (72.) to (74.), in an amount effective to kill or inhibit the proliferation of the tumor cells or cancer cells.

(76.) A method for treating cancer in a patient in need thereof comprising administering to the patient a compound of any of the above (1.) to (71.), or a pharmaceutical composition of any one of the above (72.) to (74.), wherein the compound or pharmaceutical composition is administered in an amount effective to treat cancer.

(77.) The method of the above (76.), further comprising administering an effective amount of a second therapeutic agent.

(78.) A method of determining inhibition of cellular proliferation by a compound, comprising contacting cells in a cell culture medium with the compound of any of the above (1.) to (71.) and measuring the cytotoxic activity of the compound, whereby proliferation of the cells is inhibited.

(79.) A method of inhibiting the growth of tumor cells that overexpress a tumor-associated antigen comprising administering to a patient the compound of any of the above (1.) to (71.) conjugated to an antibody that is specific for the tumor-associated antigen, and optionally a second therapeutic agent wherein the compound and the second therapeutic agent are each administered in amounts effective to inhibit growth of tumor cells in the patient.

(80.) The method of the above (79.), wherein the compound sensitizes the tumor cells to the second therapeutic agent.

(81.) The method of the above (79.), wherein the compound induces cell death.

(82.) The method of the above (79.), wherein the compound induces apoptosis.

(83.) The method of the above (79.), wherein the tumor cell is selected from the group consisting of Kaposi's sarcoma, Ewing's sarcoma, Wilms' tumor, rhabdomyosarcoma, testicular cancer, lymphoma, Non-Hodgkin's lymphoma, Hodgkin's lymphoma, glioblastoma multiforme, neuroblastoma, brain tumors, bone cancer, adrenal cortex cancer, endometrium cancer, ovarian cancer, cancer of the soft tissues, gestational trophoblastic tumors, hepatoblastoma, cancer of the lymph system, cancers of the blood and lymph system, multiple myeloma, myelodysplastic syndromes, retinoblastoma, thymoma, bladder cancer, stomach cancer, uterine cancer, leukemia, breast cancer, central nervous system cancer, lung cancer, small cell carcinoma, squamous cell lung carcinoma, non-small cell lung cancer, colon cancer, pancreatic cancer, and prostate cancer.

(84.) A use of the compound of any of the above (1.) to (71.) in the manufacture of a medicament for treating cancer.

(85.) An article of manufacture comprising the compound of any of the above (1.) to (71.), a container, and a package insert or label indicating that the compound can be used to treat cancer characterized by the overexpression of at least one tumor-associated antigen.

DEFINITIONS

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The phrase "pharmaceutically acceptable salt," as used herein, refers to pharmaceutically acceptable organic or inorganic salts of a compound of the disclosure. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The term "pharmaceutically acceptable carrier" refers to a diluent, adjuvant or excipient, with which a compound of the disclosure may be administered. Pharmaceutically acceptable carriers include any and all solvents, diluents, or other liquid vehicles, dispersions or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the disclosure such as by producing any undesirable biological effect or otherwise interacting in a deleterious manner with any other component(s) of the pharmaceutically acceptable composition, its use is contemplated to be within the scope of this disclosure. Examples of pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols, such a propylene glycol or polyethylene glycol; esters, such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "therapeutically effective amount" refers to an amount of a compound of the disclosure effective to treat a disease or disorder in a patient. In the case of cancer, the therapeutically effective amount of the compound may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the compound may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

The terms "treat" or "treatment" refer to therapeutic treatment and prophylactic measures to obtain a beneficial or desired result. For purposes of this disclosure, beneficial or desired results include, but are not limited to, alleviation of symptoms, diminishment of extent of disease, stabilized (i.e., not worsening) state of disease, delay or slowing of disease progression, amelioration or palliation of the disease state, remission (whether partial or total), whether detectable or undetectable and prevention of relapse. "Treatment" can also include prolonging survival as compared to expected survival if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

The term "patient," as used herein, includes, but is not limited to, a human, rat, mouse, guinea pig, monkey, pig, goat, cow, horse, dog, cat, bird and fowl. In some embodiments, the patient is a human.

The terms "cancer" and "cancerous" refer to or describe the physiological condition or disorder in mammals that is typically characterized by unregulated cell growth. A "tumor" comprises one or more cancerous cells.

Exemplary cancers include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Kaposi's sarcoma, Ewing's sarcoma, leiomyosarcoma, rhabdomyosarcoma, colon cancer, colorectal cancer, kidney cancer, pancreatic cancer, bone cancer, breast cancer, endometrium cancer, ovarian cancer, prostate cancer, esophogeal cancer, stomach cancer, oral cancer, nasal cancer, throat cancer, central nervous system cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, squamous cell lung carcinoma, non-small cell lung cancer, bladder cancer, lung cancer, epithelial carcinoma, glioma, glioblastoma multiforme, brain tumors, astrocytoma, medulloblastoma, craniopharyngioma, ependymoma, pinealoma, hemangioblastoma, acoustic neuroma, oligodendroglioma, meningioma, skin cancer, melanoma, neuroblastoma, adrenal cortex cancer, retinoblastoma, cancer of the soft tissues, leukemia, acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), hairy cell leukemia, multiple myeloma, Hodgkin's lymphoma, non-Hodgkin's lymphoma, Waldenstrom's macroglobulinemia, heavy chain disease, gestational trophoblastic tumors, hepatoblastoma, cancer of the lymph system, cancers of the blood and lymph system, myelodysplastic syndromes, thymoma, and polycythemia vera.

The term "cytotoxic activity" refers to a cell-killing, a cytostatic or an anti-proliferative effect of a compound of the disclosure. Methods for measuring cytotoxic activity are well-known in the art. Cytotoxic activity may be expressed as the $IC_{50}$ value, which is the concentration (molar or mass) per unit volume at which half the cells survive.

The term "$(C_1-C_6)$alkyl" refers to saturated linear and branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_6)$alkyl groups include methyl, ethyl, n-propyl, iso-propyl, n-butyl, tert-butyl, n-pentyl, n-hexyl, and the like.

The term "$(C_1-C_3)$alkyl" refers to saturated linear and branched hydrocarbon structures having 1, 2 or 3 carbon atoms. When an alkyl residue having a specific number of carbons is named, all geometric isomers having that number of carbons are intended to be encompassed; thus, for example, "propyl" includes n-propyl and iso-propyl. Examples of $(C_1-C_3)$alkyl groups include methyl, ethyl, n-propyl and iso-propyl.

The term "$(C_6-C_{14})$aryl" refers to a monovalent aromatic hydrocarbon group which may be monocyclic, bicyclic or tricyclic, wherein at least one ring in the system is aromatic and wherein each ring in the system contains 3, 4, 5, 6 or 7 ring members. Examples of $(C_6-C_{14})$aryl groups include without limitation phenyl, naphthyl, indanyl, indenyl, tetralinyl, anthryl and phenanthryl.

The term "(5- or 6-membered)heteroaryl" refers to a monocyclic aromatic heterocycle ring of 5 or 6 members, i.e., a monocyclic aromatic ring comprising at least one ring heteroatom, e.g., 1, 2, 3, or 4 ring heteroatoms, each independently selected from nitrogen, oxygen, and sulfur. A (5- or 6-membered)heteroaryl group can be attached to the parent structure through a carbon or heteroatom. Examples of (5- or 6-membered)heteroaryls include pyridyl, pyrrolyl, pyrazolyl, furyl, imidazolyl, oxazolyl, imidazolyl, thiazolyl, isoxazolyl, 1,2,3 oxadiazolyl, 1,3,4-oxadiazolyl, 1,2,5 oxadiazolyl, 1,2,3-triazolyl, pyrazolyl, isothiazolyl, pyridazinyl, pyrimidyl, pyrazinyl, 1,2,3 thiadiazolyl, 1,3,4-thiadiazolyl, 1,2,5-thiadiazolyl, 1,3,5 triazinyl, and thiophenyl.

The term "(5-membered)heteroaryl" refers to a monocyclic aromatic heterocycle ring of 5 members, i.e., a monocyclic aromatic ring comprising at least one ring heteroatom, e.g., 1, 2, 3, or 4 ring heteroatoms, each independently selected from nitrogen, oxygen, and sulfur. A (5-membered) heteroaryl group can be attached to the parent structure through a carbon or heteroatom. Examples of (5-membered)

heteroaryls include pyrrolyl, pyrazolyl, furyl, imidazolyl, oxazolyl, imidazolyl, thiazolyl, isoxazolyl, 1,2,3 oxadiazolyl, 1,3,4-oxadiazolyl, 1,2,5 oxadiazolyl, 1,2,3-triazolyl, pyrazolyl, isothiazolyl, 1,2,3 thiadiazolyl, 1,3,4-thiadiazolyl and 1,2,5-thiadiazolyl.

The term "(6-membered)heteroaryl" refers to a monocyclic aromatic heterocycle ring of 6 members, i.e., a monocyclic aromatic ring comprising at least one ring heteroatom, e.g., 1, 2, 3, or 4 ring heteroatoms, each independently selected from nitrogen, oxygen, and sulfur. A (6-membered) heteroaryl group can be attached to the parent structure through a carbon or heteroatom. Examples of (6-membered) heteroaryls include pyridyl, pyridazinyl, pyrimidyl, pyrazinyl, 1,3,5 triazinyl, and thiophenyl.

The term "($C_3$-$C_7$)cycloalkyl" refers to a saturated cyclic hydrocarbon containing 3, 4, 5, 6 or 7 ring carbon atoms. Examples of ($C_3$-$C_7$)cycloalkyl groups include cyclopropyl, cyclobutyl, cyclopentyl, cyclohexyl, cycloheptyl and the like.

The term "(5- or 6-membered)heterocyclyl" refers to a 5- or 6-membered, saturated or partially unsaturated, monocyclic-heterocycle containing 1, 2, or 3 ring heteroatoms, each independently selected from nitrogen, oxygen, and sulfur, wherein the nitrogen and sulfur heteroatoms may optionally be oxidized and the nitrogen heteroatom may optionally be quaternized. Examples of "(5- or 6-membered)heterocyclyl groups include pyrrolidinyl, piperidinyl, piperazinyl, tetrahydro-oxazinyl, tetrahydrofuran, thiolane, dithiolane, pyrroline, pyrrolidine, pyrazoline, pyrazolidine, imidazoline, imidazolidine, tetrahydrofuranone, γ-butyrolactone, 2H-pyran, 4H-pyran, dioxolane, tetrahydropyran, dioxane, dihydrothiophene, piperazine, morpholine, thiomorpholine, oxazine, tetrahydro-oxazinyl, and the like.

The term "($C_6$)heterocycloalkyl" refers to a 6-membered, saturated or partially unsaturated, bridged, mono- or bicyclic-heterocycle containing 1, 2, or 3 ring heteroatoms each independently selected from nitrogen, oxygen, and sulfur, wherein the nitrogen and sulfur heteroatoms may optionally be oxidized and the nitrogen heteroatom may optionally be quaternized. A heterocycloalkyl group can be attached to the parent structure through a carbon or heteroatom. Examples of ($C_6$)heterocycloalkyl groups include piperidinyl, piperazinyl, tetrahydro-oxazinyl, tetrahydropyran, dioxane, morpholine, thiomorpholine, and the like.

The term "amino acid" refers to both natural and unnatural amino acids. Examples of amino acids include alanine, β-alanine, N-methyl alanine, N-ethyl alanine, N-methyl-β-alanine, N-ethyl-β-alanine, arginine, asparagine, aspartic acid, cysteine, homocysteine, cystine, glutamic acid, glutamine, glycine, N-ethyl glycine, N-propyl glycine, N-isopropyl glycine, phenylalanine, 4-aminophenylalanine, 3-aminophenylalanine, 2-aminophenylalanine, histidine, isoleucine, alloisoleucine, lysine, ornithine, citrulline, leucine, norleucine, t-leucine, methionine, proline, pipecolic acid, serine, homoserine, isoserine, threonine, allothreonine, valine, norvaline, isovaline, α-methylnorvaline, tryptophan, tyrosine, γ-aminobutyric acid, δ-aminolevulinic acid, 4-aminobenzoic acid, α-aminoisobuyric acid, dehydroalanine, cystathionine, lanthionine, djenkolic acid, diaminopimelic acid, α-amino-n-heptanoic acid, α,β-diaminopropionic acid, α,γ-diaminopropionic acid, β-amino-n-butyric acid, β-aminoisobutyric acid, sarcosine, α-hydroxy-γ-aminobutyric acid and the like.

The term "Protecting Group" refers to any group that is capable of reversibly protecting another functional group from undergoing an undesired reaction. Suitable protecting groups, as well as suitable conditions for protection and deprotection are well-known in the art and are described e.g., in T. W. Greene and P. G. M. Wuts, "Protective Groups in Organic Synthesis", Third edition, Wiley, New York 1999, and references cited therein.

The term "antibody" as used herein includes whole antibodies, monoclonal antibodies, polyclonal antibodies, monospecific antibodies, multispecific antibodies (e.g., bispecific antibodies), and antibody fragments that exhibit the desired biological activity. An antibody may be of any type or class (e.g., IgG, IgE, IgM, IgD, and IgA) or subclass (e.g., IgG1, IgG2, IgG3, IgG4, IgA1 and IgA2). The antibody may be derived from any suitable species. In some embodiments, the antibody is of human or murine origin. An antibody may be, for example, human, humanized or chimeric.

The term "monoclonal antibodies" as used herein refers to antibodies produced by a single clone of cells or cell line and comprising identical antibody molecules. The term "polyclonal antibodies" refers to antibodies produced by more than one type of cell or cell line and comprising different antibody molecules.

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C=N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

Compounds of Formula (I)

In one embodiment, the present disclosure provides a compound of formula (I),

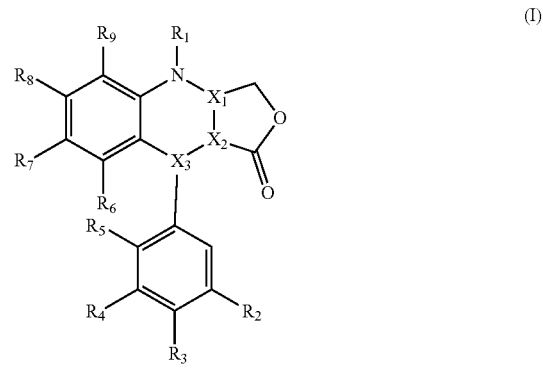

(I)

or a pharmaceutically acceptable salt thereof, wherein:
$R_1$ is selected from H, ($C_1$-$C_6$)alkyl, ($C_3$-$C_7$)cycloalkyl, a lone pair of electrons when N and $X_1$ form a double bond, or a Linker Unit;
wherein the alkyl is unsubstituted or substituted with a substituent selected from $OR_{10}$, $NR_{10}R_{11}$, (5- or 6-membered)heterocyclic ring comprising one or two heteroatoms selected from N, O and S, ($C_3$—$C_7$)cycloalkyl, ($C_6$-$C_{14}$)aryl, (5- or 6-membered)heteroaryl comprising one, two or three heteroatoms selected from N, O and S, or a Linker Unit;

where $R_{10}$ and $R_{11}$ are independently H, $(C_1-C_6)$alkyl, a Protecting Group, or a Linker Unit;

wherein the aryl is unsubstituted or substituted with one to three substituents selected from halo, nitro, cyano, $(C_1-C_6)$alkoxy, $NR_{10}R_{11}$, $(C=O)(C_1-C_6)$alkyl, $CO_2R_{10}$, $CONR_{10}R_{11}$, or a Linker Unit;

$R_2$, $R_3$ and $R_4$ are independently selected from H, $(C_1-C_6)$alkoxy, halo, $OR_{10}$, or $NR_{10}R_{11}$;

$R_5$ is H;

or $R_4$ and $R_5$ are taken together with the carbons to which they are attached to form a 1,3-dioxolo ring;

$R_6$ is selected from H or $(C_1-C_6)$alkoxy;

$R_7$ is $(C_1-C_6)$alkoxy;

$R_8$ is $(C_1-C_6)$alkoxy;

or $R_7$ and $R_8$ are taken together with the carbons to which they are attached to form a 1,3-dioxolo ring;

$R_9$ is H;

$X_1$, $X_2$ and $X_3$ are carbon and either (a) $X_1$ and N form a double bond and $X_2$ and $X_3$ form a double bond; or (b) $X_1$ and $X_2$ form a double bond.

In one embodiment, $R_1$ is selected from H, $(C_1-C_6)$alkyl, or $(C_3-C_7)$cycloalkyl. In another embodiment, $R_1$ is selected from H, $(C_1-C_6)$alkyl, or a lone pair of electrons when N and $X_1$ form a double bond. In another embodiment, R1 is selected from H, $(C_1-C_6)$alkyl, or Linker Unit. In another embodiment, R1 is selected $(C_1-C_6)$alkyl, $(C_3-C_7)$cycloalkyl, or a lone pair of electrons when N and $X_1$ form a double bond. n another embodiment, R1 is selected $(C_1-C_6)$alkyl, $(C_3-C_7)$cycloalkyl, or Linker Unit. In another embodiment, R1 is selected from $(C_3-C_7)$cycloalkyl, a lone pair of electrons when N and $X_1$ form a double bond, or Linker Unit. In embodiments of this paragraph in which R1 is $(C_1-C_6)$alkyl, the alkyl is unsubstituted in one embodiment and substituted in a second embodiment, wherein the substituents are selected from $OR_{10}$, $NR_{10}R_{11}$, (5- or 6-membered)heterocyclic ring comprising one or two heteroatoms selected from N, O and S, $(C_3-C_7)$cycloalkyl, $(C_6-C_{14})$aryl, (5- or 6-membered)heteroaryl comprising one, two or three heteroatoms selected from N, O and S, or a Linker Unit.

In another embodiment, R1 is H. In another embodiment, R1 is $(C_1-C_6)$alkyl. In another embodiment, $R_1$ is methyl, ethyl, propyl or butyl. In another embodiment, $R_1$ is methyl, ethyl or propyl. In another embodiment, $R_1$ is methyl, ethyl or butyl. In another embodiment, $R_1$ is ethyl, propyl or butyl. In another embodiment, $R_1$ is methyl or ethyl. In another embodiment, $R_1$ is methyl or propyl. In another embodiment, $R_1$ is methyl or butyl. In another embodiment, $R_1$ is ethyl or propyl. In another embodiment, $R_1$ is ethyl or butyl. In another embodiment, $R_1$ is propyl or butyl. In another embodiment, $R_1$ is methyl. In another embodiment, $R_1$ is ethyl. In another embodiment, $R_1$ is propyl. In another embodiment, $R_1$ is butyl.

In one embodiment, $R_1$ is $(C_1-C_6)$alkyl substituted with a substituent selected from $OR_{10}$, $NR_{10}R_{11}$, (5- or 6-membered)heterocyclic ring comprising one or two heteroatoms selected from N, O and S, $(C_3-C_7)$cycloalkyl, $(C_6-C_{14})$aryl, (5- or 6-membered)heteroaryl comprising one, two or three heteroatoms selected from N, O and S, or a Linker Unit. In one embodiment, the substituent is selected from OH, N-di $(C_1-C_6)$alkyl, piperidinyl, morpholinyl, phenyl, pyridinyl, imidazolyl, or furyl, wherein the phenyl is unsubstituted or substituted with halo or nitro.

In one embodiment, $R_1$ is $(C_3-C_7)$cycloalkyl. In another embodiment, $R_1$ is cyclopropyl, cyclobutyl, cyclopentyl or cyclohexyl. In another embodiment, $R_1$ is cyclopropyl, cyclobutyl, cyclopentyl or cycloheptyl. In another embodiment, $R_1$ is cyclopropyl, cyclobutyl or cyclopentyl. In another embodiment, $R_1$ is cyclopropyl, cyclobutyl or cyclohexyl. In another embodiment, $R_1$ is cyclopropyl, cyclobutyl or cycloheptyl. In another embodiment, $R_1$ is cyclopropyl, cyclopentyl or cyclohexyl. In another embodiment, $R_1$ is cyclobutyl, cyclopentyl or cyclohexyl. In another embodiment, $R_1$ is cyclobutyl, cyclopentyl or cycloheptyl. In another embodiment, $R_1$ is cyclopentyl, cyclohexyl or cycloheptyl. In another embodiment, $R_1$ is cyclopropyl or cyclobutyl. In another embodiment, $R_1$ is cyclopropyl or cyclopentyl. In another embodiment, $R_1$ is cyclopropyl or cyclohexyl. In another embodiment, $R_1$ is cyclopropyl or cycloheptyl. In another embodiment, $R_1$ is cyclobutyl or cyclopentyl. In another embodiment, $R_1$ is cyclobutyl or cyclohexyl. In another embodiment, $R_1$ is cyclobutyl or cycloheptyl. In another embodiment, $R_1$ is cyclopentyl or cyclohexyl. In another embodiment, $R_1$ is cyclopentyl or cycloheptyl. In another embodiment, $R_1$ is cyclohexyl or cycloheptyl. In another embodiment, $R_1$ is cyclopropyl. In another embodiment, $R_1$ is cyclobutyl. In another embodiment, $R_1$ is cyclopentyl. In another embodiment, $R_1$ is cyclohexyl. In another embodiment, $R_1$ is cycloheptyl.

In one embodiment, $R_1$ is a lone pair of electrons when N and $X_1$ form a double bond. In another embodiment, $R_1$ is a Linker Unit.

In one embodiment, $R_2$ is selected from H, $(C_1-C_6)$alkoxy, $OR_{10}$, or $NR_{10}R_{11}$. In another embodiment, $R_2$ is H or $(C_1-C_6)$alkoxy. In another embodiment, $R_2$ is H, methoxy, ethoxy or propoxy. In another embodiment, $R_2$ is H, methoxy or ethoxy. In another embodiment, $R_2$ is H, methoxy or propoxy. In another embodiment, $R_2$ is methoxy, ethoxy or propoxy. In another embodiment, $R_2$ is H or methoxy. In another embodiment, $R_2$ is H or ethoxy. In another embodiment, $R_2$ is H or propoxy. In another embodiment, $R_2$ is methoxy or ethoxy. In another embodiment, $R_2$ is methoxy or propoxy. In another embodiment, $R_2$ is ethoxy or propoxy. In another embodiment, $R_2$ is H. In another embodiment, $R_2$ is $(C_1-C_6)$alkoxy. In another embodiment, $R_2$ is methoxy. In another embodiment, $R_2$ is ethoxy. In another embodiment, $R_2$ is $OR_{10}$. In another embodiment, $R_2$ is $NR_{10}R_{11}$.

In one embodiment, $R_3$ is selected from H, $(C_1-C_6)$alkoxy, $OR_{10}$, or $NR_{10}R_{11}$. In another embodiment, $R_3$ is H, $(C_1-C_6)$alkoxy or hydroxyl. In another embodiment, $R_3$ is H or $(C_1-C_6)$alkoxy. In another embodiment, $R_3$ is H or hydroxyl. In another embodiment, $R_3$ is $(C_1-C_6)$alkoxy or hydroxyl. In another embodiment, $R_3$ is H, methoxy, ethoxy, propoxy or hydroxyl. In another embodiment, $R_3$ is H, methoxy or ethoxy. In another embodiment, $R_3$ is H, methoxy or propoxy. In another embodiment, $R_3$ is H, methoxy or hydroxyl. In another embodiment, $R_3$ is methoxy, ethoxy or propoxy. In another embodiment, $R_3$ is methoxy, ethoxy or hydroxyl. In another embodiment, $R_3$ is ethoxy, propoxy or hydroxyl. In another embodiment, $R_3$ is H or methoxy. In another embodiment, $R_3$ is H or ethoxy. In another embodiment, $R_3$ is H or propoxy. In another embodiment, $R_3$ is H or hydroxyl. In another embodiment, $R_3$ is methoxy or ethoxy. In another embodiment, $R_3$ is methoxy or propoxy. In another embodiment, $R_3$ is methoxy or hydroxyl. In another embodiment, $R_3$ is ethoxy or propoxy. In another embodiment, $R_3$ is ethoxy or hydroxyl. In another embodiment, $R_3$ is propoxy or hydroxyl. In another embodiment, $R_3$ is H. In another embodiment, $R_3$ is $(C_1-C_6)$alkoxy. In another embodiment, $R_3$ is methoxy. In another embodiment, $R_3$ is ethoxy. In another embodiment, $R_3$ is $OR_{10}$. In another embodiment, $R_3$ is hydroxyl. In another embodiment, $R_3$ is $NR_{10}R_{11}$.

In one embodiment, $R_4$ is H, $(C_1-C_6)$alkoxy, halo, $OR_{10}$, or $NR_{10}R_{11}$, or $R_4$ and $R_5$ are taken together with the carbons to which they are attached to form a 1,3-dioxolo ring. In another embodiment, $R_4$ is $(C_1-C_6)$alkoxy, halo or $OR_{10}$, or $R_4$ and $R_5$ are taken together with the carbons to which they are attached to form a 1,3-dioxolo ring. In another embodiment, $R_4$ is $(C_1-C_6)$alkoxy, halo or $OR_{10}$. In another embodiment, $R_4$ is $(C_1-C_6)$alkoxy or halo, or $R_4$ and $R_5$ are taken together with the carbons to which they are attached to form a 1,3-dioxolo ring. In another embodiment, $R_4$ is halo or $OR_{10}$, or $R_4$ and $R_5$ are taken together with the carbons to which they are attached to form a 1,3-dioxolo ring. In another embodiment, $R_4$ is $(C_1-C_6)$alkoxy or halo. In another embodiment, $R_4$ is $(C_1-C_6)$alkoxy or $OR_{10}$. In another embodiment, $R_4$ is $(C_1-C_6)$alkoxy or $NR_{10}R_{11}$. In another embodiment, $R_4$ is $(C_1-C_6)$alkoxy or $OR_{10}$. In another embodiment, $R_4$ is $(C_1-C_6)$alkoxy, or $R_4$ and $R_5$ are taken together with the carbons to which they are attached to form a 1,3-dioxolo ring. In another embodiment, $R_4$ is halo or $OR_{10}$. In another embodiment, $R_4$ is halo or $R_4$ and $R_5$ are taken together with the carbons to which they are attached to form a 1,3-dioxolo ring. In another embodiment, $R_4$ is $OR_{10}$, or $R_4$ and $R_5$ are taken together with the carbons to which they are attached to form a 1,3-dioxolo ring. In another embodiment, $R_4$ is methoxy, ethoxy, propoxy, bromo, fluoro, chloro, hydroxyl, or O-Protecting Group, or $R_4$ and $R_5$ are taken together with the carbons to which they are attached to form a 1,3-dioxolo ring. In another embodiment, $R_4$ is methoxy, bromo, hydroxyl, or O-Protecting Group, or $R_4$ and $R_5$ are taken together with the carbons to which they are attached to form a 1,3-dioxolo ring. In another embodiment, $R_4$ is methoxy. In another embodiment, $R_4$ is bromo. In another embodiment, $R_4$ is hydroxyl. In another embodiment, $R_4$ is O-Protecting Group.

In one embodiment, $R_5$ is H. In another embodiment, $R_4$ and $R_5$ are taken together with the carbons to which they are attached to form a 1,3-dioxolo ring.

In one embodiment, $R_6$ is H. In another embodiment, $R_6$ is $(C_1-C_6)$alkoxy. In another embodiment, $R_6$ is H, methoxy, ethoxy or propoxy. In another embodiment, $R_6$ is H, methoxy or ethoxy. In another embodiment, $R_6$ is H, methoxy or propoxy. In another embodiment, $R_6$ is methoxy, ethoxy or propoxy. In another embodiment, $R_6$ is H or methoxy. In another embodiment, $R_6$ is H or ethoxy. In another embodiment, $R_6$ is H or propoxy. In another embodiment, $R_6$ is methoxy or ethoxy. In another embodiment, $R_6$ is methoxy or propoxy. In another embodiment, $R_6$ is ethoxy or propoxy. In another embodiment, $R_6$ is methoxy. In another embodiment, $R_6$ is ethoxy.

In one embodiment, $R_7$ is methoxy, ethoxy or propoxy. In another embodiment, $R_7$ is methoxy or ethoxy. In another embodiment, $R_7$ is methoxy or propoxy. In another embodiment, $R_7$ is ethoxy or propoxy. In another embodiment, $R_7$ is methoxy. In another embodiment, $R_7$ is ethoxy.

In one embodiment, $R_8$ is methoxy, ethoxy or propoxy. In another embodiment, $R_8$ is methoxy or ethoxy. In another embodiment, $R_8$ is methoxy or propoxy. In another embodiment, $R_8$ is ethoxy or propoxy. In another embodiment, $R_8$ is methoxy. In another embodiment, $R_8$ is ethoxy.

In one embodiment, $R_7$ and $R_8$ are taken together with the carbons to which they are attached to form a 1,3-dioxolo ring.

In one embodiment, $X_1$, $X_2$ and $X_3$ are carbon and $X_1$ and N form a double bond and $X_2$ and $X_3$ form a double bond. In another embodiment, $X_1$, $X_2$ and $X_3$ are carbon and $X_1$ and $X_2$ form a double bond. In one embodiment, $R_2$ is selected from H or $(C_1-C_6)$alkoxy; $R_3$ is selected from H, $(C_1-C_6)$alkoxy, hydroxyl, O-Protecting Group, or O-Linker Unit; and $R_4$ is selected from $(C_1-C_6)$alkoxy, halo, hydroxyl, O-Protecting Group, or O-Linker Unit.

In one embodiment, the present disclosure provides a compound of formula (Ia),

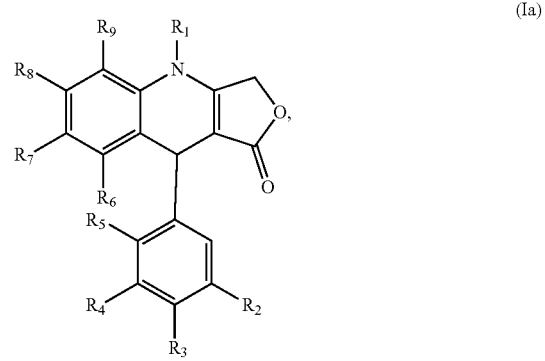

(Ia)

or a pharmaceutically acceptable salt thereof, wherein each of $R_1$, $R_2$, $R_3$, $R_4$, $R_5$, $R_6$, $R_7$, $R_8$ and $R_9$ are as defined above in connection with the compounds of formula (I).

In one embodiment, $R_1$ is selected from H, $(C_1-C_6)$alkyl, or $(C_3-C_7)$cycloalkyl. In another embodiment, $R_1$ is selected from H, $(C_1-C_6)$alkyl, or Linker Unit. In another embodiment, $R_1$ is selected $(C_1-C_6)$alkyl, $(C_3-C_7)$cycloalkyl, or Linker Unit. In another embodiment, $R_1$ is selected from $(C_3-C_7)$cycloalkyl or Linker Unit. In embodiments of this paragraph in which $R_1$ is $(C_1-C_6)$alkyl, the alkyl is unsubstituted in one embodiment and substituted in a second embodiment, wherein the substituents are selected from $OR_{10}$, $NR_{10}R_{11}$, (5- or 6-membered)heterocyclic ring comprising one or two heteroatoms selected from N, O and S, $(C_3-C_7)$cycloalkyl, $(C_6-C_{14})$aryl, (5- or 6-membered)heteroaryl comprising one, two or three heteroatoms selected from N, O and S, or a Linker Unit.

In another embodiment, $R_1$ is H. In another embodiment, $R_1$ is $(C_1-C_6)$alkyl. In another embodiment, $R_1$ is methyl, ethyl, propyl or butyl. In another embodiment, $R_1$ is methyl, ethyl or propyl. In another embodiment, $R_1$ is methyl, ethyl or butyl. In another embodiment, $R_1$ is ethyl, propyl or butyl. In another embodiment, $R_1$ is methyl or ethyl. In another embodiment, $R_1$ is methyl or propyl. In another embodiment, $R_1$ is methyl or butyl. In another embodiment, $R_1$ is ethyl or propyl. In another embodiment, $R_1$ is ethyl or butyl. In another embodiment, $R_1$ is propyl or butyl. In another embodiment, $R_1$ is methyl. In another embodiment, $R_1$ is ethyl. In another embodiment, $R_1$ is propyl. In another embodiment, $R_1$ is butyl.

In one embodiment, $R_1$ is $(C_1-C_6)$alkyl substituted with a substituent selected from $OR_{10}$, $NR_{10}R_{11}$, (5- or 6-membered)heterocyclic ring comprising one or two heteroatoms selected from N, O and S, $(C_3-C_7)$cycloalkyl, $(C_6-C_{14})$aryl, (5- or 6-membered)heteroaryl comprising one, two or three heteroatoms selected from N, O and S, or a Linker Unit. In one embodiment, the substituent is selected from OH, N-di$(C_1-C_6)$alkyl, piperidinyl, morpholinyl, phenyl, pyridinyl, imidazolyl, or furyl, wherein the phenyl is unsubstituted or substituted with halo or nitro.

In one embodiment, $R_1$ is $(C_3-C_7)$cycloalkyl. In another embodiment, $R_1$ is cyclopropyl, cyclobutyl, cyclopentyl or cyclohexyl. In another embodiment, $R_1$ is cyclopropyl, cyclobutyl, cyclopentyl or cycloheptyl. In another embodiment, $R_1$ is cyclopropyl, cyclobutyl or cyclopentyl. In another embodiment, $R_1$ is cyclopropyl, cyclobutyl or cyclohexyl. In another embodiment, $R_1$ is cyclopropyl, cyclobutyl or cycloheptyl. In another embodiment, $R_1$ is cyclobutyl, cyclopentyl or cyclohexyl. In another embodiment, $R_1$ is cyclobutyl, cyclopentyl or cycloheptyl. In another embodiment, $R_1$ is cyclopentyl, cyclohexyl or cycloheptyl. In another embodiment, $R_1$ is cyclopropyl or cyclobutyl. In another embodiment, $R_1$ is cyclopropyl or cyclopentyl. In another embodiment, $R_1$ is cyclopropyl or cyclohexyl. In another embodiment, $R_1$ is cyclopropyl or cycloheptyl. In another embodiment, $R_1$ is cyclobutyl or cyclopentyl. In another embodiment, $R_1$ is cyclobutyl or cyclohexyl. In another embodiment, $R_1$ is cyclobutyl or cycloheptyl. In another embodiment, $R_1$ is cyclopentyl or cyclohexyl. In another embodiment, $R_1$ is cyclopentyl or cycloheptyl. In another embodiment, $R_1$ is cyclohexyl or cycloheptyl. In another embodiment, $R_1$ is cyclopropyl. In another embodiment, $R_1$ is cyclobutyl. In another embodiment, $R_1$ is cyclopentyl. In another embodiment, $R_1$ is cyclohexyl. In another embodiment, $R_1$ is cycloheptyl.

In another embodiment, $R_1$ is a Linker Unit.

In one embodiment, $R_2$ is selected from H, $(C_1-C_6)$alkoxy, $OR_{10}$, or $NR_{10}R_{11}$. In another embodiment, $R_2$ is H or $(C_1-C_6)$alkoxy. In another embodiment, $R_2$ is H, methoxy, ethoxy or propoxy. In another embodiment, $R_2$ is H, methoxy or ethoxy. In another embodiment, $R_2$ is H, methoxy or propoxy. In another embodiment, $R_2$ is methoxy, ethoxy or propoxy. In another embodiment, $R_2$ is H or methoxy. In another embodiment, $R_2$ is H or ethoxy. In another embodiment, $R_2$ is H or propoxy. In another embodiment, $R_2$ is methoxy or ethoxy. In another embodiment, $R_2$ is methoxy or propoxy. In another embodiment, $R_2$ is ethoxy or propoxy. In another embodiment, $R_2$ is H. In another embodiment, $R_2$ is $(C_1-C_6)$alkoxy. In another embodiment, $R_2$ is methoxy. In another embodiment, $R_2$ is ethoxy. In another embodiment, $R_2$ is $OR_M$. In another embodiment, $R_2$ is $NR_{10}R_{11}$.

In one embodiment, $R_3$ is selected from H, $(C_1-C_6)$alkoxy, $OR_{10}$, or $NR_{10}R_{11}$. In another embodiment, $R_3$ is H, $(C_1-C_6)$alkoxy or hydroxyl. In another embodiment, $R_3$ is H or $(C_1-C_6)$alkoxy. In another embodiment, $R_3$ is H or hydroxyl. In another embodiment, $R_3$ is $(C_1-C_6)$alkoxy or hydroxyl. In another embodiment, $R_3$ is H, methoxy, ethoxy, propoxy or hydroxyl. In another embodiment, $R_3$ is H, methoxy or ethoxy. In another embodiment, $R_3$ is H, methoxy or propoxy. In another embodiment, $R_3$ is H, methoxy or hydroxyl. In another embodiment, $R_3$ is methoxy, ethoxy or propoxy. In another embodiment, $R_3$ is methoxy, ethoxy or hydroxyl. In another embodiment, $R_3$ is ethoxy, propoxy or hydroxyl. In another embodiment, $R_3$ is H or methoxy. In another embodiment, $R_3$ is H or ethoxy. In another embodiment, $R_3$ is H or propoxy. In another embodiment, $R_3$ is H or hydroxyl. In another embodiment, $R_3$ is methoxy or ethoxy. In another embodiment, $R_3$ is methoxy or propoxy. In another embodiment, $R_3$ is methoxy or hydroxyl. In another embodiment, $R_3$ is ethoxy or propoxy. In another embodiment, $R_3$ is ethoxy or hydroxyl. In another embodiment, $R_3$ is propoxy or hydroxyl. In another embodiment, $R_3$ is H. In another embodiment, $R_3$ is $(C_1-C_6)$alkoxy. In another embodiment, $R_3$ is methoxy. In another embodiment, $R_3$ is ethoxy. In another embodiment, $R_3$ is $OR_{10}$. In another embodiment, $R_3$ is hydroxyl. In another embodiment, $R_3$ is $NR_{10}R_{11}$.

In one embodiment, $R_4$ is H, $(C_1-C_6)$alkoxy, halo, $OR_{10}$, or $NR_{10}R_{11}$, or $R_4$ and $R_5$ are taken together with the carbons to which they are attached to form a 1,3-dioxolo ring. In another embodiment, $R_4$ is $(C_1-C_6)$alkoxy, halo or $OR_{10}$, or $R_4$ and $R_5$ are taken together with the carbons to which they are attached to form a 1,3-dioxolo ring. In another embodiment, $R_4$ is $(C_1-C_6)$alkoxy, halo or $OR_{10}$. In another embodiment, $R_4$ is $(C_1-C_6)$alkoxy or halo, or $R_4$ and $R_5$ are taken together with the carbons to which they are attached to form a 1,3-dioxolo ring. In another embodiment, $R_4$ is halo or $OR_{10}$, or $R_4$ and $R_5$ are taken together with the carbons to which they are attached to form a 1,3-dioxolo ring. In another embodiment, $R_4$ is $(C_1-C_6)$alkoxy or halo. In another embodiment, $R_4$ is $(C_1-C_6)$alkoxy or $OR_{10}$. In another embodiment, $R_4$ is $(C_1-C_6)$alkoxy or $NR_{10}R_{11}$. In another embodiment, $R_4$ is $(C_1-C_6)$alkoxy or $OR_{10}$. In another embodiment, $R_4$ is $(C_1-C_6)$alkoxy, or $R_4$ and $R_5$ are taken together with the carbons to which they are attached to form a 1,3-dioxolo ring. In another embodiment, $R_4$ is halo or $OR_{10}$. In another embodiment, $R_4$ is halo or $R_4$ and $R_5$ are taken together with the carbons to which they are attached to form a 1,3-dioxolo ring. In another embodiment, $R_4$ is $OR_{10}$, or $R_4$ and $R_5$ are taken together with the carbons to which they are attached to form a 1,3-dioxolo ring. In another embodiment, $R_4$ is methoxy, ethoxy, propoxy, bromo, fluoro, chloro, hydroxyl, or O-Protecting Group, or $R_4$ and $R_5$ are taken together with the carbons to which they are attached to form a 1,3-dioxolo ring. In another embodiment, $R_4$ is methoxy, bromo, hydroxyl, or O-Protecting Group, or $R_4$ and $R_5$ are taken together with the carbons to which they are attached to form a 1,3-dioxolo ring. In another embodiment, $R_4$ is methoxy. In another embodiment, $R_4$ is bromo. In another embodiment, $R_4$ is hydroxyl. In another embodiment, $R_4$ is O-Protecting Group.

In one embodiment, $R_5$ is H. In another embodiment, $R_4$ and $R_5$ are taken together with the carbons to which they are attached to form a 1,3-dioxolo ring.

In one embodiment, $R_6$ is H. In another embodiment, $R_6$ is $(C_1-C_6)$alkoxy. In another embodiment, $R_6$ is H, methoxy, ethoxy or propoxy. In another embodiment, $R_6$ is H, methoxy or ethoxy. In another embodiment, $R_6$ is H, methoxy or propoxy. In another embodiment, $R_6$ is methoxy, ethoxy or propoxy. In another embodiment, $R_6$ is H or methoxy. In another embodiment, $R_6$ is H or ethoxy. In another embodiment, $R_6$ is H or propoxy. In another embodiment, $R_6$ is methoxy or ethoxy. In another embodiment, $R_6$ is methoxy or propoxy. In another embodiment, $R_6$ is ethoxy or propoxy. In another embodiment, $R_6$ is methoxy. In another embodiment, $R_6$ is ethoxy.

In one embodiment, $R_7$ is methoxy, ethoxy or propoxy. In another embodiment, $R_7$ is methoxy or ethoxy. In another embodiment, $R_7$ is methoxy or propoxy. In another embodiment, $R_7$ is ethoxy or propoxy. In another embodiment, $R_7$ is methoxy. In another embodiment, $R_7$ is ethoxy.

In one embodiment, $R_8$ is methoxy, ethoxy or propoxy. In another embodiment, $R_8$ is methoxy or ethoxy. In another embodiment, $R_8$ is methoxy or propoxy. In another embodiment, $R_8$ is ethoxy or propoxy. In another embodiment, $R_8$ is methoxy. In another embodiment, $R_8$ is ethoxy.

In one embodiment, $R_7$ and $R_8$ are taken together with the carbons to which they are attached to form a 1,3-dioxolo ring.

In one embodiment, $R_2$ is selected from H or $(C_1-C_6)$alkoxy; $R_3$ is selected from H, $(C_1-C_6)$alkoxy, hydroxyl, O-Protecting Group, or O-Linker Unit; and $R_4$ is selected from $(C_1-C_6)$alkoxy, halo, hydroxyl, O-Protecting Group, or O-Linker Unit.

In one embodiment, the present disclosure provides a compound of formula (Ib),

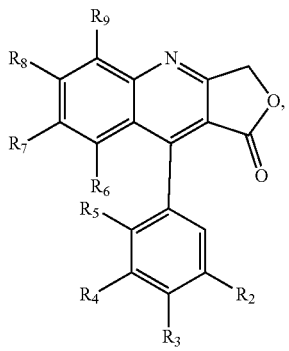

(Ib)

or a pharmaceutically acceptable salt thereof, wherein each of $R_2$, $R_3$, $R_4$, $R_5$, $R_6$, $R_7$, $R_8$ and $R_9$ are as defined above in connection with the compounds of formula (I).

In one embodiment, $R_2$ is selected from H, $(C_1-C_6)$alkoxy, $OR_{10}$, or $NR_{10}R_{11}$. In another embodiment, $R_2$ is H or $(C_1-C_6)$alkoxy. In another embodiment, $R_2$ is H, methoxy, ethoxy or propoxy. In another embodiment, $R_2$ is H, methoxy or ethoxy. In another embodiment, $R_2$ is H, methoxy or propoxy. In another embodiment, $R_2$ is methoxy, ethoxy or propoxy. In another embodiment, $R_2$ is H or methoxy. In another embodiment, $R_2$ is H or ethoxy. In another embodiment, $R_2$ is H or propoxy. In another embodiment, $R_2$ is methoxy or ethoxy. In another embodiment, $R_2$ is methoxy or propoxy. In another embodiment, $R_2$ is ethoxy or propoxy. In another embodiment, $R_2$ is H. In another embodiment, $R_2$ is $(C_1-C_6)$alkoxy. In another embodiment, $R_2$ is methoxy. In another embodiment, $R_2$ is ethoxy. In another embodiment, $R_2$ is $OR_{10}$. In another embodiment, $R_2$ is $NR_{10}R_{11}$.

In one embodiment, $R_3$ is selected from H, $(C_1-C_6)$alkoxy, $OR_{10}$, or $NR_{10}R_{11}$. In another embodiment, $R_3$ is H, $(C_1-C_6)$alkoxy or hydroxyl. In another embodiment, $R_3$ is H or $(C_1-C_6)$alkoxy. In another embodiment, $R_3$ is H or hydroxyl. In another embodiment, $R_3$ is $(C_1-C_6)$alkoxy or hydroxyl. In another embodiment, $R_3$ is H, methoxy, ethoxy, propoxy or hydroxyl. In another embodiment, $R_3$ is H, methoxy or ethoxy. In another embodiment, $R_3$ is H, methoxy or propoxy. In another embodiment, $R_3$ is H, methoxy or hydroxyl. In another embodiment, $R_3$ is methoxy, ethoxy or propoxy. In another embodiment, $R_3$ is methoxy, ethoxy or hydroxyl. In another embodiment, $R_3$ is ethoxy, propoxy or hydroxyl. In another embodiment, $R_3$ is H or methoxy. In another embodiment, $R_3$ is H or ethoxy. In another embodiment, $R_3$ is H or propoxy. In another embodiment, $R_3$ is H or hydroxyl. In another embodiment, $R_3$ is methoxy or ethoxy. In another embodiment, $R_3$ is methoxy or propoxy. In another embodiment, $R_3$ is methoxy or hydroxyl. In another embodiment, $R_3$ is ethoxy or propoxy. In another embodiment, $R_3$ is ethoxy or hydroxyl. In another embodiment, $R_3$ is propoxy or hydroxyl. In another embodiment, $R_3$ is H. In another embodiment, $R_3$ is $(C_1-C_6)$alkoxy. In another embodiment, $R_3$ is methoxy. In another embodiment, $R_3$ is ethoxy. In another embodiment, $R_3$ is $OR_{10}$. In another embodiment, $R_3$ is hydroxyl. In another embodiment, $R_3$ is $NR_{10}R_{11}$.

In one embodiment, $R_4$ is H, $(C_1-C_6)$alkoxy, halo, $OR_{10}$, or $NR_{10}R_{11}$, or $R_4$ and $R_5$ are taken together with the carbons to which they are attached to form a 1,3-dioxolo ring. In another embodiment, $R_4$ is $(C_1-C_6)$alkoxy, halo or $OR_{10}$, or $R_4$ and $R_5$ are taken together with the carbons to which they are attached to form a 1,3-dioxolo ring. In another embodiment, $R_4$ is $(C_1-C_6)$alkoxy, halo or $OR_{10}$. In another embodiment, $R_4$ is $(C_1-C_6)$alkoxy or halo, or $R_4$ and $R_5$ are taken together with the carbons to which they are attached to form a 1,3-dioxolo ring. In another embodiment, $R_4$ is halo or $OR_{10}$, or $R_4$ and $R_5$ are taken together with the carbons to which they are attached to form a 1,3-dioxolo ring. In another embodiment, $R_4$ is $(C_1-C_6)$alkoxy or halo. In another embodiment, $R_4$ is $(C_1-C_6)$alkoxy or $OR_{10}$. In another embodiment, $R_4$ is $(C_1-C_6)$alkoxy or $NR_{10}R_{11}$. In another embodiment, $R_4$ is $(C_1-C_6)$alkoxy or $OR_{10}$. In another embodiment, $R_4$ is $(C_1-C_6)$alkoxy, or $R_4$ and $R_5$ are taken together with the carbons to which they are attached to form a 1,3-dioxolo ring. In another embodiment, $R_4$ is halo or $OR_{10}$. In another embodiment, $R_4$ is halo or $R_4$ and $R_5$ are taken together with the carbons to which they are attached to form a 1,3-dioxolo ring. In another embodiment, $R_4$ is $OR_{10}$, or $R_4$ and $R_5$ are taken together with the carbons to which they are attached to form a 1,3-dioxolo ring. In another embodiment, $R_4$ is methoxy, ethoxy, propoxy, bromo, fluoro, chloro, hydroxyl, or O-Protecting Group, or $R_4$ and $R_5$ are taken together with the carbons to which they are attached to form a 1,3-dioxolo ring. In another embodiment, $R_4$ is methoxy, bromo, hydroxyl, or O-Protecting Group, or $R_4$ and $R_5$ are taken together with the carbons to which they are attached to form a 1,3-dioxolo ring. In another embodiment, $R_4$ is methoxy. In another embodiment, $R_4$ is bromo. In another embodiment, $R_4$ is hydroxyl. In another embodiment, $R_4$ is O-Protecting Group.

In one embodiment, $R_5$ is H. In another embodiment, $R_4$ and $R_5$ are taken together with the carbons to which they are attached to form a 1,3-dioxolo ring.

In one embodiment, $R_6$ is H. In another embodiment, $R_6$ is $(C_1-C_6)$alkoxy. In another embodiment, $R_6$ is H, methoxy, ethoxy or propoxy. In another embodiment, $R_6$ is H, methoxy or ethoxy. In another embodiment, $R_6$ is H, methoxy or propoxy. In another embodiment, $R_6$ is methoxy, ethoxy or propoxy. In another embodiment, $R_6$ is H or methoxy. In another embodiment, $R_6$ is H or ethoxy. In another embodiment, $R_6$ is H or propoxy. In another embodiment, $R_6$ is methoxy or ethoxy. In another embodiment, $R_6$ is methoxy or propoxy. In another embodiment, $R_6$ is ethoxy or propoxy. In another embodiment, $R_6$ is methoxy. In another embodiment, $R_6$ is ethoxy.

In one embodiment, $R_7$ is methoxy, ethoxy or propoxy. In another embodiment, $R_7$ is methoxy or ethoxy. In another embodiment, $R_7$ is methoxy or propoxy. In another embodiment, $R_7$ is ethoxy or propoxy. In another embodiment, $R_7$ is methoxy. In another embodiment, $R_7$ is ethoxy.

In one embodiment, $R_8$ is methoxy, ethoxy or propoxy. In another embodiment, $R_8$ is methoxy or ethoxy. In another embodiment, $R_8$ is methoxy or propoxy. In another embodiment, $R_8$ is ethoxy or propoxy. In another embodiment, $R_8$ is methoxy. In another embodiment, $R_8$ is ethoxy.

In one embodiment, $R_7$ and $R_8$ are taken together with the carbons to which they are attached to form a 1,3-dioxolo ring.

In one embodiment, $R_2$ is selected from H or $(C_1-C_6)$alkoxy; $R_3$ is selected from H, $(C_1-C_6)$alkoxy, hydroxyl, O-Protecting Group, or O-Linker Unit; and $R_4$ is selected from $(C_1-C_6)$alkoxy, halo, hydroxyl, O-Protecting Group, or O-Linker Unit.

Table 1 provides representative compounds of the disclosure.

TABLE 1

| Compound No. | Structure | Name |
|---|---|---|
| 13 | 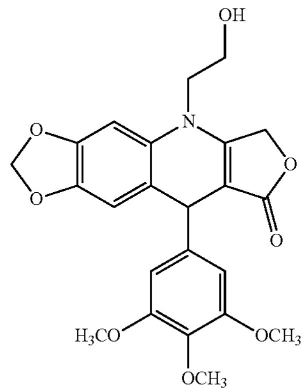 [SMILES: COc1cc(C2C3=C(COC3=O)N(CCO)c3cc4c(cc32)OCO4)cc(OC)c1OC] | 6,7-Methylenedioxy-4-(2-hydroxy-ethyl)-9-(3,4,5-trimethoxyphenyl)-4,9-dihydro-3H-furo[3,4-b]quinolin-1-one |
| 14 | 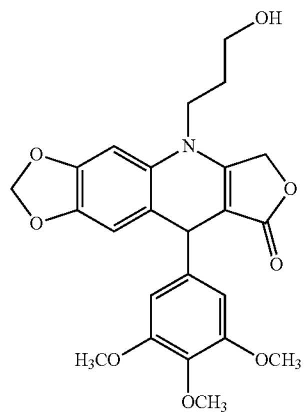 [SMILES: COc1cc(C2C3=C(COC3=O)N(CCCO)c3cc4c(cc32)OCO4)cc(OC)c1OC] | 6,7-Methylenedioxy-4-(3-hydroxy-propyl)-9-(3,4,5-trimethoxyphenyl)-4,9-dihydro-3H-furo[3,4-b]quinolin-1-one |
| 15 | 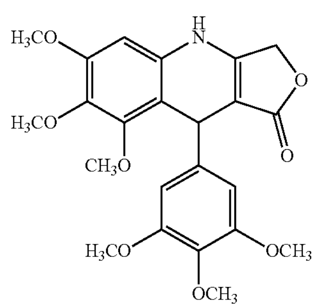 | 6,7,8-Trimethoxy-9-(3,4,5-trimethoxyphenyl)-4,9-dihydro-3H-furo[3,4-b]quinolin-1-one |
| 15a | 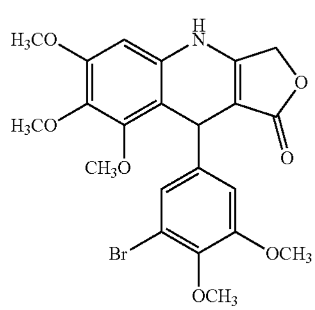 | 6,7,8-Trimethoxy-9-(3-bromo-4,5-trimethoxyphenyl)-4,9-dihydro-3H-furo[3,4-b]quinolin-1-one |

TABLE 1-continued

| Compound No. | Structure | Name |
| --- | --- | --- |
| 15b | 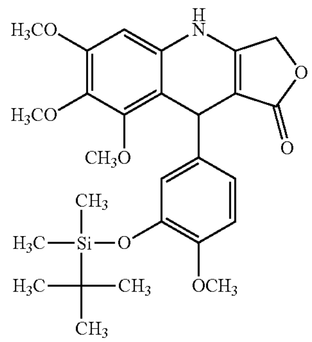 | 6,7,8-Trimethoxy-9-(3-OTBDMS-4-methoxyphenyl)-4,9-dihydro-3H-furo[3,4-b]quinolin-1-one |
| 15c | 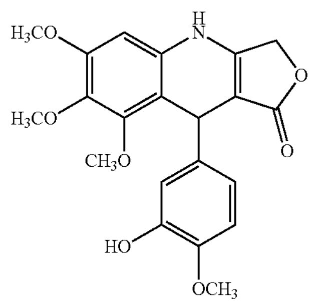 | 6,7,8-Trimethoxy-9-(3-hydroxy-4-methoxyphenyl)-4,9-dihydro-3H-furo[3,4-b]quinolin-1-one |
| 15d | 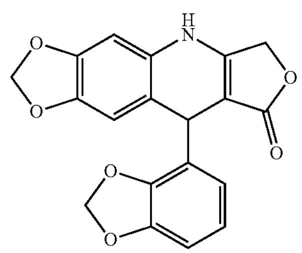 [SMILES: O=C1OCC2=C1C(c1cccc3c1OCO3)c1cc3c(cc1N2)OCO3] | 6,7-Methylenedioxy-9-(2,3-methylenedioxyphenyl)-4,9-dihydro-3H-furo[3,4-b]quinolin-1-one |
| 15e | 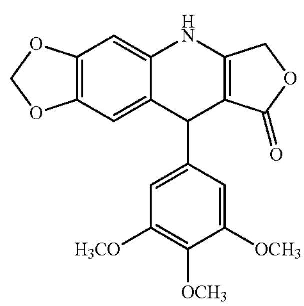 [SMILES: COc1cc(C2C3=C(COC3=O)Nc3cc4c(cc32)OCO4)cc(OC)c1OC] | 6,7-Methylenedioxy-9-(3,4,5-trimethoxyphenyl)-4,9-dihydro-3H-furo[3,4-b]quinolin-1-one |
| 15f | 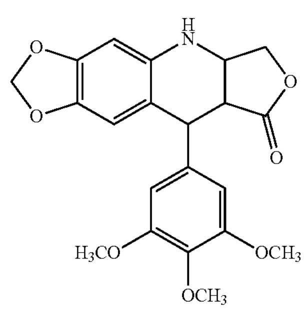 [SMILES: COc1cc(C2c3cc4c(cc3NC3COC(=O)C32)OCO4)cc(OC)c1OC] | 6,7-Dimethoxy-9-(3,4,5-trimethoxyphenyl)-3H-furo[3,4-b]quinolin-1-one |

TABLE 1-continued

| Compound No. | Structure | Name |
|---|---|---|
| 16 | 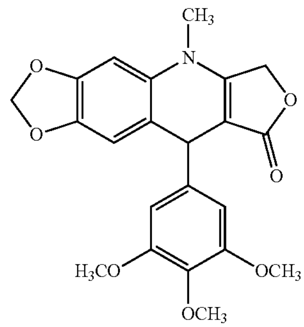 [SMILES: COc1cc(C2C3=C(COC3=O)N(C)c3cc4c(cc32)OCO4)cc(OC)c1OC] | 6,7-Methylenedioxy-4-methyl-9-(3,4,5-trimethoxyphenyl)-4,9-dihydro-3H-furo[3,4-b]quinolin-1-one |
| 17 | 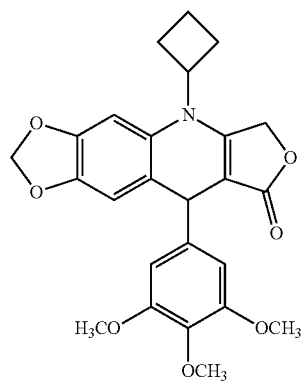 [SMILES: COc1cc(C2C3=C(COC3=O)N(C3CCC3)c3cc4c(cc32)OCO4)cc(OC)c1OC] | 6,7-Methylenedioxy-4-(cyclobutyl)-9-(3,4,5-trimethoxyphenyl)-4,9-dihydro-3H-furo[3,4-b]quinolin-1-one |
| 18 | 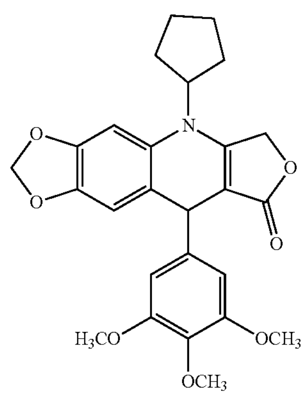 [SMILES: COc1cc(C2C3=C(COC3=O)N(C3CCCC3)c3cc4c(cc32)OCO4)cc(OC)c1OC] | 6,7-Methylenedioxy-4-(cyclopentyl)-9-(3,4,5-trimethoxyphenyl)-4,9-dihydro-3H-furo[3,4-b]quinolin-1-one |
| 19 | 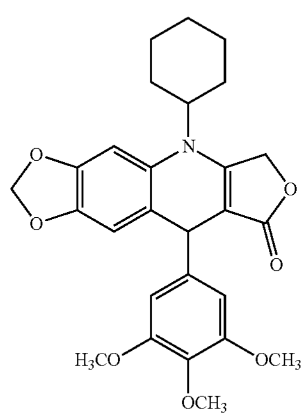 [SMILES: COc1cc(C2C3=C(COC3=O)N(C3CCCCC3)c3cc4c(cc32)OCO4)cc(OC)c1OC] | 6,7-Methylenedioxy-4-(cyclohexyl)-9-(3,4,5-trimethoxyphenyl)-4,9-dihydro-3H-furo[3,4-b]quinolin-1-one |

TABLE 1-continued
| Compound No. | Structure | Name |
|---|---|---|
| 20 | 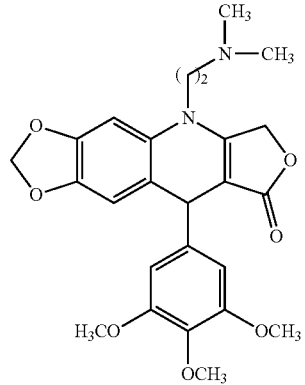 | 6,7-Methylenedioxy-4-(2-dimethyamino-ethyl)-9-(3,4,5-trimethoxyphenyl)-4,9-dihydro-3H-furo[3,4-b]quinolin-1-one |
| 21 | 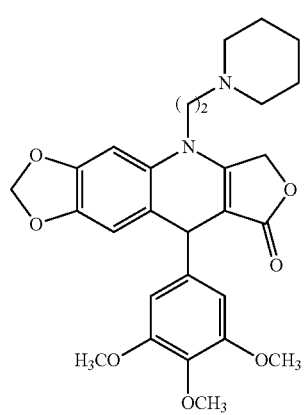 | 6,7-Methylenedioxy-4-(2-piperidin-1-yl-ethyl)-9-(3,4,5-trimethoxyphenyl)-4,9-dihydro-3H-furo[3,4-b]quinolin-1-one |
| 22 | 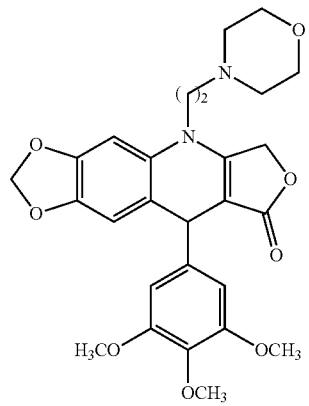 | 6,7-Methylenedioxy-4-(2-morpholin-4-yl-ethyl)-9-(3,4,5-trimethoxyphenyl)-4,9-dihydro-3H-furo[3,4-b]quinolin-1-one |

TABLE 1-continued

| Compound No. | Structure | Name |
|---|---|---|
| 23 | 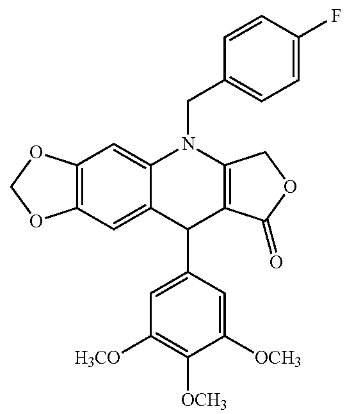 [SMILES: COc1cc(C2C3=C(COC3=O)N(Cc3ccc(F)cc3)c3cc4c(cc32)OCO4)cc(OC)c1OC] | 6,7-Methylenedioxy-4-(4-fluoro-benzyl)-9-(3,4,5-trimethoxyphenyl)-4,9-dihydro-3H-furo[3,4-b]quinolin-1-one |
| 24 | 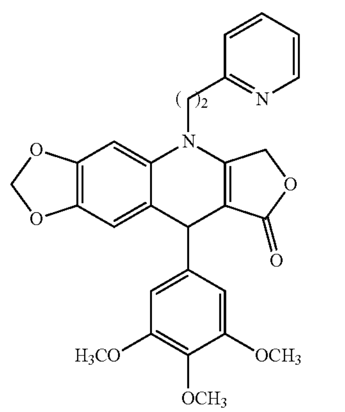 | 6,7-Methylenedioxy-4-(2-pyridin-2-yl-ethyl)-9-(3,4,5-trimethoxyphenyl)-4,9-dihydro-3H-furo[3,4-b]quinolin-1-one |
| 25 | 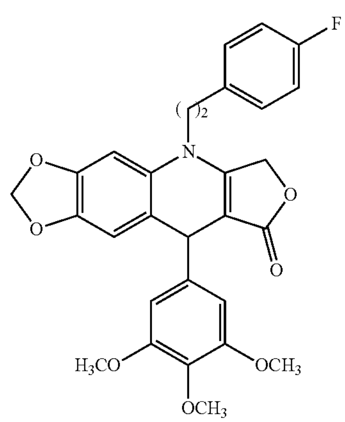 | 6,7-Methylenedioxy-4-[2-(4-fluorophenyl)-ethyl]-9-(3,4,5-trimethoxyphenyl)-4,9-dihydro-3H-furo[3,4-b]quinolin-1-one |

TABLE 1-continued

| Compound No. | Structure | Name |
|---|---|---|
| 26 | 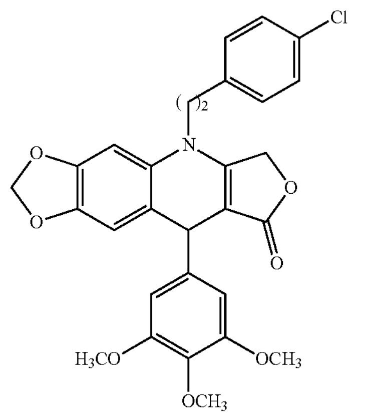 | 6,7-Methylenedioxy-4-[2-(4-chlorophenyl)-ethyl]-9-(3,4,5-trimethoxyphenyl)-4,9-dihydro-3H-furo[3,4-b]quinolin-1-one |
| 27 | 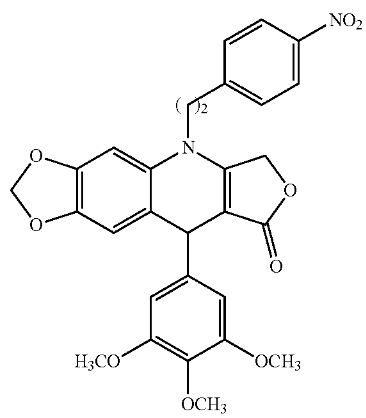 | 6,7-Methylenedioxy-4-[2-(4-nitrophenyl)-ethyl]-9-(3,4,5-trimethoxyphenyl)-4,9-dihydro-3H-furo[3,4-b]quinolin-1-one |
| 28 | 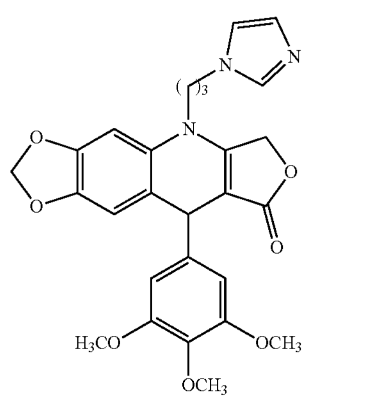 | 6,7-Methylenedioxy-4-(3-imidazol-1-yl-propyl)-9-(3,4,5-trimethoxyphenyl)-4,9-dihydro-3H-furo[3,4-b]quinolin-1-one |
| 29 | 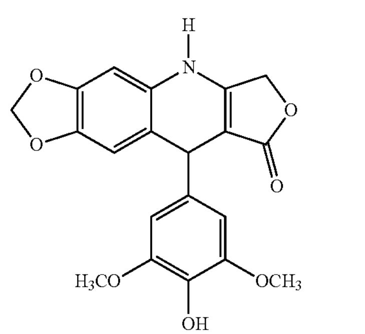 [SMILES: COc1cc(C2C3=C(COC3=O)Nc3cc4c(cc32)OCO4)cc(OC)c1O] | 6,7-Methylenedioxy-9-(4-hydroxy-3,5-dimethoxy-phenyl)-4,9-dihydro-3H-furo[3,4-b]quinolin-1-one |

TABLE 1-continued

| Compound No. | Structure | Name |
|---|---|---|
| 30 | 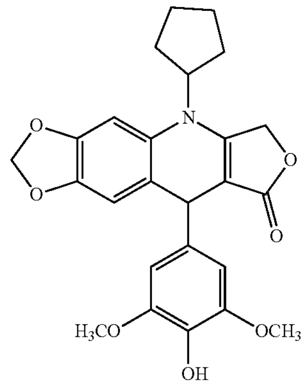 [SMILES: COc1cc(C2C3=C(COC3=O)N(C3CCCC3)c3cc4c(cc32)OCO4)cc(OC)c1O] | 6,7-Methylenedioxy-4-(cyclopentyl)-9-(4-hydroxy-3,5-dimethoxy-phenyl)-4,9-dihydro-3H-furo[3,4-b]quinolin-1-one |
| 31 | 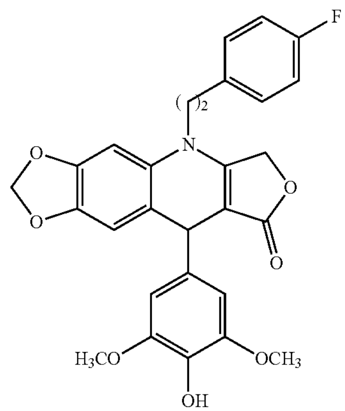 | 6,7-Methylenedioxy-4-[2-(4-fluorophenyl)-ethyl]-9-(4-hydroxy-3,5-dimethoxy-phenyl)-4,9-dihydro-3H-furo[3,4-b]quinolin-1-one |
| 32 | 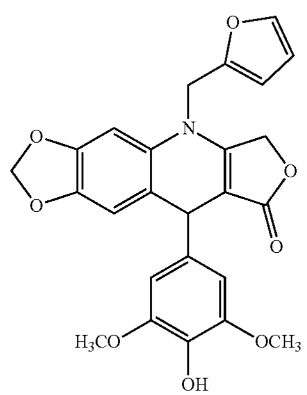 [SMILES: COc1cc(C2C3=C(COC3=O)N(Cc3ccco3)c3cc4c(cc32)OCO4)cc(OC)c1O] | 6,7-Methylenedioxy-4-(furan-2-ylmethyl)-9-(4-hydroxy-3,5-dimethoxy-phenyl)-4,9-dihydro-3H-furo[3,4-b]quinolin-1-one |

In one or more embodiments, a compound of Table 1 is utilized as a pharmaceutically acceptable salt thereof.

In one embodiment, the compound is selected from:

6,7-Methylenedioxy-9-(2,3-methylenedioxyphenyl)-4,9-dihydro-3H-furo[3,4-b]quinolin-1-one (compound 15d);

6,7-Methylenedioxy-9-(3,4,5-trimethoxyphenyl)-4,9-dihydro-3H-furo[3,4-b]quinolin-1-one (compound 15e);

6,7-Methylenedioxy-4-methyl-9-(3,4,5-trimethoxyphenyl)-4,9-dihydro-3H-furo[3,4-b]quinolin-1-one (compound 16);

6,7-Methylenedioxy-4-(cyclobutyl)-9-(3,4,5-trimethoxyphenyl)-4,9-dihydro-3H-furo[3,4-b]quinolin-1-one (compound 17);

6,7-Methylenedioxy-4-(cyclopentyl)-9-(3,4,5-trimethoxyphenyl)-4,9-dihydro-3H-furo[3,4-b]quinolin-1-one (compound 18);

6,7-Methylenedioxy-4-(cyclohexyl)-9-(3,4,5-trimethoxyphenyl)-4,9-dihydro-3H-furo[3,4-b]quinolin-1-one (compound 19);

6,7-Methylenedioxy-4-(4-fluoro-benzyl)-9-(3,4,5-trimethoxyphenyl)-4,9-dihydro-3H-furo[3,4-b]quinolin-1-one (compound 23); or 6,7-Methylenedioxy-9-(4-hydroxy-3,5-dimethoxy-phenyl)-4,9-dihydro-3H-furo[3,4-b]quinolin-1-one (compound 29);

and a pharmaceutically acceptable salt thereof.

In one embodiment, the compound is selected from:

6,7-Methylenedioxy-4-methyl-9-(3,4,5-trimethoxyphenyl)-4,9-dihydro-3H-furo[3,4-b]quinolin-1-one (compound 16);

43

6,7-Methylenedioxy-4-(cyclobutyl)-9-(3,4,5-trimethoxy-phenyl)-4,9-dihydro-3H-furo[3,4-b]quinolin-1-one (compound 17);

6,7-Methylenedioxy-4-(cyclopentyl)-9-(3,4,5-trimethoxy-phenyl)-4,9-dihydro-3H-furo[3,4-b]quinolin-1-one (compound 18);

6,7-Methylenedioxy-4-(cyclohexyl)-9-(3,4,5-trimethoxy-phenyl)-4,9-dihydro-3H-furo[3,4-b]quinolin-1-one (compound 19);

6,7-Methylenedioxy-4-(4-fluoro-benzyl)-9-(3,4,5-trimethoxyphenyl)-4,9-dihydro-3H-furo[3,4-b]quinolin-1-one (compound 23); or 6,7-Methylenedioxy-9-(4-hydroxy-3,5-dimethoxy-phenyl)-4,9-dihydro-3H-furo[3,4-b]quinolin-1-one (compound 29);

and a pharmaceutically acceptable salt thereof

In one embodiment, the compound is selected from:

6,7-Methylenedioxy-9-(2,3-methylenedioxyphenyl)-4,9-dihydro-3H-furo[3,4-b]quinolin-1-one (compound 15d); or 6,7-Methylenedioxy-9-(3,4,5-trimethoxyphenyl)-4,9-dihydro-3H-furo[3,4-b]quinolin-1-one (compound 15e);

and a pharmaceutically acceptable salt thereof.

In one embodiment, the compound is conjugated to a monoclonal antibody and the precursor compound is selected from:

6,7-Methylenedioxy-9-(2,3-methylenedioxyphenyl)-4,9-dihydro-3H-furo[3,4-b]quinolin-1-one (compound 15d); or 6,7-Methylenedioxy-9-(3,4,5-trimethoxyphenyl)-4,9-dihydro-3H-furo[3,4-b]quinolin-1-one (compound 15e);

and a pharmaceutically acceptable salt thereof.

The compounds of this disclosure may be prepared by methods known to those skilled in the art, methods of Schemes 1 through 3, or the synthetic Examples set forth below.

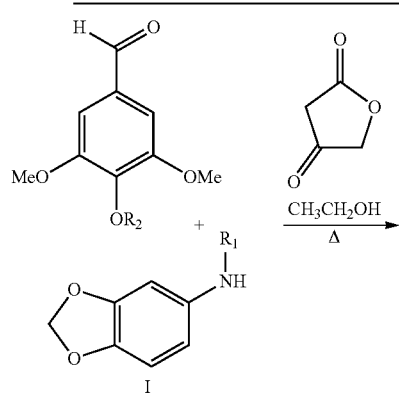

Scheme 1. Efficient Synthethis of 4-Aza-2,3-didehydro-4-deoxypodophyllotoxins

44

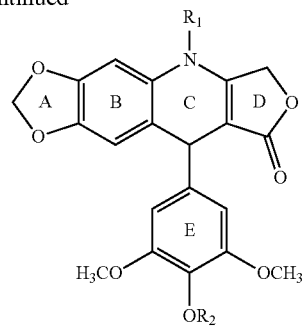

II
$R_2 = CH_3$, 13, 14, 16-28
$R_2 = H$, 29-32

| substrate, I | $R_1$ | product, II | Yield (%) |
|---|---|---|---|
| 12 | ~~~OH | 13 | 59 |
| 12a | ~~~OH | 14 | 38 |
| I | $CH_3$ | 16 | 53 |
| 17a | cyclobutyl-CH2- | 17 | 83 |
| 18a | cyclopentyl-CH2- | 18 | 54 |
| 19a | cyclohexyl-CH2- | 19 | 43 |
| 20a | -CH2CH2N(CH3)2 | 20 | 52 |
| 21a | -CH2CH2CH2-piperidinyl | 21 | 60 |
| 22a | -CH2CH2CH2-morpholinyl | 22 | 68 |
| 23a | 4-F-C6H4-CH2- | 23 | 46 |
| 24a | -(CH2)2-2-pyridyl | 24 | 39 |
| 25a | -(CH2)2-4-F-C6H4- | 25 | 31 |

-continued

| substrate, I | R₁ | product, II | Yield (%) |
|---|---|---|---|
| 26a | (CH₂)₂-C₆H₄-Cl (4-chlorophenethyl) | 26 | 30 |
| 27a | (CH₂)₂-C₆H₄-NO (4-nitrosophenethyl) | 27 | 24 |
| 28a | (CH₂)₃-imidazolyl | 28 | 10 |
| I | H | 29 | 87 |
| 18a | cyclopentylmethyl | 30 | 74 |
| 25a | (CH₂)₂-C₆H₄-F (4-fluorophenethyl) | 31 | 75 |
| 32a | (CH₂)-furyl | 32 | 85 |

Initial attempts to directly add substitutions to the N-4-position of the 4-aza-2,3-didehydro-4-deoxypodophyllotoxin skeleton were unsuccessful. Presumably, this was due to the inactivity of the 4-nitrogen towards electrophilic attack. Indeed, the only reaction explored that allowed the 4-aza-substitution required deprotonation of the nitrogen using butyl lithium and subsequent alkylation with iodomethane to yield the N-methylated product.

Scheme 2. N-Substitution of Anilines

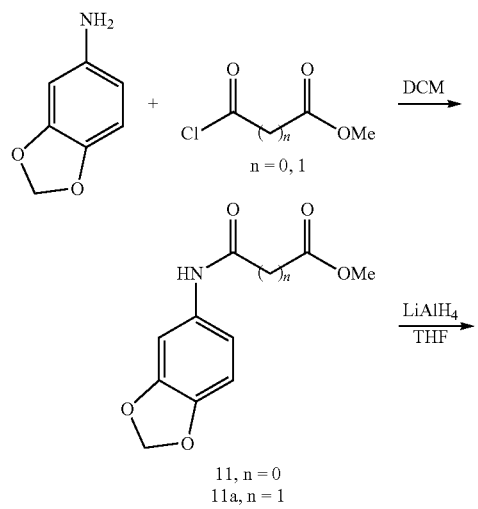

11, n = 0
11a, n = 1

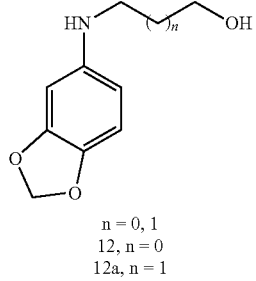

n = 0, 1
12, n = 0
12a, n = 1

Giorgi-Renault's short synthesis can also be utilized with substituted secondary anilines to yield the N-substituted derivatives, albeit in lower yields. N-Derivatives of 3,4-methylenedioxyaniline were an obvious starting point (Scheme 2), and, for example, 4-aza-alkyl derivatives 13[31] and 14 were made utilizing this route.

The prealkylated aniline route was successful in producing 4-N-alkyl derivatives. However, it was hindered by the necessity of reducing the amide intermediates from acid chlorides or imides from aldehydes, and its reliance on the availability of suitable reagents. Reduction of the intermediates (cf., 11 and 11a) often led to complex mixtures of products from incomplete reduction of both the amide and/or ester groups.

The 4-aza substituent syntheses were improved significantly by utilizing phenylboronic acids to arylate amines in the presence of cupric acetate and a tertiary amine base such as triethylamine or pyridine[32] (Scheme 3). The procedure was found useful with a wide variety of reactants. Also, many primary amines and boronic acids are commercially available that can produce a very diverse structural pool of arylated secondary amines. The original report[32] summarizes a variety of substrates that will react by this procedure to form arylamines in yields ranging from 4% to nearly quantitative with the majority of the reactions providing yields in the 50-60% range. Several side reactions were also experienced leading to phenols and biaryl ethers that resulted from the boronic acid reacting with water, either present in solution or generated in situ by triphenylboroxine formation.[32]

Scheme 3. General Reaction Scheme for Aryl Amine Formation

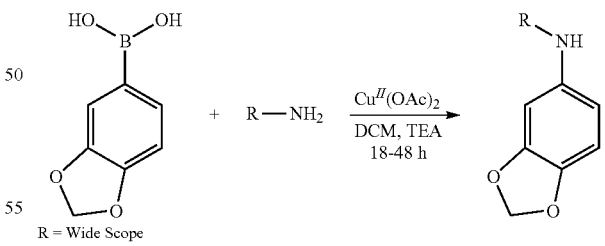

R = Wide Scope

Compound of Formula (I) Conjugates

In some embodiments, the compound of formula (I) is conjugated directly or indirectly to an antibody. In one embodiment, the compound of formula (I) is conjugated directly to an antibody. In another embodiment, the compound of formula (I) is conjugated to an antibody through a Linker Unit. The compound may be conjugated to an antibody through a Linker Unit at $R_1$ in a first embodiment, at $R_2$ in a second embodiment, at $R_3$ in a third embodiment or at $R_4$ in a fourth embodiment. The Linker Unit can operate to provide a suitable release of the compound of formula (I). The preparation of antibody drug conjugates is known to those of skill in the art.

In embodiments in which the compound of formula (I) is conjugated to an antibody through a Linker Unit, the Linker Unit may comprise a cleavable linker in one embodiment and a non-cleavable linker in another embodiment.

In embodiments in which the Linker Unit comprises a cleavable linker, the cleavable linker may be cleaved by methods known in the art. In one embodiment, the cleavable linker may be cleaved by a method selected from the group consisting of glycosidase-induced cleavage, acid-induced cleavage, light-induced cleavage, peptidase-induced cleavage, esterase-induced cleavage, and disulfide bond cleavage. In one embodiment, the cleavage method is selected from the group consisting of glycosidase-induced cleavage, acid-induced cleavage, peptidase-induced cleavage, esterase-induced cleavage, and disulfide bond cleavage. In another embodiment, the cleavage method is selected from the group consisting of glycosidase-induced cleavage, peptidase-induced cleavage, and esterase-induced cleavage. In another embodiment, the cleavage method is selected from glycosidase-induced cleavage or peptidase-induced cleavage. In another embodiment, the cleavage method is selected from glycosidase-induced cleavage or esterase-induced cleavage. In another embodiment, the cleavage method is selected from peptidase-induced cleavage or esterase-induced cleavage.

In embodiments in which the Linker Unit comprises a cleavable linker, the cleavable linker may comprise a glycosidic bond, a hydrazone, a cathepsin-B-cleavable peptide, a disulfide or an ester bond. In one embodiment, the cleavable linker comprises a glycosidic bond, a hydrazone, a cathepsin-B-cleavable peptide, or an ester bond. In one embodiment, the cleavable linker comprises a glycosidic bond, a hydrazone, or a cathepsin-B-cleavable peptide. In one embodiment, the cleavable linker comprises a glycosidic bond, a hydrazone, or an ester bond. In one embodiment, the cleavable linker comprises a glycosidic bond, a cathepsin-B-cleavable peptide, or an ester bond. In one embodiment, the cleavable linker comprises a hydrazone, a cathepsin-B-cleavable peptide, or an ester bond.

In one embodiment, the cleavable linker comprises a glycosidic bond. In one embodiment, the cleavable linker comprises glucuronide.

The compounds of formula (I) may be conjugated to any antibody, e.g., an antibody that binds to a tumor associated antigen. In one embodiment, the antibody used in the antibody drug conjugate of the disclosure is a monoclonal antibody. In another embodiment, the antibody used in the antibody drug conjugate of the disclosure binds at least one of CD19, CD20, CD30, CD33, CD70, BCMA, Glypican-3, Liv-1 and Lewis Y antigen.

When present, the Linker Unit is a bifunctional moiety that can be used to conjugate a compound of formula (I) to an antibody. Such bifuncitional moieties are known in the art and include, but are not limited to, alkyldiyl, an aryldiyl, a heteroaryldiyl, moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide. See, e.g., U.S. Pat. Nos. 6,214,345 and 7,745,394, the contents of both of which are incorporated by reference in their entireties.

In some embodiments, the Linker Unit is as described in U.S. Pat. Nos. 6,214,345 and 7,745,394 and has formula:

$$A_a W_w Y_y,$$

wherein A is a Stretcher Unit,
a is 0 or 1,
each —W— is independently an Amino Acid Unit,
w is an integer ranging from 0 to 12,
Y is a Spacer Unit, and
y is 0, 1 or 2.

The Stretcher Unit (-A-), when present, is capable of linking an antibody to an Amino Acid Unit (—W—). The antibody has a functional group that can form a bond with a functional group of a Stretcher. Useful functional groups that can be present on an antibody, either naturally or via chemical manipulation include, but are not limited to, sulfhydryl, amino, hydroxyl, carboxy, the anomeric hydroxyl group of a carbohydrate, and carboxyl. In one aspect, the antibody functional groups are sulfhydryl and amino. Sulfhydryl groups can be generated by reduction of an intramolecular disulfide bond of an antibody. Alternatively, sulfhydryl groups can be generated by reaction of an amino group of a lysine moiety of an antibody using 2-iminothiolane (Traut's reagent) or another sulfhydryl generating reagent.

The Amino Acid Unit (—W—), when present, links the Stretcher Unit to the Spacer Unit if the Spacer Unit is present, links the Stretcher Unit to the compound of formula (I) if the Spacer Unit is absent, and links the antibody to the compound of formula (I) if the Stretcher Unit and Spacer Unit are absent.

$W_w$— is a dipeptide, tripeptide, tetrapeptide, pentapeptide, hexapeptide, heptapeptide, octapeptide, nonapeptide, decapeptide, undecapeptide or dodecapeptide unit. The Amino Acid may be any amino acid. In some embodiments, the Amino Acid Unit comprises natural amino acids. In other embodiments, the Amino Acid Unit comprises non-natural amino acids.

The Spacer Unit (—Y—), when present, links an Amino Acid Unit to the compound of formula (I) when an Amino Acid Unit is present. Alternately, the Spacer Unit links the Stretcher Unit to the compound of formula (I) when the Amino Acid Unit is absent. The Spacer Unit also links the compound of formula (I) to the antibody when both the Amino Acid Unit and Stretcher Unit are absent.

Suitable Spacer Units include, but are not limited to a glycine-glycine unit; a glycine unit; p-aminobenzyl alcohol (PAB) unit or aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals; spacers that undergo cyclization upon amide bond hydrolysis, such as substituted and unsubstituted 4-aminobutyric acid amides (Rodrigues et al., Chemistry Biology, 1995, 2, 223), appropriately substituted bicyclo[2.2.1] and bicyclo[2.2.2] ring systems (Storm, et al., J. Amer. Chem. Soc., 1972, 94, 5815) and 2-aminophenylpropionic acid amides (Amsberry, et al., J. Org. Chem., 1990, 55, 5867); and a branched bis(hydroxymethyl)styrene (BHMS) unit.

In some embodiments, the Linker Unit comprises a cleavable linker. In some embodiments, the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage. In some embodiments, the cleavable linker comprises a glycosidic bond, a hydrazone, a cathepsin-B-cleavable peptide, a disulfide or an ester bond. In some embodiments, the cleavable linker comprises glucuronide.

In some embodiments, $A_a$ is maleimidocaproyl.

In some embodiments, $W_w$ is Valine-Citrulline.

In some embodiments, $Y_y$ is p-aminobenzyloxycarbonyl.

In some embodiments, $A_a$ is maleimidocaproyl, $W_w$ is Valine-Citrulline and $Y_y$ is p-aminobenzyloxycarbonyl.

In some embodiments, the Linker Unit comprises a monoclonal antibody.

Pharmaceutical Compositions

According to another embodiment, the present disclosure provides a pharmaceutical composition comprising a compound described herein or a pharmaceutically acceptable salt thereof and a pharmaceutically acceptable carrier.

The pharmaceutical composition of the disclosure may be formulated for administration in solid or liquid form, including those adapted for administration by oral, nasal, parenteral, rectal, topical, ocular, inhalation and intra-tumor administration. Parenteral administration includes subcutaneous injections, intravenous, intramuscular or intrasternal injection or infusion techniques. In one embodiment, the compositions are administered parenterally. In another embodiment, the compositions are administered intravenously.

The pharmaceutical composition of the disclosure may be in the form of a liquid, e.g., a solution, emulsion or suspension, pellets, powders, sustained-release formulations, or any other form suitable for use. The pharmaceutical composition may comprise sterile diluents such as water, saline solution, preferably physiological saline, Ringer's solution, isotonic sodium chloride, fixed oils such as synthetic mono- or digylcerides, which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates, phosphates or amino acids; agents for the adjustment of tonicity such as sodium chloride or dextrose; surfactants; preservatives; wetting agents; dispersing agents; suspending agents; stabilizers; solubilizing agents; local anesthetics, e.g., lignocaine; or isotonic agent.

It should be understood that a specific dosage and treatment regimen for any particular patient will depend upon a variety of factors, including the type of patient (e.g., human), the activity of the specific compound employed, the composition employed, the manner of administration, the age, body weight, general health, sex, diet, time of administration, rate of excretion, drug combination, and the judgment of the treating physician and the nature and the severity of the particular disorder being treated. The amount of active ingredients will also depend upon the particular compound in the composition. The amount of active ingredient can be determined by standard clinical techniques. In addition, in vitro or in vivo assays can optionally be employed to help identify optimal dosage ranges.

Preferably, the compositions are formulated so that a dosage of between about 0.01 to about 20 mg/kg body weight/day of the compound of formula (I) can be administered to a patient receiving the composition. In one embodiment, the dosage administered to the patient is between about 0.01 mg/kg and about 10 mg/kg of the patient's body weight. In another embodiment, the dosage administered to the patient is between about 0.1 mg/kg and about 10 mg/kg of the patient's body weight. In yet another embodiment, the dosage administered to the patient is between about 0.1 mg/kg and about 5 mg/kg of the patient's body weight. In yet another embodiment, the dosage administered is between about 0.1 mg/kg and about 3 mg/kg of the patient's body weight. In yet another embodiment, the dosage administered is between about 1 mg/kg and about 3 mg/kg of the patient's body weight.

The pharmaceutical compositions comprise an effective amount of a compound described herein such that a suitable dosage will be obtained. Typically, this amount is at least about 0.01% of a compound by weight of the composition. In a preferred embodiment, pharmaceutical compositions are prepared so that a parenteral dosage unit contains from about 0.01% to about 2% by weight of the compound of the disclosure.

For intravenous administration, the pharmaceutical composition may comprise from about 0.01 to about 100 mg of a compound described herein per kg of the patient's body weight. In one aspect, the composition may include from about 1 to about 100 mg of a compound described herein per kg of the patient's body weight. In another aspect, the amount administered will be in the range from about 0.1 to about 25 mg of a compound described herein per kg of body weight.

The pharmaceutical compositions of the present disclosure may optionally further comprise a second therapeutic agent in a therapeutically effective amount. The second therapeutic agent includes those that are known and those discovered to be effective in the treatment of cancer. In some embodiments, the second therapeutic agent is selected from the group consisting of a tubulin-forming inhibitor, a topoisomerase inhibitor, and a DNA binder.

Methods of Use

The present disclosure also provides methods of using the compounds described herein or pharmaceutical compositions thereof. The compounds and compositions are useful for killing or inhibiting the proliferation of tumor cells or cancer cells. The compounds and compositions are also useful for treating cancer in a patient.

In some embodiments, the present disclosure provides methods of killing or inhibiting the proliferation of tumor cells or cancer cells. In some embodiments, the method comprises contacting the tumor cells or cancer cells with a compound described herein, or a pharmaceutically acceptable salt thereof, in an amount effective to kill or inhibit the proliferation of the tumor cells or cancer cells. In alternate embodiments, the method comprises contacting the tumor cells or cancer cells with a pharmaceutical composition comprising a compound described herein in an amount effective to kill or inhibit the proliferation of the tumor cells or cancer cells.

In some embodiments, the method further comprises contacting the cells with an effective amount of a second therapeutic agent or a pharmaceutical composition thereof. In one embodiment, the second therapeutic agent can be selected from the group consisting of a tubulin-forming inhibitor, a topoisomerase inhibitor, and a DNA binder.

The cells may be contacted with the compound described herein and the second therapeutic agent simultaneously in either the same or different compositions or sequentially in any order. The amounts of compound described herein and the second therapeutic agent and the relative timings of their contact will be selected in order to achieve the desired combined effect.

In another embodiment, the present disclosure provides a method of determining inhibition of cellular proliferation by a compound described herein. The method comprises contacting cells in a cell culture medium with the compound described herein and measuring the cytotoxic activity of the compound, whereby proliferation of the cells is inhibited. In some embodiments, the method further comprises culturing the cells for a period from about 6 hours to about 5 days.

Suitable cell lines are known to those skilled in the art and include those used for evaluating other anti-cancer drugs. Such cell lines include, but are not limited to, P388 (murine lymphocytic leukemia); BXPC-3 (pancreas); MCF-7 (breast); SF-268 (CNS); NCI-H460 (lung); KM20L2 (colon); DU-145 (prostate); 786-O (a renal cell carcinoma); Caki-1 (a renal cell carcinoma); L428 (Hodgkin's disease); UMRC-3 (renal cell carcinoma); LP-1 (human myeloma); and U251 (glioblastoma cell line). In some embodiments, the cells are obtained from a patient having a disease to be treated (e.g., cancer) or from a relevant cell line.

In another embodiment, the present disclosure provides a method of measuring cell viability in the presence of a compound described herein. The method comprises contacting cells in a cell culture medium with the compound of described herein, culturing the cells for a period from about 6 hours to about 5 days, preferably 96 hours; and measuring cell viability. In some embodiments, the cells are obtained from a patient having a disease to be treated (e.g., cancer) or from a relevant cell line.

In another embodiment, the present disclosure provides a method for treating cancer in a patient. In some embodiments, the method comprises administering to the patient a compound described herein, or a pharmaceutically acceptable salt thereof, in an amount effective to treat cancer. In other embodiments, the method comprises administering to the patient a composition comprising a compound described herein in an amount effective to treat cancer.

In some embodiments, the patient receives an additional treatment, such as radiation therapy, surgery, chemotherapy with another chemotherapeutic agent or combinations thereof. In some embodiments, the compound of the disclosure is administered concurrently with the chemotherapeutic agent or with radiation therapy or with surgery. In other embodiments, the chemotherapeutic agent or radiation therapy or surgery is administered or performed prior or subsequent to administration of a compound of the disclosure.

In some embodiments, the method for treating cancer further comprises administering to the patient an effective amount of a second therapeutic agent, e.g., a chemotherapeutic agent. Any one or a combination of the chemotherapeutic agents, such a standard of care chemotherapeutic agent(s), can be administered. In some embodiments, the chemotherapeutic agent may be selected from the group consisting of a tubulin-forming inhibitor, a topoisomerase inhibitor, and a DNA binder.

The compound described herein and the chemotherapeutic agent may be administered simultaneously in either the same or different pharmaceutical composition or sequentially in any order. The amounts of compound described herein and the chemotherapeutic agent and the relative timings of their administration will be selected in order to achieve the desired combined effect.

In another embodiment, the present disclosure provides a method of inhibiting the growth of tumor cells that overexpress a tumor-associated antigen in a patient. In some embodiments, the method comprises administering to the patient a compound described herein conjugated to an antibody that is specific for the tumor-associated antigen, wherein the compound described herein is administered in amount effective to inhibit growth of tumor cells in the patient. In alternate embodiments, the method comprises administering to the patient a pharmaceutical composition comprising a compound described herein conjugated to an antibody that is specific for the tumor-associated antigen, wherein the compound described herein is administered in amount effective to inhibit growth of tumor cells in the patient. The method may optionally further comprises administering to the patient a chemotherapeutic agent, or a pharmaceutical composition thereof, in an amount effective to inhibit the growth of tumor cells in the patient.

In some embodiments, the compound sensitizes the tumor cells to the chemotherapeutic agent.

In some embodiments, the compound induces cell death. In other embodiments, the compound induces apoptosis.

In some embodiments, the tumor cells are associated with a cancer selected from the group consisting of Kaposi's sarcoma, Ewing's sarcoma, Wilms' tumor, rhabdomyosarcoma, testicular cancer, lymphoma, Non-Hodgkin's lymphoma, Hodgkin's lymphoma, glioblastoma multiforme, neuroblastoma, brain tumors, bone cancer, adrenal cortex cancer, endometrium cancer, ovarian cancer, cancer of the soft tissues, gestational trophoblastic tumors, hepatoblastoma, cancer of the lymph system, cancers of the blood and lymph system, multiple myeloma, myelodysplastic syndromes, retinoblastoma, thymoma, bladder cancer, stomach cancer, uterine cancer, leukemia, breast cancer, central nervous system cancer, lung cancer, small cell carcinoma, squamous cell lung carcinoma, non-small cell lung cancer, colon cancer, pancreatic cancer, and prostate cancer.

In some embodiments, the compound described herein is conjugated to an antibody selected from the group consisting of CD19, CD20, CD30, CD33, CD70, BCMA, Glypican-3, Liv-1 and Lewis Y.

Any compound or pharmaceutical composition described herein may be used in the methods of the present disclosure.

In some of the above methods, the compound described herein is administered to a patient in a composition comprising a pharmaceutically acceptable carrier. In some of these embodiments, the composition is administered intravenously. In certain embodiments, the compound is formulated in a unit dosage injectable form.

In preferred embodiments of each of the above methods, the patient is a human.

In an additional embodiment, the present disclosure provides the use of a compound of described herein in the manufacture of a medicament for the treatment of any of the above mentioned cancers. It will be appreciated that a compound described herein and one or more second therapeutic agents may be used in the manufacture of the medicament.

In additional embodiments, the present disclosure provides an article of manufacture comprising a compound described herein, a container, and a package insert or label indicating that the compound can be used to treat cancer characterized by the overexpression of at least one tumor-associated antigen.

The term "package insert" is used to refer to instructions customarily included in commercial packages of therapeutic products that contain information about the indication(s), usage, dosage, administration, contraindications and/or warnings concerning the use of such therapeutic products.

In order that this invention be more fully understood, the following examples are set forth. These examples are for the purpose of illustration only, are applicable to one or more embodiments and are not to be construed as limiting the scope of the invention in any way.

EXAMPLES

General Experimental Procedures. Ether refers to diethyl ether, Ar to argon gas, sgc chromatography to silica gel column chromatography, bac chromatography to basic alumina column chromatography, and rt to room temperature. All solvents were redistilled prior to use. All starting amines, copper II acetate, and 3,4-methylenedioxyphenyl boronic acid were purchased from Sigma-Aldrich Chemical Company. Other reagents were also purchased from either Sigma-Aldrich Chemical Company or Acros Organics.

Reactions were monitored using thin-layer chromatography using Analtech silica gel GHLF Uniplates visualized with long-wave (366 nm) and/or short-wave (254 nm) UV radiation and using a vapor chamber. Solvent extracts of aqueous solutions were washed sequentially with brine and dried over anhydrous magnesium sulfate. Where appropriate, silica gel (70-230 mesh ASTM from Merck) or basic alumina (150 mesh ASTM from Sigma-Aldrich) column chromatography were used for separation of products.

Isolation of natural products was performed employing Sephadex LH-20 gel permeation followed by partition column chromatography with decreasing solvent polarities. Reversed-phase HPLC was performed on a Prepex $C_{18}$ column (250×10 mm) by Phenomenex with a Waters Delta 600 HPLC with dual λ UV detection.

All products were recrystallized at least once before melting point determination. Melting points are uncorrected and were determined using an Electrothermal 9100 apparatus. The $^1$H NMR and $^{13}$C NMR were recorded on Varian Gemini 300 MHz ($^1$H-NMR) and Varian Unity 400 and 500 ($^{13}$C-NMR) instruments using CDCl$_3$, DMSO-d$_6$, or CD$_3$OD with the residual solvent signals as internal references. High-resolution mass spectra were obtained using a JEOL LCMate instrument in either FAB or APCI modes.

Plant Material. The plant branches (34.5 kg) were collected in Gabon, West Africa, in 1979 during the month of April. They were identified by Dr. Arthur S. Barclay from the Medicinal Plant Resources Laboratory, Beltsville Agricultural Research Center (BARC)-East, Beltsville, Md.

A herbarium sample was deposited at the Economic Botany Laboratory, Building 265, BARC-East, Beltsville, Md.

Extraction of Bridelia ferruginea. The final scale-up extraction and isolation was prepared as follows. Branches were less than 1 inch in diameter accompanied by sawdust and were passed through a wood chipper to increase the surface area for solvent extraction. The chipped plant was then divided in half and placed into two 208 L drums. A 1:1 CH$_2$Cl$_2$—CH$_3$OH solution was added (76 L each) to completely cover the material. The extraction was allowed to proceed for one week. To the 1:1 CH$_2$Cl$_2$—CH$_3$OH extraction solvent (30 L) removed from the drums, H$_2$O was added to make a final concentration of 40% v/v H$_2$O. The addition of H$_2$O resulted in a partition forming between CH$_2$Cl$_2$/CH$_3$OH and H$_2$O/CH$_3$OH. The CH$_2$C$_{12}$ layer was removed, and the solvent concentrated in vacuo leaving the crude CH$_2$Cl$_2$ extract. This procedure was repeated twice for each barrel. The crude CH$_2$Cl$_2$ extract was then dissolved in 9:1 CH$_3$OH— H$_2$O, and partitioned with hexanes (2 L×3). Enough H$_2$O was added to the 9:1 CH$_3$OH—H$_2$O to make a 3:2 CH$_3$OH—H$_2$O solution, which was partitioned exhaustively with CH$_2$Cl$_2$ (1.5 L×5). The solvent from the hexane and CH$_2$Cl$_2$ partitions was separately removed and the crude fractions collected. The 9:1 CH$_3$OH—H$_2$O fraction was also collected. The murine P388 lymphocytic leukemia bioassay of the crude fractions showed the CH$_2$Cl$_2$ fraction as the most active (ED$_{50}$=0.02 μg/mL).

The P388 bioactivity-guided fractionation of the CH$_2$Cl$_2$ fraction (80 g), using a series of Sephadex LH-20 column chromatographic separation steps with decreasing solvent polarities (100% CH$_3$OH→3:2 CH$_3$OH—CH$_2$Cl$_2$→4:5:1 n-hexanes-EtOAc-CH$_3$OH), led to several active fractions. A highly P388-active fraction was subjected to semi-preparative HPLC (gradient 25% CH$_3$CN/H$_2$O to 90% CH$_3$CN/H$_2$O) to give deoxypodophyllotoxin (1, 10.2 mg) and isopicrodeoxypodophyllotoxin (2, 10.4 mg) as amorphous powders. Deoxypodophyllotoxin was present in other active fractions, and 400 mg of deoxypodophyllotoxin (1) were obtained. β-Peltatin (3, 121 mg) was crystallized from another active fraction using CH$_3$OH-hexanes to yield a colorless crystalline solid. β-Peltatin-5-O-β-D-glucopyranoside (3a) and the indole derivative neoechinulin (4) were isolated from the CH$_2$Cl$_2$ partition of a 3.24 g sample of crude B. ferruginea extract, employing a series of Sephadex LH-20 column chromatographic separation steps with decreasing solvent polarities. Active fractions were subjected to semi-preparative HPLC. All spectroscopic and physical data obtained for compounds 1-4 were consistent with literature values.[6-11]

N-Benzo[1,3]dioxol-5-yl-oxalamic Acid Methyl Ester (11, n=0) and N-Benzo[1,3]dioxol-5-yl-Malonamic Acid Methyl Ester (11a, n=1). A general procedure for the synthesis of amines 11 and 11a was used as follows, unless otherwise noted: To a stirred solution of CH$_2$Cl$_2$ (100 mL), 3,4-(methylenedioxy) aniline (1 equiv.) and triethylamine (3.0 mL), methyl chlorooxoacetate (n=0, 1 equiv. dropwise) or methyl 3-chloro-3-oxopropionate (n=1, 1 equiv. dropwise) was added. The solution was stirred under Ar until TLC analysis showed that no starting material was present (18 h). Next, the reaction mixture was washed with 1 N HCl (3×), and the CH$_2$Cl$_2$ solution was dried and solvent was removed in vacuo. Further product purification was accomplished using sgc chromatography (8:1 CH$_2$Cl$_2$-EtOAc), followed by recrystallization from hot EtOAc to yield esters 11 or 11a as light yellow needles.

N-Benzo[1,3]dioxol-5-yl-oxalamic Acid Methyl Ester (11, n=0). Light yellow needles, 5.17 g (81%). Recrystallization from hot EtOAc: mp 171-173° C.; $^1$H NMR (CDCl$_3$, 300 MHz) δ 8.77 (1H, bs) 7.34 (1H, d, J=2.1 Hz), 6.94 (1H, dd, J$_1$=8.1 Hz, J$_2$=1.5 Hz) 6.76 (1H, d, J=8.4 Hz), 5.97 (2H, s), 3.95 (3H, s); (+)-HRFABMS m/z 224.0550 [M+H]$^+$ (calcd for C$_{10}$H$_{10}$NO$_5$, 224.0559).

N-Benzo[1,3]dioxol-5-yl-malonamic Acid Methyl Ester (11a, n=1). Light brown needles 6.19 g (84%). Recrystallization from hot EtOAc; mp 165-167° C.; $^1$H NMR (CDCl$_3$, 300 MHz) δ 9.09 (1H, bs), 7.24 (1H, d, J=2.1 Hz), 6.85 (1H, dd, J$_1$=8.1 Hz, J$_2$=2.1 Hz), 6.74 (1H, d, J=8.1 Hz), 5.94 (2H, s), 3.78 (3H, s), 3.45 (2H, s); $^{13}$C NMR (CDCl$_3$, 100 MHz) δ 170.37, 162.61, 147.75, 144.45, 131.62, 113.33, 108.01, 102.91, 101.25, 52.62, 41.12; (+)-HRFABMS m/z 237.9864 [M+H]$^+$ (calcd for C$_{11}$H$_{12}$NO$_5$, 238.0715).

2-(Benzo[1,3]dioxol-5-ylamino)-ethanol (12) and 3-(Benzo[1,3]dioxol-5-ylamino)-propan-1-ol (12a) (I, Scheme 2). General procedure for the synthesis of amines 12 and 12a, unless otherwise noted: To a stirred solution of anhydrous THF, ester 11 or 11a (1 equiv.) and LiAlH$_4$ (1.5 equiv.) was added slowly. The reaction proceeded for 45 min at which point TLC revealed that no starting material was present. The reaction was terminated with EtOAc and H$_2$O and partitioned with EtOAc (3×). The organic layers were combined and extracted with 1 N HCl solution (3×). The latter aqueous extracts were combined, the pH adjusted to 12 with 2 N KOH and extracted with CH$_2$Cl$_2$ (4×). The CH$_2$Cl$_2$ solution was dried and the solvent was removed in vacuo leaving a yellow oil. Isolation of the products was achieved with sgc chromatography (3:1 EtOAc-CH$_3$OH with a gradient to 100% CH₃OH) to give amino alcohols 12 (n=0, 20%, 0.34 g) or 12a (n=1, 43%, 0.41 g).

2-(Benzo[1,3]dioxol-5-ylamino)-ethanol (12). Light yellow oil, 0.34 g (20%); $^1$H NMR (CDCl₃, 300 MHz) δ 6.55 (1H, d, J=8.1 Hz), 6.20 (1H, d, J=2.1 Hz), 6.00 (1H, dd, J₁=8.7 Hz, J₂=2.7 Hz), 5.77 (2H, s), 3.72 (2H, t, J=4.8 Hz), 3.14 (2H, t, J=5.7 Hz); $^{13}$C NMR (CDCl₃, 125 MHz) δ 148.29, 143.51, 140.08, 108.54, 105.12, 100.59, 96.59, 60.99, 47.23; (+)-HRFABMS m/z 182.0818 [M+H]⁺ (calcd for C₉H₁₂NO₃, 182.0817).

3-(Benzo[1,3]dioxol-5-ylamino)-propan-1-ol (12a). Light yellow oil, 0.41 g (43%). $^1$H NMR (CDCl₃, 300 MHz) δ 6.55 (1H, d, J=8.1 Hz), 6.18 (1H, d, J=2.1 Hz), 5.96 (1H, dd, J₁=8.1 Hz, J₂=2.1 Hz), 5.76 (2H, s) 3.71 (2H, t, J=5.7 Hz), 3.12 (2H, t, J=6 Hz), 1.77 (2H, pent., J=6 Hz); $^{13}$C NMR (CDCl₃/CD₃OD, 125 MHz) δ 148.23, 143.97, 139.79, 108.51, 104.93, 100.50, 96.38, 61.38, 43.06, 31.65; (+)-HRAPCIMS m/z 196.0976 [M+H]⁺ (calcd for C₁₀H₁₄NO₃, 196.0974).

Aryl Amines 17a-32a (I, Scheme 1). General procedure for the synthesis of component I (unless otherwise noted): To a stirred solution prepared from CH₂Cl₂ (30 mL), 3,4-methylenedioxy-phenylboronic acid (0.65 g, 0.004 mol) and Cu(II)OAc (1.15 g, 0.008 mol) was stirred for a few minutes then triethylamine (3 mL) and the primary amine (0.004 mol) were added (slowly). The reaction mixture was stirred under Ar for 18-48 h, silica gel or basic alumina was added and the solvent was removed in vacuo leaving a dry packed chromatographic substrate. The product was isolated employing either silica gel column (sgc) or basic alumina column (bac) chromatography to yield the necessary aryl amines, I, which were obtained as brown oils. Maleate salts were prepared from aryl amines in an attempt to obtain pure compounds by crystallization. General procedure: The aryl amine was dissolved in a small amount of ether then maleic acid in ether was added dropwise until a cloudy solution formed. The solvent was removed in vacuo, and the residue was recrystalized from either EtOAc-hexanes or CH₂Cl₂-hexanes. Aryl amines 17a-32a (I) were immediately used to yield dihydroquinolines 17-32 (II).

4-Aza-2,3-didehydropodophyllotoxin Modifications 13,[31]14, 17-32, (II, Scheme 1). General procedure for the synthesis of quinoline II (unless otherwise noted): A stirred solution of aniline component I (1 equiv.) in ethanol (30 mL) was heated to reflux then 3,4,5-trimethoxybenzaldehyde (1 equiv.) and tetronic acid (1 equiv.) were added with continued heating at reflux for 20 min to 1.5 h based upon when a TLC plate showed that a bright blue spot was formed when viewed under UV light. The solvent was removed in vacuo and product (II) was isolated by means of sgc chromatography using appropriate solvent systems. Products were often unstable and underwent degradation as evidenced by the formation of a yellow or yellow/green compound at the baseline when analyzed via TLC. NMR spectroscopy also showed this as an increase of signals in the aliphatic region, not attributable to the desired structure. Unfortunately, late in this research, extenuating circumstances prevented further progress in this SAR study.

6,7-Methylenedioxy-4-(2-hydroxy-ethyl)-9-(3,4,5-trimethoxyphenyl)-4,9-dihydro-3H-furo[3,4-b]quinolin-1-one (13). Purification: recrystallized from CH₂Cl₂—CH₃OH as a colorless powder 0.485 g (59%): mp 271-273° C. [lit.[31]mp 241-243° C.]; $^1$H NMR (DMSO-d₆, 300 MHz) δ 7.15 (1H, d, J=8.2 Hz), 6.40 (1H, d, J=5.1 Hz), 6.27 (2H, s), 5.77 (1H, s), 5.75 (1H, s), 4.83 (1H, s), 4.81 (1H, s), 4.75 (1H, s), 3.96 (2H, m), 3.63 (6H, s), 3.60 (3H, s), 3.50 (2H, m); $^{13}$C NMR (CDCl₃, 100 MHz) δ 172.32, 160.66, 152.79, 146.90, 143.23, 143.05, 135.90, 130.70, 119.43, 109.99, 104.47, 101.35, 96.21, 94.79, 65.78, 59.82, 58.05, 55.75, 48.03, 30.68; (+)-HRFABMS m/z 442.1519 [M+H]⁺ (calcd for C₂₃H₂₃NO₈, 442.1502); anal. C, 62.41; H, 5.58; N, 3.23%, calcd for C₂₃H₂₃NO₈, C, 62.58; H, 5.25; N, 3.17%.

6,7-Methylenedioxy-4-(3-hydroxy-propyl)-9-(3,4,5-trimethoxyphenyl)-4,9-dihydro-3H-furo[3,4-b]quinolin-1-one (14). Purification: sgc chromatography (3:1 EtOAc-hexanes→50:1 EtOAc-CH₃OH) as off-white prisms 0.075 g (38%). Recrystallized from CH₂Cl₂—CH₃OH: mp 269-272° C. (dec); $^1$H NMR (CDCl₃, 400 MHz) δ 6.60 (1H, s), 6.51 (1H, s), 6.34 (2H, s), 5.89 (1H, s), 5.88 (1H, s), 4.95 (1H, d, J=15.6 Hz), 4.89 (1H, s), 4.76 (1H, d, J=15.7 Hz), 3.73 (9H, s), 3.63 (4H, m), 1.95 (2H, m); $^{13}$C NMR (CDCl₃, 100 MHz) δ 173.55, 158.87, 153.06, 147.49, 144.10, 141.90, 136.50, 131.16, 118.95, 110.69, 104.92, 101.54, 96.75, 95.44, 65.50, 60.65, 57.87, 55.95, 42.67, 40.74, 29.73; (+)-HRFABMS m/z 456.1657 [M+H]⁺ (calcd for C₂₄H₂₅NO₈, 456.1658); anal. C, 63.05; H, 5.93; N, 3.18%, calcd for C₂₄H₂₅NO₈, C, 63.29; H, 5.53; N, 3.08%.

Benzo[1,3]dioxol-5-yl-cyclobutyl-amine (17a). Purification: sgc chromatography (1:1 CH₂Cl₂/hexanes) as light brown oil, 0.144 g (19%): $^1$H NMR (CDCl₃, 300 MHz) δ 6.63 (1H, d, J=8.1 Hz), 6.18 (1H, d, J=2.4 Hz), 5.98 (1H, dd, J₁=8.1 Hz, J₂=2.4 Hz), 5.83 (2H, s), 3.82 (1H, m), 3.57 (1H, bs), 2.38 (2H, m), 1.78 (4H, m); $^{13}$C NMR (CDCl₃, 100 MHz) maleate δ 168.91, 148.64, 148.10, 135.04, 128.01, 116.65, 108.75, 104.28, 102.11, 31.57, 26.49, 22.64, 14.10; (+)-HRAPCIMS m/z 192.1021 [M+H]⁺ (calcd for C₁₁H₁₄NO₂, 192.1025).

6,7-Methylenedioxy-4-(cyclobutyl)-9-(3,4,5-trimethoxyphenyl)-4,9-dihydro-3H-furo[3,4-b]quinolin-1-one (17). Purification: sgc chromatography (1:1 CH₂Cl₂-hexanes) as colorless powder 0.284 g (83%). Recrystallized from EtOAc-hexanes: mp 224-226° C.; $^1$H NMR (CDCl₃, 300 MHz) δ 6.60 (1H, s), 6.56 (1H, s), 6.42 (2H, s), 5.95 (1H, s), 5.94 (1H, s), 4.93 (1H, d, J=15.3 Hz), 4.88 (1H, s), 4.60 (1H, d, J=15.3 Hz), 4.37 (1H, pent., J=5.3 Hz), 3.79 (9H, s), 2.69 (1H, m), 2.32 (2H, m), 2.09 (1H, m), 1.87 (2H, m); $^{13}$C NMR (CDCl₃, 125 MHz) δ 172.25, 158.59, 153.18, 147.06, 144.15, 140.90, 136.60, 133.28, 119.46, 109.93, 103.98, 101.56, 100.73, 97.06, 66.04, 60.98, 55.96, 52.66, 40.50, 31.59, 29.36, 14.96; (+)-HRAPCIMS m/z 452.1722 [M+H]⁺ (calcd for C₂₅H₂₅NO₇, 452.1709); anal C, 66.48; H, 5.83; N, 3.18%, calcd for C₂₅H₂₅NO₇, C, 66.51; H, 5.58; N, 3.10%

Benzo[1,3]dioxol-5-yl-cyclopentylamine (18a). Purification: sgc chromatography (10:1 CH₂Cl₂-EtOAc) as light tan oil, 0.314 g (40%): $^1$H NMR (CDCl₃, 300 MHz) δ 6.55 (1H, d, J=8.1 Hz), 6.16 (1H, d, J=2.1 Hz), 5.96 (1H, dd, J₁=8.1 Hz, J₂=2.1 Hz), 5.75 (2H, s), 3.61 (1H, pent., J=5.7 Hz), 3.34 (1H, bs), 1.89 (2H, m), 1.48 (6H, m); $^{13}$C NMR (CDCl₃, 125 MHz) maleate δ 169.80, 148.50, 147.94, 135.83, 129.87, 116.96, 108.55, 104.63, 101.96, 64.70, 29.29, 23.70; (+)-HRFABMS m/z 206.1175 [M+H]⁺ (calcd for C₁₂K₆NO₂, 206.1181).

6,7-Methylenedioxy-4-(cyclopentyl)-9-(3,4,5-trimethoxyphenyl)-4,9-dihydro-3H-furo[3,4-b]quinolin-1-one (18). Purification: sgc chromatography (2:1 EtOAc-CH₃OH) as colorless powder, 0.129 g (54%). Recrystallized from EtOAc-hexanes: mp 221-223° C.; $^1$H NMR (CDCl₃, 500 MHz,) δ 6.64 (1H, s), 6.57 (1H, s), 6.37 (2H, s), 5.93 (1H, s), 5.92 (1H, s), 4.93 (1H, d, J=15 Hz), 4.88 (1H, s), 4.75 (1H, d, J=15 Hz), 4.16 (1H, pent., J=8.5 Hz), 3.76 (6H, s), 3.75 (3H, s), 2.12 (2H, m), 2.00 (4H, m), 1.75 (2H, m); $^{13}$C NMR (CDCl₃, 125 MHz,) δ 172.58, 158.61, 153.12, 146.77, 143.88, 141.42, 136.58, 131.69, 119.89, 110.57, 104.41, 101.54, 99.56, 97.52, 65.85, 60.66, 60.37, 55.94, 40.68, 28.54, 28.21, 24.81, 24.78; (+)-HRAPCIMS m/z 466.1866 [M+H]$^+$ (calcd for $C_{26}H_{27}NO_7$, 466.1866); anal. C, 66.31; H, 6.09; N, 3.01%, calcd for $C_{29}H_{33}NO_8$, C, 66.53; H, 6.35; N, 2.68%.

Benzo[1,3]dioxol-5-yl-cyclohexyl-amine maleate (19a). Purification: sgc chromatography (2:1 hexanes-EtOAc) as light tan oil, 0.184 g (23%): $^1$H NMR (CDCl$_3$, 400 MHz,) δ 7.12 (1H, s), 7.04 (1H, d, J=8 Hz), 6.75 (1H, d, J=8 Hz), 6.31 (2H, s), 5.97 (2H, s), 3.29 (1H, m), 2.03 (2H, bd, J=11.6 Hz), 1.79 (2H, bd, J=10.4 Hz), 1.63 (1H, m), 1.49 (2H, m), 1.19 (3H, m); $^{13}$C NMR (CDCl$_3$, 100 MHz,) maleate δ 169.85, 148.43, 148.04, 135.87, 128.02, 117.57, 108.45, 105.12, 101.97, 62.31, 29.02, 24.87, 24.54; (+)-HRAPCIMS m/z 220.1348 [M+H]$^+$ (calcd for $C_{13}H_{18}NO_2$, 220.1338).

6,7-Methylenedioxy-4-(cyclohexyl)-9-(3,4,5-trimethoxy-phenyl)-4,9-dihydro-3H-furo[3,4-b]quinolin-1-one (19). Purification: sgc chromatography (1:1 EtOAc-hexanes) as light yellow powder 0.132 g (43%). Recrystallized from EtOAc-hexanes: mp 235-237° C.; $^1$H NMR (CDCl$_3$, 500 MHz,) δ 6.67 (1H, s), 6.44 (1H, s), 6.28 (2H, s), 5.82 (1H, d, J=1 Hz), 5.81 (1H, d, J=1 Hz), 4.90 (1H, d, J=15.3 Hz), 4.76 (1H, s), 4.67 (1H, d, J=15.3 Hz), 3.65 (9H, s), 1.83 (4H, m), 1.68 (4H, m), 1.30 (2H, m), 1.11 (1H, m); $^{13}$C NMR (CDCl$_3$, 125 MHz) δ 172.35, 158.01, 153.10, 147.14, 143.91, 141.26, 136.59, 133.51, 119.73, 110.20, 104.38, 101.54, 100.63, 97.31, 66.33, 60.62, 60.25, 55.96, 40.60, 31.63, 30.89, 26.45, 26.20, 25.15; (+)-HRAPCIMS m/z 480.2020 [M+H]$^+$ (calcd for $C_{27}H_{29}NO_7$, 480.2022).

Benzo[1,3]dioxol-5-yl-N,N-dimethyl-ethane-1,2-diamine (20a). Purification: bac chromatography (1:1 CH$_2$Cl$_2$-hexanes) as light tan oil, 0.066 g (10%): $^1$H NMR (CDCl$_3$, 300 MHz) δ 6.56 (1H, d, J=8.1 Hz), 6.17 (1H, d, J=2.4 Hz), 6.75 (1H, dd, J$_1$=8.1 Hz, =2.4 Hz), 5.74 (2H, s), 5.84 (2H, s), 3.07 (2H, t, J$_1$=6.0 Hz), 2.53 (2H, t, J=6.0 Hz), 2.24 (6H, s); $^{13}$C NMR (CDCl$_3$, 125 MHz) δ 148.33, 142.52, 139.85, 108.58, 104.32, 102.33, 100.51, 96.18, 57.90, 44.54; (+)-HRFABMS m/z 209.1297 [M+H]$^+$ (calcd for $C_{11}H_{16}N_2O_2$, 209.1290).

6,7-Methylenedioxy-4-(2-dimethyamino-ethyl)-9-(3,4,5-trimethoxyphenyl)-4,9-dihydro-3H-furo[3,4-b]quinolin-1-one (20). Purification: sgc chromatography (15:1 CH$_2$Cl$_2$/CH$_3$OH) as light brown amorphous solid 0.06 g (52%). Recrystallized from CH$_3$OH: mp 251-254° C.; $^1$H NMR (CDCl$_3$, 300 MHz) δ 6.57 (1H, s), 6.56 (1H, s), 6.40 (2H, s), 5.95 (1H, s), 5.94 (1H, s), 4.96 (1H, s), 4.90 (2H, s), 3.78 (9H, s), 3.60 (2H, m), 2.60 (2H, m), 2.29 (6H, s). $^{13}$C NMR (CDCl$_3$, 125 MHz) δ 172.73, 158.03, 153.09, 147.53, 144.07, 141.72, 136.72, 131.27, 118.80, 110.85, 105.16, 101.57, 97.36, 95.01, 65.33, 60.66, 56.04, 45.85, 40.75; (+)-HRAPCIMS m/z 469.1976 [M+H]$^+$ (calcd for $C_{25}H_{28}N_2O_7$, 469.1975).

Benzo[1,3]dioxol-5-yl-(2-piperidin-1-yl-ethyl)-1,2-diamine (21a). Purification: bac chromatography (5:1 EtOAc-CH$_3$OH) as brown oil, 0.050 g (10%): $^1$H NMR (CDCl$_3$, 300 MHz) δ 6.65 (1H, d, J=8.1 Hz), 6.17 (1H, d, J=2.1 Hz), 5.96 (1H, dd, J$_1$=8.1 Hz, J$_2$=2.1 Hz), 5.75 (2H, s), 4.20 (1H, bs), 2.99 (2H, t, J=6.0 Hz), 2.47 (2H, t, J=6.0 Hz), 2.31 (4H, m), 1.49 (4H, m), 1.36 (2H, m); (+)-HRFABMS m/z 249.1609 [M+H]$^+$ (calcd for $C_{14}H_{20}N_2O_2$, 249.1603).

6,7-Methylenedioxy-4-(2-piperidin-1-yl-ethyl)-9-(3,4,5-trimethoxyphenyl)-4,9-dihydro-3H-furo[3,4-b]quinolin-1-one (21). Purification: sgc chromatography (15:1 CH$_2$Cl$_2$—CH$_3$OH) as light brown amorphous solid, 0.026 g (60%). Recrystallized from EtOAc: mp 170° C. (dec); $^1$H NMR (CDCl$_3$, 300 MHz) δ 6.58 (1H, s), 6.56 (1H, s), 6.39 (2H, s), 5.95 (1H, s), 5.94 (1H, s), 4.98 (1H, s), 4.93 (2H, s), 3.79 (9H, s), 3.65 (2H, m), 2.61 (2H, t, J=6.6 Hz), 2.45 (4H, m), 1.57 (4H, m), 1.43 (2H, m); (+)-HRAPCIMS m/z 509.2293 [M+H]$^+$ (calcd for $C_{28}H_{32}N_2O_7$, 509.2288).

Benzo[1,3]dioxol-5-yl-(2-morpholin-4-yl-ethyl)-1,2-diamine (22a). Purification: sgc chromatography (100% CH$_2$Cl$_2$), light tan oil, 0.11 g (10%); $^1$H NMR (CDCl$_3$, 300 MHz) δ 6.53 (1H, d, J=8.1 Hz), 6.16 (1H, d, J=2.1 Hz), 5.94 (1H, dd, J, =8.1 Hz, J$_2$=2.1 Hz), 5.72 (2H, s), 3.60 (4H, t, J=4.5 Hz), 2.98 (2H, t, J=5.7 Hz), 2.49 (2H, t, J=6 Hz), 2.34 (4H, m); $^{13}$C NMR (CDCl$_3$, 125 MHz) maleate δ 168.55, 148.35, 141.08, 140.74, 134.02, 108.40, 105.10, 100.64, 96.69, 63.57, 55.59, 52.08, 39.11; (+)-HRAPCIMS m/z 251.1392 [M+H]$^+$ (calcd for $C_{13}H_{18}N_2O_3$, 251.1396).

6,7-Methylenedioxy-4-(2-morpholin-4-yl-ethyl)-9-(3,4,5-trimethoxyphenyl)-4,9-dihydro-3H-furo[3,4-b]quinolin-1-one (22). Purification: sgc chromatography (9:1 EtOAc-CH$_3$OH) as colorless crystals, 0.14 g (68%). Recrystallized by slow evaporation from CH$_2$Cl$_2$—CH$_3$OH: mp 186-189° C.; NMR (CDCl$_3$, 300 MHz) δ 6.47 (1H, s), 6.45 (1H, s), 6.27 (2H, s), 5.83 (2H, s), 4.85 (1H, s), 4.80 (2H, bs), 3.67 (9H, s), 3.66 (4H, t, J=4.8 Hz), 3.61 (2H, m), 2.56 (2H, t, J=6 Hz) 2.40 (4H, m); $^{13}$C NMR (CDCl$_3$, 125 MHz) δ 173.28, 158.22, 152.93, 147.52, 144.14, 141.63, 136.58, 130.98, 118.62, 110.75, 105.17, 101.54, 97.19, 94.96, 66.53, 65.43, 60.53, 55.92, 55.70, 53.94, 44.34, 40.49; (+)-HRAPCIMS m/z 511.2082 [M+4]$^+$ (calcd for $C_{27}H_{30}N_2O_8$, 511.2080).

Benzo[1,3]dioxol-5-yl-(4-fluoro-benzyl)-1,2-diamine (23a). Purification: sgc chromatography (3:1 CH$_2$Cl$_2$-hexanes), light tan oil, 0.14 g (14%); $^1$H NMR (CDCl$_3$, 300 MHz) δ 7.22 (2H, m), 6.93 (2H, m) 6.55 (1H, d, J=8.1 Hz), 6.15 (1H, d, J=2.1 Hz), 5.97 (1H, dd, J$_1$=8.1 Hz, J$_2$=2.1 Hz), 5.75 (2H, s), 4.13 (2H, s), 3.70 (1H, bs); $^{13}$C NMR (CDCl$_3$, 125 MHz) maleate δ 172.34, 166.85, 164.87, 151.23, 150.17, 138.09, 135.05, 134.98, 132.60, 129.31, 118.73, 118.60, 118.43, 111.26, 106.49, 104.65, 57.63; (+)-HRFABMS m/z 246.0920 [M+H]$^+$ (calcd for $C_{14}H_{12}NO_2F$, 246.0930).

6,7-Methylenedioxy-4-(4-fluoro-benzyl)-9-(3,4,5-trimethoxyphenyl)-4,9-dihydro-3H-furo[3,4-b]quinolin-1-one (23). Purification: sgc chromatography (2:1 hexanes-EtOAc→4:1 EtOAc-hexanes), light yellow crystals, 0.10 g (46%). Recrystallized from EtOAc and from EtOAc-hexanes: mp 246-247° C.; $^1$H NMR (CDCl$_3$, 300 MHz) δ 7.23 (2H, m), 7.06 (2H, m), 6.58 (1H, s), 6.43 (2H, s), 6.40 (1H, s), 5.90 (1H, d, J=1 Hz), 5.88 (1H, d, J=1 Hz), 5.06 (1H, s), 4.85 (1H, d, J=15 Hz), 4.77 (2H, s), 4.76 (1H, d, J=15 Hz), 3.81 (3H, s) 3.79 (6H, s); $^{13}$C NMR (CDCl$_3$, 125 MHz) δ 172.41, 157.60, 153.21, 147.52, 144.37, 141.43, 136.80, 131.77, 130.66, 127.32, 127.25, 118.45, 116.46, 116.29, 110.75, 105.11, 101.61, 98.26, 95.81, 65.05, 60.74, 56.07, 49.08, 40.71; (+)-HRAPCIMS m/z 506.1613 [M+H]$^+$ (calcd for $C_{28}H_{24}NO_7F$, 506.1615); anal. C, 66.19; H, 5.10; N, 2.81%, calcd for $C_{28}H_{24}NO_7F$: C, 66.53; H, 4.79; N, 2.77%.

Benzo[1,3]dioxol-5-yl-(2-pyridin-2-ylethyl)-1,2-diamine (24a). Purification: sgc chromatography (4:1 EtOAc-CH$_2$Cl$_2$), brown oil, 0.155 g (14%); $^1$H NMR (CDCl$_3$, 300 MHz) δ 8.54 (1H, d, J=4.5 Hz), 7.58 (1H, dd, J$_1$=7.8 Hz, J$_2$=1.8 Hz), 7.15 (2H, m,), 6.65 (1H, d, J=8.7 Hz), 6.25 (1H, d, J=2.1 Hz), 6.07 (1H, dd, J$_1$=8.7 Hz, J$_2$=2.1 Hz), 5.82 (2H, s), 3.93 (1H, bs), 3.45 (2H, t, J=6.6 Hz), 3.05 (2H, t, J=6.6 Hz); $^{13}$C NMR (CDCl$_3$, 125 MHz) maleate δ 169.18, 156.71, 148.67, 145.26, 145.13, 141.35, 135.22, 134.58, 125.78, 123.66, 112.00, 108.78, 101.62, 101.10, 48.98, 31.58; (+)-HRFABMS m/z $C_{14}H_{14}N_2O_2$, 243.1115 [M+H]$^+$ (calcd for $C_{14}H_{14}N_2O_2$, 243.1134).

6,7-Methylenedioxy-4-(2-pyridin-2-yl-ethyl)-9-(3,4,5-trimethoxyphenyl)-4,9-dihydro-3H-furo[3,4-b]quinolin-1-one (24). Purification: sgc chromatography (30:1 EtOAc- CH₃OH), light tan crystals, 0.10 g (39%). Recrystallized from EtOAc-CH₃OH: mp 239-241° C.; ¹H NMR (CDCl₃, 300 MHz) δ 8.57 (1H, d, J=3.9 Hz), 7.56 (1H, dd, J₁=7.5 Hz, J₂=2.1 Hz), 7.17 (1H, m), 7.08 (1H, d, J=7.5 Hz), 6.77 (1H, s), 6.58 (1H, s), 6.37 (1H, s), 5.97 (1H, d, J=1.8 Hz), 5.96 (1H, d, J=1.2 Hz), 4.95 (1H, s), 4.62 (1H, s), 4.61 (1H, s), 4.00 (2H, m), 3.79 (3H, s), 4.77 (6H, s), 3.19 (2H, m); ¹³C NMR (CDCl₃, 125 MHz,) δ 172.76, 157.93, 156.95, 152.95, 149.35, 147.52, 144.05, 141.56, 137.01, 136.65, 131.12, 123.77, 122.29, 118.71, 110.75, 105.21, 101.51, 97.06, 95.26, 65.22, 60.56, 56.01, 45.83, 40.53, 35.55; (+)-HRFABMS m/z 503.1836 [M+H]⁺ (calcd for $C_{28}H_{26}N_2O_7$, 503.1818).

Benzo[1,3]dioxol-5-yl-[2-(4-fluorophenyl)-ethyl]-1,2-diamine (25a). Purification: sgc chromatography (2:1 CH₂Cl₂-hexanes), light tan oil, 0.28 g (27%); ¹H NMR (CDCl₃, 300 MHz) δ 7.06 (2H, m), 6.92 (2H, m), 6.57 (1H, d, J=8.1 Hz), 6.15 (1H, d, J=2.1 Hz), 5.96 (1H, dd, J₁=8.1 Hz, J₂=2.1 Hz), 5.76 (2H, s), 3.33 (1H, bs), 3.23 (2H, t, J=6.9 Hz), 2.78 (2H, t, J=6.9 Hz); ¹³C NMR (CDCl₃, 100 MHz) maleate δ169.67, 148.76, 148.15, 135.47, 130.37, 130.28, 129.99, 116.28, 115.71, 115.50, 108.81, 103.98, 102.13, 53.99, 31.28; (+)-HRFABMS m/z 260.1077 [M+H]⁺ (calcd for $C_{15}H_{14}NO_2F$, 260.1087).

6,7-Methylenedioxy-4-[2-(4-fluorophenyl)-ethyl]-9-(3,4,5-trimethoxyphenyl)-4,9-dihydro-3H-furo[3,4-b]quinolin-1-one (25). Purification: sgc chromatography (4:1 CH₂Cl₂-EtOAc) as light yellow amorphous solid, 0.07 g (31%). Recrystallized from EtOAc: mp 174-177° C.; ¹H NMR (CDCl₃, 300 MHz) δ 7.10 (2H, m), 6.96 (2H, m), 6.66 (1H, s), 6.59 (1H, s), 6.41 (2H, s), 5.98 (1H, s), 5.97 (1H, s), 4.99 (1H, s), 4.35 (1H, d, J=15.2 Hz), 4.30 (1H, d, J=15.2 Hz), 3.79 (9H, s), 3.65 (2H, m), 2.99 (2H, t, J=7.2 Hz); ¹³C NMR (CDCl₃, 125 MHz) δ 172.55, 157.54, 153.16, 147.70, 144.24, 136.97, 133.08, 133.05, 131.18, 130.30, 130.23, 130.14, 118.70, 115.73, 115.64, 111.14, 105.55, 101.69, 97.28, 95.06, 64.98, 60.74, 56.24, 48.35, 40.59, 33.19; (+)-HRFABMS m/z 520.1808 [M+H]⁺ (calcd for $C_{29}H_{26}NO_7F$, 520.1772).

Benzo[1,3]dioxol-5-yl-[2-(4-chlorophenyl)-ethyl]-1,2-diamine (26a). Purification: sgc chromatography (100% CH₂Cl₂), light tan oil, 0.063 g (10%); ¹H NMR (CDCl₃, 300 MHz,) δ 7.26 (2H, m), 7.13 (2H, m), 6.65 (1H, d, J=8.4 Hz), 6.23 (1H, d, J=2.1 Hz), 5.96 (1H, dd, J₁=8.4 Hz, J₂=2.1 Hz), 5.85 (2H, s), 3.44 (1H, bs), 3.31 (2H, t, J=6.6 Hz), 2.86 (2H, t, J=6.6 Hz); ¹³C NMR (CDCl₃, 125 MHz) maleate δ 170.61, 151.44, 150.77, 138.22, 137.38, 135.67, 132.85, 132.78, 131.58, 118.87, 111.50, 106.61, 104.81, 56.37, 34.18; (+)-HRAPCIMS m/z 276.0795 [M+H]⁺ (calcd for $C_{15}H_{14}NO_2{}^{35}Cl$, 276.0791).

6,7-Methylenedioxy-4-[2-(4-chlorophenyl)-ethyl]-9-(3,4,5-trimethoxyphenyl)-4,9-dihydro-3H-furo[3,4-b]quinolin-1-one (26). Purification: sgc chromatography (15:1 CH₂Cl₂—CH₃OH), pale yellow amorphous solid, 0.03 g (30%). Recrystallized from CH₂Cl₂-hexanes: mp 170-173° C.; ¹H NMR (CDCl₃, 300 MHz) δ 7.26 (2H, m), 7.08 (2H, m), 6.65 (1H, s), 6.60 (1H, s), 6.41 (2H, s), 5.98 (1H, s), 5.97 (1H, s), 4.99 (1H, s), 4.39 (1H, d, J=15.4 Hz), 4.33 (1H, d, J=15.4 Hz), 3.80 (9H, s), 3.66 (2H, m), 2.99 (2H, t, J=7.2 Hz); (+)-HRFABMS m/z 538.1442 [M+H]⁺ (calcd for $C_{29}H_{26}NO_7{}^{37}Cl$, 538.1447).

Benzo[1,3]dioxol-5-yl-[2-(4-nitrophenyl)-ethyl]-1,2-diamine (27a). Purification: bac chromatography (100% CH₂Cl₂), light tan oil, 0.166 g (14%); ¹H NMR (CDCl₃, 300 MHz,) δ 8.06 (2H, d, J=9 Hz), 7.26 (2H, d, J=9 Hz), 6.65 (1H, d, J=8.4 Hz), 6.13 (1H, d, J=2.4 Hz), 5.94 (1H, dd, J₁=8.4 Hz, J₂=2.4 Hz), 5.76 (2H, s), 3.29 (2H, t, J=6.9 Hz), 2.90 (2H, t, J=6.9 Hz); (+)-HRAPCIMS m/z 287.1021 [M+H]⁺ (calcd for $C_{15}H_{14}N_2O_4$, 287.1032).

6,7-Methylenedioxy-4-[2-(4-nitrophenyl)-ethyl]-9-(3,4,5-trimethoxyphenyl)-4,9-dihydro-3H-furo[3,4-b]quinolin-1-one (27). Purification: bac chromatography (1:1 CH₂Cl₂-EtOAc), light yellow amorphous solid, 0.076 g (24%). Recrystallized from EtOAc: mp 188-190° C.; ¹H NMR (CDCl₃, 300 MHz) δ 7.94 (2H, d, J=9 Hz), 7.18 (2H, d, J=9 Hz), 6.50 (1H, s), 6.40 (1H, s), 6.20 (2H, s), 5.79 (1H, s), 5.78 (1H, s), 4.77 (1H, s), 4.34 (1H, d, J=15.5 Hz), 4.30 (1H, d, J=15.5 Hz), 3.68 (2H, m), 3.59 (6H, s), 3.58 (3H, s), 2.96 (2H, t, J=7.2 Hz); (+)-HRFABMS m/z 547.1703 [M+H]⁺ (calcd for $C_{29}H_{26}N_2O_9$, 547.1716).

Benzo[1,3]dioxol-5-yl-(3-imidazol-1-yl-propyl)-1,2-diamine (28a). Purification: sgc chromatography (1:1 CH₂Cl₂-hexanes), light tan oil, 0.12 g (12%); ¹H NMR (CDCl₃, 300 MHz) δ 7.36 (1H, s), 6.96 (1H, s), 6.81 (1H, s), 6.53 (1H, d, J=8.1 Hz), 6.10 (1H, d, J=1.8 Hz), 5.94 (1H, dd, J,=8.1 Hz, J₂=1.8 Hz), 5.74 (2H, s), 3.96 (2H, t, J=6.9 Hz), 2.95 (2H, t, J=6.9 Hz), 1.95 (2H, sept., J=7.2 Hz); (+)-HRAPCIMS m/z 246.1240 [M+H]⁺ (calcd for $C_{13}H_{15}N_3O_2$, 246.1243).

6,7-Methylenedioxy-4-(3-imidazol-1-yl-propyl)-9-(3,4,5-trimethoxyphenyl)-4,9-dihydro-3H-furo[3,4-b]quinolin-1-one (28). Purification: sgc chromatography (3:1 EtOAc/CH₃OH) as yellow glass, 0.043 g (10%). Recrystallized from hot EtOAc: mp 206° C. (dec); ¹H NMR (CDCl₃, 300 MHz) δ 7.56 (1H, bs), 7.15 (1H, bs), 6.92 (1H, bs), 6.54 (1H, s), 6.35 (2H, s), 6.34 (1H, s), 5.94 (1H, s), 5.93 (1H, s), 4.93 (1H, s), 4.55 (2H, s), 4.04 (2H, t, J=7.2 Hz), 3.76 (3H, s), 3.74 (6H, s), 3.46 (2H, m), 2.19 (2H, m); (+)-HRAPCIMS m/z 506.1937 [M+H]⁺ (calcd for $C_{27}H_{27}N_3O_7$, 506.1927).

Benzo[1,3]dioxol-5-yl-(furan-2-ylmethyl)-1,2-diamine (32a). Purification: sgc chromatography (7:1 hexanes-EtOAc→5:1 hexanes-EtOAc), tan oil, 0.22 g (24%); ¹H NMR (CDCl₃, 300 MHz) δ 7.37 (1H, bs), 6.67 (1H, dd, J₁=8.4 Hz, J₂=1.8 Hz), 6.34 (1H, d, J=0.9 Hz), 6.32 (1H, d, J=2.4 Hz), 6.23 (1H, d, J=0.9 Hz), 6.13 (1H, dd, J₁=8.1 Hz, J₂=2.18 Hz), 5.86 (1H, s), 5.85 (1H, s), 3.96, 4.26 (2H, s); (+)-HRAPCIMS m/z 218.0817 [M+H]⁺ (calcd for $C_{12}H_{11}NO_3$, 218.0817).

6,7-Methylenedioxy-9-(4-hydroxy-3,5-dimethoxy-phenyl)-4,9-dihydro-3H-furo[3,4-b]quinolin-1-one (29). A stirred solution of ethanol (35 mL), syringaldehyde (0.51 g, 0.0027 mol), and tetronic acid (270 mg, 0.0027 mol) and 3,4 methylenedioxy aniline (380 mg, 0.0027 mol) were heated at reflux for 45 min. The product crystallized from the solution upon cooling. After collection and recrystallization from hot CH₃OH-acetone (~1 L) was performed, the product was again quickly recovered from cooling to provide a light tan powder (87%, 0.90 g): mp 275° C. (dec); ¹H NMR (DMSO-d₆, 300 MHz) δ 9.67 (1H, s), 8.02 (1H, bs), 6.53 (1H, s), 6.40 (1H, s), 6.32 (2H, s), 5.83 (1H, s), 5.78 (1H, s), 4.85 (1H, d, J=15.3 Hz), 4.70 (1H, d, J=15.3 Hz), 4.68 (1H, s), 3.57 (6H, s); ¹³C NMR (DMSO-d₆, 100 MHz) δ 172.14, 158.21, 147.86, 146.32, 143.15, 137.41, 134.27, 130.23, 117.02, 109.55, 105.18, 101.10, 97.20, 94.36, 64.85, 56.03; (+)-HRFABMS m/z 384.0888 [M+H]⁺ (calcd for $C_{20}H_{17}NO_7$, 384.1083).

TBDMS Protected Syringaldehyde. To a stirred solution of CH₂Cl₂ (75 mL), syringaldehyde (2.65 g, 0.0143 mol), imidazole (4.43 g, 0.06 mol), and TBDMS-Cl (6.59 g, 0.044 mol) in CH₂Cl₂ (20 mL) were added slowly, and the solution turned cloudy over 16 h. The CH₂Cl₂ phase was washed with water, dried, and the solvent was removed in vacuo to afford a light oil. The oil was separated by sgc chromatography (2:1 EtOAc-hexanes) yielding a colorless amorphous solid upon standing at rt (93%, 3.95 g): mp 70-72° C.; $^1$H NMR (CDCl$_3$, 300 MHz) δ 9.74 (1H, s), 7.00 (2H, s), 3.77 (6H, s), 0.915 (9H, s), 0.062 (6H, s), consistent with the literature.[27]

6,7-Methylenedioxy-4-(cyclopentyl)-9-(4-hydroxy-3,5-dimethoxy-phenyl)-4,9-dihydro-3H-furo[3,4-b]quinolin-1-one (30) and 4'-TBDMS protected 30. This was prepared from a stirred solution of ethanol (15 mL), and amine 18a (0.31 g, 0.0015 mol) was reacted with tetronic acid (163 mg, 0.001 mol), and TBDMS-protected syringaldehyde (0.44 mg, 0.0015 mol). The product was isolated using sgc chromatography (1:10 EtOAc-CH$_2$Cl$_2$) to yield TBDMS protected 30 as a colorless amorphous powder 0.22 g (25%): $^1$H NMR (CDCl$_3$, 300 MHz) δ 6.63 (1H, s), 6.57 (1H, s), 6.33 (2H, s), 5.93 (1H, s), 5.92 (1H, s), 4.93 (1H, d, J=14.7 Hz), 4.85 (1H, s), 4.74 (1H, d, J=14.7 Hz), 4.16 (1H, sept., J=8.7 Hz), 3.69 (6H, s), 2.00 (6H, m), 1.74 (2H, m), 0.97 (9H, s), 0.08 (6H, s). Cleavage of the silyl protecting group was achieved using a stirred solution of THF (20 mL), 4'-TBDMS protected 30 (0.22 g, 0.00038 mol), and TBAF (0.5 mL added dropwise) with the solution stirred under Ar for 35 min. TLC showed no starting material, and so the reaction mixture was diluted with H$_2$O (3×15 mL) and extracted with CH$_2$Cl$_2$ (3×15 mL). The organic phase was dried and the solvent was removed in vacuo. By means of sgc chromatography (10:1 CH$_2$Cl$_2$-EtOAc→5:1 CH$_2$Cl$_2$-EtOAc) separation, the product 30 was isolated as light yellow crystals, 0.127 g (74%). Recrystallized from CH$_2$Cl$_2$—CH$_3$OH: mp 221-223° C.; $^1$H NMR (CDCl$_3$, 300 MHz) δ 6.55 (1H, s), 6.48 (1H, s), 6.29 (2H, s), 5.85 (1H, s), 5.83 (1H, s), 5.33 (1H, bs), 4.83 (1H, d, J=15.3 Hz), 4.77 (1H, s), 4.65 (1H, d, J=15.3 Hz), 4.07 (1H, p, J=9 Hz), 3.70 (6H, s), 1.91 (6H, m), 1.67 (2H, m); $^{13}$C NMR (CDCl$_3$, 125 MHz) δ 172.65, 158.46, 146.94, 146.76, 143.91, 137.14, 133.50, 131.75, 120.16, 110.67, 104.24, 101.56, 99.86, 97.51, 65.88, 60.41, 56.22, 40.49, 28.59, 28.27, 24.84, 24.86; (+)-HRFABMS m/z 452.1698 [M+H]$^+$ (calcd for C$_{25}$H$_{25}$NO$_7$, 452.1709); anal. C, 63.87; H, 6.06; N, 2.84%, calcd for C$_{25}$H$_{25}$NO$_7$+H$_2$O, C, 63.96; H, 5.80; N, 2.98%.

6,7-Methylenedioxy-4-[2-(4-fluorophenyl)-ethyl]-9-(4-hydroxy-3,5-dimethoxy-phenyl)-4,9-dihydro-3H-furo[3,4-b]quinolin-1-one (31) and 4'-TBDMS Protected 31. The preceding reaction sequence was repeated with ethanol (15 mL), amine 25a (0.220 g, 0.00085 mol), tetronic acid (91 mg, 0.00085 mol), and TBDMS-protected syringaldehyde (0.31 mg, 0.00085 mol). In this case, the solution was heated at reflux for 2 h. Upon cooling, the product crystallized from solution and was recrystallized from hot CH$_3$OH yielding colorless crystals of 4'-TBDMS protected 31 (0.165 g, 30%). $^1$H NMR (CDCl$_3$, 300 MHz) δ 7.10 (2H, m), 6.96 (2H, m), 6.65 (1H, s), 6.60 (1H, s), 6.38 (2H, s), 5.97 (2H, s), 4.97 (1H, s), 4.37 (1H, d, J=14.7 Hz), 4.23 (1H, d, J=14.7 Hz), 3.73 (6H, s,), 3.60 (2H, m,), 2.99 (2H, t, J=6.6 Hz), 0.99 (9H, s), 0.01 (6H, s). Cleavage of the silyl protecting group was again conducted with anhydrous THF (15 mL), TBDMS-protected 31 (0.16 g, 0.00027 mol), and TBAF (0.5 mL). After stirring under Ar for 0.5 h, TLC showed no starting material. The product was isolated as per 30 (above) followed by sgc chromatography (30:1 CH$_2$Cl$_2$-EtOAc→10:1 CH$_2$Cl$_2$-EtOAc→3:2 CH$_2$Cl$_2$-EtOAc) and obtained as an off white powder 0.101 g (75%). Recrystallized from hot CH$_3$OH: mp 198-199° C. (dec); $^1$H NMR (CDCl$_3$, 300 MHz) δ 7.12 (2H, m), 6.96 (2H, m), 6.67 (1H, s), 6.60 (1H, s), 6.44 (2H, s), 5.98 (1H, s), 5.97 (1H, s), 4.99 (1H, s), 4.37 (1H, d, J=15 Hz), 4.29 (1H, d, J=15 Hz), 3.83 (6H, s), 3.70 (2H, m), 3.00 (2H, t, J=6.6 Hz); $^{13}$C NMR (CDCl$_3$, 100 MHz) δ 173.78, 158.42, 147.32, 147.17, 143.97, 136.73, 133.63, 133.13, 130.44, 130.09, 130.00118.70, 115.31, 115.10, 110.39, 105.01, 101.27, 96.05, 94.96, 65.06, 55.67, 39.85, 32.52, 29.93; (+)-HRAPCIMS m/z 506.1613 [M+H]$^+$ (calcd for C$_{28}$H$_{24}$NO$_7$F, 506.1615).

6,7-Methylenedioxy-4-(furan-2-ylmethyl)-9-(4-hydroxy-3,5-dimethoxy-phenyl)-4,9-dihydro-3H-furo[3,4-b]quinolin-1-one (32) and 4'-TBDMS-Protected 32: The preceding reaction sequence was repeated with ethanol (15 mL), 32a (0.17 g, 0.00078 mol), tetronic acid (100 mg, 0.00078 mol), and TBDMS-protected syringaldehyde (0.28 mg, 0.00078 mol). The solution was heated at reflux for 1.5 h, and the solvent was removed in vacuo to afford a yellow solid. The solid was separated by sgc chromatography (30:1 CH$_2$Cl$_2$-EtOAc→400:15 CH$_2$Cl$_2$-EtOAc) and the resulting yellow powder recrystallized from hot hexanes-EtOAc yielding 4'-TBDMS protected 32 as an off-white powder (0.19 g, 43%): $^1$H NMR (CDCl$_3$, 300 MHz,) δ 7.37 (1H, d, J=1.5 Hz), 6.67 (1H, s), 6.54 (1H, s), 6.25 (1H, s), 6.24 (2H, s), 6.23 (1H, s), 5.84 (1H, s), 5.83 (1H, s), 4.97 (1H, s), 4.95 (1H, s), 4.92 (1H, s), 4.76 (1H, d, J=15.1 Hz), 4.63 (1H, d, J=15.1 Hz), 3.68 (6H, s), 0.89 (9H, s), 0.01 (6H, s); $^{13}$C NMR (CDCl$_3$, 100 MHz) δ 174.64, 159.23, 151.90, 149.08, 147.89, 144.90, 143.44, 139.43, 133.35, 131.69, 119.75, 111.11, 110.94, 109.49, 105.50, 102.10, 98.46, 96.18, 66.25, 55.94, 43.46, 41.04, 26.01, 19.00, 0.00; (+)-HRAPCIMS m/z 578.2212 [M+H]$^+$ (calcd for C$_{31}$H$_{35}$NO$_8$Si, 578.2210); anal. C, 64.30; H, 6.48; N, 2.55%, calcd for C$_{31}$H$_{35}$NO$_8$Si, C, 64.45; H, 6.11; N, 2.42%. Cleavage of the silyl protecting group was again conducted with anhydrous THF (15 mL), TBDMS-protected 32 (0.19 g, 0.00033 mol), and TBAF (1.0 mL). After 0.5 h under Ar, TLC showed no starting material. The product was isolated as per 31 followed by sgc chromatography (2:1 CH$_2$Cl$_2$-EtOAc) and was recovered as a colorless powder, 0.132 g (85%). Recrystallized from hot CH$_3$OH-hexanes: mp 223-225° C.; $^1$H NMR (CDCl$_3$, 300 MHz) δ 7.37 (1H, d, J=1.5 Hz), 6.68 (1H, s), 6.53 (1H, s), 6.28 (2H, s), 6.35 (1H, s), 6.34 (1H, s), 5.91 (1H, d, J=1.8 Hz), 5.90 (1H, d, J=1.8 Hz), 4.97 (1H, s), 4.96 (1H, s), 4.94 (1H, s), 4.74 (1H, d, J=15.3 Hz), 4.68 (1H, d, J=15.3 Hz), 3.78 (6H, s); $^{13}$C NMR (CDCl$_3$, 100 MHz) δ 173.78, 158.37, 148.20, 147.13, 146.94, 143.97, 142.47, 136.78, 133.37, 130.66, 118.85, 109.91, 109.88, 108.53, 104.38, 101.14, 97.41, 95.26, 65.33, 55.39, 42.45, 40.01; (+)-HRAPCIMS m/z 464.1351 [M+H]$^+$ (calcd for C$_{25}$H$_{27}$NO$_8$, 464.1345); anal. C, 64.51; H, 4.97; N, 3.04%, calcd for C$_{25}$H$_{211\setminus108}$, C, 64.79; H, 4.57; N, 3.06%.

General Procedure for the Synthesis of 4-Aza-podophyllotoxin Structural Modifications: B and E ring Substitutions 15,[25] 15a-d, 15e-f[2]. The general synthetic procedure now follows for compounds 15 and 15a-15f: A stirred solution of ethanol, substituted aniline (I or II, 1 equiv.), tetronic acid (1 equiv.), and benzaldehyde (III-VII, 1 equiv.) was heated at reflux and monitored by TLC. The formation of the product was usually evident (after 10 to 60 min) by the appearance of a bright blue spot when viewed under UV. The solvent was then removed in vacuo and the product was either recrystallized from, or purified using sgc chromatography, with appropriate solvent systems.

6,7,8-Trimethoxy-9-(3,4,5-trimethoxyphenyl)-4,9-dihydro-3H-furo[3,4-b]quinolin-1-one (15). Purification: recrystallized from CH$_3$OH as colorless amorphous crystals, 0.535 g (45%); mp 137-139° C.; 1H NMR (CDCl$_3$, 300 MHz) δ 8.29 (1H, s), 6.47 (2H, s), 6.29 (1H, s), 5.16 (1H, s), 4.69 (1H, d, J=16 Hz), 4.61 (1H, d, J=16 Hz), 3.82 (3H, s), 3.78 (3H, s), 3.76 (3H, s), 3.74 (6H, s), 3.48 (3H, s); (+)-HRFABMS m/z 444.1659 [M+H]$^+$ (calcd for C$_{23}$H$_{25}$NO$_8$, 444.1658).

6,7,8-Trimethoxy-9-(3-bromo-4,5-trimethoxyphenyl)-4,9-dihydro-3H-furo[3,4-b]quinolin-1-one (15a). Purification: sgc chromatography (4:2:1 hexanes-EtOAc-CH$_3$OH) obtained as colorless crystals, 0.584 g (50%). Recrystallized from acetone-CH$_3$OH: mp 175-177° C.; $^1$H NMR (CDCl$_3$, 500 MHz) δ 8.41 (1H, s), 6.93 (1H, s), 6.81 (1H, s), 5.16 (1H, s), 4.75 (1H, d, J=15.8 Hz), 4.66 (1H, d, J=15.8 Hz), 3.88 (3H, s), 3.85 (3H, s), 3.81 (3H, s), 3.80 (3H, s), 3.53 (3H, s); $^{13}$C NMR (CDCl$_3$, 125 MHz) δ 173.90, 157.69, 153.59, 152.38, 144.69, 143.66, 138.65, 132.66, 123.72, 117.29, 111.96, 109.83, 97.26, 95.70, 65.67, 60.88, 60.59, 60.40, 56.16, 56.05, 35.48; (+)-HRAPCIMS m/z 494.0628 [M+H]$^+$ (calcd for C$_{22}$H$_{22}$NO$_7$$^{81}$Br, 494.0637); anal. C, 53.22; H, 4.74; N, 2.86%, calcd for C$_{22}$H$_{22}$NO$_7$$^{81}$Br, C, 53.67; H, 4.50; N, 2.85%.

3-(TBDMS-O)-4-methoxybenzaldehyde. A stirred solution of CH$_2$Cl$_2$ (30 mL), TBDMSCl (1.38 g, 0.008 mol), and imidazole (0.61 g, 0.008 mol) was stirred for 5 min. The solution turned cloudy and 3-hydroxy-4-methoxybenzaldehyde was added slowly. The reaction proceeded under Ar for 3 h and was terminated with H$_2$O (30 mL). The CH$_2$Cl$_2$ layer was dried, the solvent was removed in vacuo, and sgc chromatography (4:1 hexanes-EtOAc) was used to isolate the product, 3-(TBDMS-O)-4-methoxybenzaldehyde[24,25] as a light yellow oil, 1.76 g, (83%); $^1$H NMR (CDCl$_3$, 300 MHz) δ 9.68 (1H, s); 7.31 (1H, dd, J$_1$=8.4 Hz, J$_2$=2.4 Hz), 7.25 (1H, d, J=2.4 Hz), 6.80 (1H, d, J=8.4 Hz), 3.73 (3H, s), 0.89 (9H, s), 0.05 (6H, s).

6,7,8-Trimethoxy-9-(3-OTBDMS-4-methoxyphenyl)-4,9-dihydro-3H-furo[3,4-b]quinolin-1-one (15b). A stirred solution of 3-(TBDMS-O)-4-methoxybenzaldehyde (1.99 g, 0.0075 mol) and ethanol (30 mL) was heated to reflux. Next, 3,4,5-trimethoxyaniline (1.39 g, 0.0075 mol), and tetronic acid (0.76 g, 0.0075 mol) were added and heating at reflux continued for 1.5 h. TLC showed that a bright blue UV absorbing spot formed, and the product (15b) was isolated with sgc chromatography (6:1 CH$_2$Cl$_2$/EtOAc) as a yellow oil that solidified at room temperature to yield 6,7,8-trimethoxy-9-(3-OTBDMS-4-methoxyphenyl)-4,9-dihydro-3H-furo[3,4-b]quinolin-1-one (15b) as an amorphous light yellow solid, 2.23 g (58%). Recrystallized from EtOAc-hexanes: mp 169-171° C.; $^1$H NMR (CDCl$_3$, 300 MHz) δ 7.81 (1H, s), 6.63 (3H, m), 6.16 (1H, s), 4.98 (1H, s), 4.54 (1H, s), 4.53 (1H, s), 3.73 (3H, s), 3.65 (3H, s), 3.60 (3H, s), 3.31 (3H, s), 0.82 (9H, s), 0.00 (6H, s); $^{13}$C NMR (DMSO-d$_6$, 125 MHz) δ176.71, 162.10, 157.55, 156.44, 153.53, 148.43, 144.48, 142.40, 137.89, 125.24, 124.78, 116.87, 115.06, 100.91, 100.32, 69.59, 65.08, 64.70, 60.57, 60.25, 39.17, 30.34, 22.88, 0.07; (+)-HRAPCIMS m/z 514.2280 [M+H]$^+$ (calcd for C$_{27}$H$_{36}$NO$_7$Si, 514.2261); anal. C, 62.99; H, 6.79; N, 2.99%, calcd for C$_{27}$H$_{36}$NO$_7$Si, C, 63.13; H, 6.87; N, 2.73%.

6,7,8-Trimethoxy-9-(3-hydroxy-4-methoxyphenyl)-4,9-dihydro-3H-furo[3,4-b]quinolin-1-one (15c). TBAF (1 M solution in THF, 3.3 mL) was added slowly to a stirred solution of silyl ether 15b (1.55 g, 0.0030 mol) in THF (50 mL), and the reaction was allowed to proceed for 1 h, at which point TLC showed no starting material present. The reaction was terminated with H$_2$O (30 mL) and the aqueous portion was extracted with CH$_2$Cl$_2$ (3×30 mL). The combined organic extractions were partitioned with 2 N KOH (3×30 mL). The base extracts were combined, brought to pH 7 with 1 N HCl, and this solution was extracted with EtOAc (3×35 mL). The organic extracts were combined, dried, and the solvent removed in vacuo leaving a yellowish white solid that was recrystalized from hot EtOAc to yield colorless crystals 0.95 g (79%). Recrystallized from EtOAc: mp 297-299° C.; $^1$H NMR (CDCl$_3$, 300 MHz) δ 8.54 (1H, s), 6.68 (1H, d, J=8.4 Hz), 6.64 (2H, s), 6.55 (1H, d, J=8.1 Hz), 6.19 (1H, s), 5.69 (1H, bs), 4.97 (1H, s), 4.45 (2H, s), 3.71 (3H, s), 3.65 (3H, s), 3.61 (3H, s), 3.34 (3H, s); $^{13}$C NMR (DMSO-d$_6$, 125 MHz) δ 172.46, 157.91, 153.09, 152.18, 146.46, 146.35, 140.37, 137.99, 133.60, 118.54, 115.55, 112.27, 110.94, 96.64, 96.02, 65.28, 60.80, 60.45, 56.17, 56.09, 35.05; (+)-HRAPCIMS m/z 400.1424 [M+H]$^+$ (calcd for C$_{21}$H$_{22}$NO$_7$, 400.1396).

6,7-Methylenedioxy-9-(2,3-methylenedioxyphenyl)-4,9-dihydro-3H-furo[3,4-b]quinolin-1-one (15d). Purification: recrystallized from acetone-CH$_3$OH as a light brown powder, 0.55 g (62%); mp 324-327° C.; $^1$H NMR (DMSO-d$_6$, 300 MHz) δ 9.75 (1H, s), 6.30 (1H, d, J=1.2 Hz), 6.50 (1H, d, J=4.5 Hz), 6.46 (1H, s), 6.38 (1H, s, 1H), 5.90 (2H, d, J=18.6 Hz), 5.80 (2H, d, J=18 Hz), 4.95 (1H, s), 4.83 (1H, d, J=15.9 Hz), 4.73 (1H, d, J=15.9 Hz); $^{13}$C NMR (DMSO-d$_6$, 125 MHz) δ 181.39, 168.52, 156.39, 156.12, 153.42, 152.87, 139.85, 137.47, 125.46, 118.47, 118.39, 116.12, 110.71, 110.15, 106.91, 106.82, 101.92, 74.47, 43.24; (+)-HRFABMS m/z 352.0843 [M+H]$^+$ (calcd for C$_{19}$H$_{14}$NO$_6$, 352.0821); anal. C, 65.05; H, 4.08; 3.99%, calcd for C$_{19}$H$_{14}$NO$_6$, C, 64.96; H, 3.73; N, 3.99%.

6,7-Methylenedioxy-9-(3,4,5-trimethoxyphenyl)-4,9-dihydro-3H-furo[3,4-b]quinolin-1-one (15e).[25] Purification: recrystallized from acetone-CH$_3$OH as a colorless powder, 8.32 g (72%). mp 273-275° C.; $^1$H NMR (DMSO-d$_6$, 300 MHz) δ 9.82 (1H, s), 6.65 (1H, s), 6.51 (1H, s), 6.47 (2H, s), 5.84 (1H, s), 5.79 (1H, s), 4.85 (1H, d, J=15.9 Hz), 4.75 (1H, s), 4.74 (1H, d, J=15.9 Hz), 3.59 (6H, s), 3.49 (3H, s), consistent with literature data.[24,25]

6,7-Dimethoxy-9-(3,4,5-trimethoxyphenyl)-3H-furo[3,4-b]quinolin-1-one (15f)[25] A stirred mixture of toluene, olefin 15e (2.0 g) and 10% Pd/C (1.0 g) was heated at reflux as air was bubbled through the solution. After oxidation for 72 h, the catalyst was collected and the solvent was removed in vacuo leaving a white solid, which recrystallized from EtOAc-CH$_3$OH as a colorless amorphous solid, 1.76 g (88%); mp dec 150° C.; $^1$H NMR (DMSO-d$_6$, 400 MHz) δ 7.50 (1H, s), 7.04 (1H, s), 6.70 (2H, s), 6.26 (2H, s), 5.39 (2H, s), 3.76 (3H, s), 3.74 (6H, s). $^{13}$C NMR (DMSO-d6, 100 MHz) δ 168.35, 163.38, 153.59, 153.14, 150.50, 149.14, 148.25, 138.28, 128.13, 123.91, 112.47, 107.69, 105.43, 103.59, 102.22, 69.42, 60.62, 56.56; (+)-HRAPCIMS m/z 396.1016 [M+H]$^+$ (calcd for C$_{21}$H$_{17}$NO$_7$, 396.1083).

6,7-Methylenedioxy-4-methyl-9-(3,4,5-trimethoxyphenyl)-4,9-dihydro-3H-furo[3,4-b]quinolin-1-one (16). To a stirred solution of anhydrous THF (10 mL) and secondary amine 15e (0.30 g, 0.0008 mol) was added BuLi (0.4 mL, 0.0008 mol, 2 M in THF). The solution turned deep red in color and iodomethane (0.05 mL, 0.0008 mol) was added dropwise. After 1.5 h under Ar, the reaction was terminated by slowly adding H$_2$O (20 mL). The aqueous phase was partitioned with CH$_2$Cl$_2$ (3×30 mL). The combined organic extract was dried and the solvent removed in vacuo. The N-methyl derivative 16 was obtained by sgc (4:1 CH$_2$Cl$_2$/EtOAc) and recrystallized from hot EtOAc as a light yellow solid, 0.162 g (53%): mp 224-226° C., [lit.[24] mp 226° C.]; $^1$HNMR (CDCl$_3$, 300 MHz) δ 6.58 (1H, s), 6.57 (1H, s), 6.40 (2H, s), 5.95 (2H, d, J=1.5 Hz), 5.00 (1H, s), 4.86 (1H, d, J=15.9 Hz), 4.81 (1H, d, J=15.9 Hz), 3.79 (3H, s), 3.78 (6H, s); $^{13}$C NMR (CDCl$_3$, 125 MHz) δ 172.65, 158.01, 153.16, 147.52, 144.16, 141.51, 136.82, 133.08, 118.26, 110.68, 105.23, 101.62, 97.42, 94.96, 65.00, 60.73, 56.17, 56.08, 40.67, 33.61; (+)-HRAPCIMS m/z 412.1399 [M+H]$^+$ (calcd for $C_{22}H_{21}NO_7$, 412.1396), consistent with literature data.[24]

Cancer Cell Line Procedures. The human cancer cell growth inhibition data were determined using the standard sulforhodamine B assay of the US National Cancer Institute as previously described.[35] In short, cells in a 5% fetal bovine serum/RPMI1640 medium were inoculated in 96-well plates and incubated for 24 h. Next, serial dilutions of the samples were added. After 48 h, the plates were fixed with trichloroacetic acid, stained with sulforhodamine B, and read with an automated microplate reader. A growth inhibition of 50% ($GI_{50}$ or the drug concentration causing a 50% reduction in the net protein increase) was determined from optical density data employing Immunosoft® software. Table 2 shows the Murine P388 Lymphocytic Leukemia Inhibitory Activity (ED50 μg/mL) and Growth Inhibition of Human Cancer Cell Lines (GI50 μg/mL) for compounds of the disclosure.

TABLE 2

| | cell line[a] | | | | | | |
|---|---|---|---|---|---|---|---|
| compound | P388 | BXPC-3 | MCF-7 | SF-268 | NCI-H460 | KM20L2 | DU-145 |
| 13 | 2.0 | 0.60 | 0.37 | 0.41 | 0.58 | 0.52 | 1.3 |
| 14 | 0.28 | 0.48 | 0.34 | 0.36 | 0.33 | 0.38 | 0.49 |
| 15 | 1.3 | 5.6 | 1.7 | 3.6 | 3.6 | ND[b] | 3.3 |
| 15a | 0.11 | 0.56 | 0.12 | 0.11 | 0.35 | ND[b] | 0.42 |
| 15c | 0.78 | 6.5 | 7.0 | 7.3 | 10.1 | ND[b] | >10 |
| 15d | 0.17 | 0.065 | 0.0039 | 0.0089 | 0.021 | ND[b] | 0.041 |
| 15e[c] | 0.0018 | ND[b] | ND[b] | ND[b] | ND[b] | ND[b] | ND[b] |
| 15f | 3.6 | 4.1 | 3.4 | 2.4 | 2.8 | 2.1 | 2.4 |
| 16 | 0.027 | 0.049 | 0.034 | 0.029 | 0.032 | 0.032 | 0.026 |
| 17 | 0.24 | 0.040 | 0.026 | 0.026 | 0.028 | 0.032 | 0.047 |
| 18 | 15.3 | 0.083 | 0.045 | 0.062 | 0.16 | 0.12 | 0.27 |
| 19 | 3.4 | 0.17 | 0.052 | 0.066 | 0.27 | 0.24 | 0.27 |
| 20 | 0.18 | 0.43 | 0.29 | 0.46 | 1.0 | 0.51 | 2.5 |
| 21 | 1.7 | 4.4 | >10 | >10 | >10 | >10 | >10 |
| 22 | 2.6 | 3.5 | 0.89 | 2.6 | 3.0 | 2.5 | 2.0 |
| 23 | 1.9 | 0.046 | 0.037 | 0.030 | 0.031 | 0.033 | 0.047 |
| 24 | 2.5 | 0.38 | 0.32 | 0.33 | 0.34 | 0.29 | 0.42 |
| 25 | 3.3 | 0.90 | 0.42 | 0.52 | 2.3 | 2.4 | 2.5 |
| 26 | 2.6 | 0.54 | 0.34 | 0.35 | 0.30 | 0.37 | 0.31 |
| 27 | 34.8 | 0.39 | 0.080 | 0.20 | 0.30 | 0.26 | 0.30 |
| 28 | 2.0 | 2.9 | 0.64 | 2.5 | 3.0 | 2.2 | 2.1 |
| 29 | 0.028 | 0.028 | 0.025 | 0.026 | 0.027 | 0.032 | 0.033 |
| 30 | 30.3 | 0.53 | 0.32 | 0.39 | 0.33 | 2.1 | 0.41 |
| 31 | 0.21 | 1.4 | 0.34 | 0.48 | 0.36 | ND[b] | 0.38 |
| 32 | 0.89 | 1.0 | 0.054 | 0.061 | 0.24 | ND[b] | 0.39 |

[a]Cancer cell lines in order: murine lymphocytic leukemia (P388); pancreas (BXPC-3); breast (MCF-7); CNS (SF-268); lung (NCI-H460); colon (KM20L2) and prostate (DU-145).
[b]ND = not determined see Ref. [35].
[c]See Ref [25].

From the results recorded in Table 2, some structure/activity trends are evident. Podophyllotoxin derivatives with alkyl groups in the 4-position revealed the most potent cancer cell growth inhibitory activity (see substances 16[24] and 17-19) and were found selective for several cell lines, especially breast and CNS. Short linkages between the aza-podophyllotoxin core and aromatic substituents seem to be ideal, as evident in the order of magnitude increase in cytostatic activity of 23 over 25. Several 4'-demethylated compounds were also synthesized. Although activity remained good overall, it decreased with the removal of the 4'-methyl group in 18 vs. 30 in contrast compounds 25 vs. 31 have nearly identical activities in most of the tested cell lines with compound 31 appearing slightly more potent in a few cases.

REFERENCES

The following references are hereby incorporated by reference in their entireties:

REFERENCES (1) For Antineoplastic Agents. 584, see Pettit, G. R.; Ye, Q.; Knight, J. C.; Hogan, F.; Melody, N.; Mukku, V. J. R. V.; Doubek, D. L.; Chapuis, J.-C., in preparation.
(2) Iwu, M. M.; Court, W. E. *Planta Med.* 1980, 38, 260-263.
(3) Addae-Mensah, I.; Achenbach, H. *Phytochemistry* 1985, 24, 1817-1819.
(4) Cimanga, K.; Ying, L.; De Bruyne, T.; Apers, S.; Cos, P.; Hermans, N.; Bakana, P.; Tona, L.; Kambu, K.; Kalenda, D. T.; Pieters, L.; Vanden Berghe, D.; Vlietinck, A. J. *J. Pharm. Pharmacol.* 2001, 53, 757-761.
(5) Addae-Mensah, I.; Munenge, R. W. *Fitoterapia* 1989, 60, 359-362.
(6) Rashid, M. A.; Gustafson, K. R.; Cardellina, J. H., II; Boyd, M. R. *Nat. Prod. Lett.* 2000, 14, 285-292.
(7) Chang, L. C.; Song, L. L.; Park, E. J.; Luyengi, L.; Lee, K. J.; Farnsworth, N. R.; Pezzuto, J. M.; Kinghorn, A. D. *J. Nat. Prod.* 2000, 63, 1235-1238.
(8) Ikeda, R.; Nagao, T.; Okabe, H.; Nakano, Y.; Matsunaga, H.; Katano, M.; Mori, M. *Chem. Pharm. Bull.* 1998, 46, 871-874.
(9) Broomhead, A. J.; Dewick, P. M. *Phytochemistry* 1990, 29, 3831-3837.
(10) Dossena, A.; Marchelli, R.; Pochini, A. *J. Chem. Soc., Chem. Commun.* 1974, 771-772.
(11) Marchelli, R.; Dossena, A.; Pochini, A.; Dradi, E. *J. Chem. Soc., Perkin Trans.* 1 1977, 713-717.
(12) Pettit, G. R. *J. Nat. Prod.* 1995, 58, 359-364.
(13) Hartwell, J. L.; Schrecker, A. W. In *Fortschritte der Chemie organischer Naturstoffe*, Vol. XV; Zechmeister, L., Ed.; Springer-Verlag: Vienna, 1958; p 83.

(14) Hearon, W. M.; MacGregor, W. S. *Chem. Rev.* 1955, 55, 957-1068.
(15) (a) Mider, G. B. *J. Nat. Cancer Inst.* 1957, 19, 191-223. (b) Seliger, H. *Der Krebsarzt* 1955, 10, 357-360.
(16) Eyberger, A. L.; Dondapati, R.; Porter, J. R. *J. Nat. Prod.* 2006, 69, 1121-1124.
(17) Wolff, S. N.; Hainsworth, J. D.; Greco, F. A. *J. Clin. Oncol.* 2008, 26, 5310-5312.
(18) Zhang, Y.-J.; Litaudon, M.; Bousserouel, H.; Martin, M.-T.; Thoison, O.; Léonce, S.; Dumontet, V.; Sévenet, T.; Guéritte, F. *J. Nat. Prod.* 2007, 70, 1368-1370.
(19) (a) Wu, Y.; Zhao, J.; Chen, J.; Pan, C.; Li, L.; Zhang, H. *Org. Lett.* 2009, 11, 597-600. (b) Wu, Y.; Zhang, H.; Zhao, Y.; Zhao, J.; Chen, J.; Li, L. *Org. Lett.* 2007, 9, 1199-1202.
(20) (a) Zhang, Z.-J.; Tian, J.; Wang, L.-T.; Wang, M.-J.; Nan, X.; Yang, L.; Liu, Y-Q.; Morris-Natschke, S. L.; Lee, K.-H.; *Biorg. Med. Chem.* 2014, 22, 204-210. (b) Li, W.-Q.; Wang, X.-L.; Qian, K.; Liu, Y.-Q.; Wang, C.-Y.; Yang, L.; Tian. J.; Morris-Natschke, S. L.; Zhou, X.-W.; Lee, K.-H. *Biorg. Med. Chem.* 2013, 21, 2363-2369. (c) Kamal, A.; Mallareddy, A.; Suresh, P.; Nayak, L.; Shetti, R. V. C. R. N. C.; Rao, N. S.; Tamboli, J. R.; Shaik, T. B.; Vishnuvardhan, M. V. P. S.; Ramakrishna, S. *Eur. J. Med. Chem.* 2012, 47, 530-545. (d) Wang, C.; Wu, Z.; Zhao, Y.; Ni, C.; Zhao, X.; Zhu, L. *Arch. Pharm. Chem. Life Sci.* 2011, 344, 735-740. (e) Jin, Y.; Liu, J.; Huang, W.-T.; Chen, S. W.; Hui, L. *Eur. J Med. Chem.* 2011, 46, 4056-4061. (f) Singh, P.; Faridi, U.; Srivastava, S.; Kumar, J. K.; Darokar, M. P.; Luqman, S; Shanker, K.; Chanotiya, C. S.; Gupta, A.; Gupta, M. M.; Negi, A. N. *Chem. Pharm. Bull.* 2010, 58, 242-246. (g) Castro, A. M.; del Corral, J. M. M.; Garcia, P. A.; Rojo, M. V.; de la Iglesia-Vicente, J.; Mollinedo, F.; Cuevas, C.; San Feliciano, A. *J Med. Chem.* 2010, 53, 983-993. (h) Passarella, D.; Peretto, B.; Yepes, R. B.; Cappellettit, G.; Cartelli, D.; Ronchi, C.; Snaith, J.; Fontana, G.; Danieli, B.; Borlak, *J. Eur. J. Med. Chem.* 2010, 45, 219-226. (i) Yong, Y.; Shin, S. Y.; Lee, Y. H.; Lim, Y. *Bioorg. Med. Chem. Lett.* 2009, 19, 4367-4371. (j) Zhi, X.; Yu, X.; Yang, C.; Ding, G.; Chen, H.; Xu, H. *Bioorg. Med. Chem. Lett.,* 2014, 24, 765-722. (k) Che, Z.; Yu, X.; Zhi, X.; Fan, L.; Yao, X.; Xu, H. *J. Agric. Food. Chem.* 2013, 61, 8148-8155. (l) Xu, H.; He, X. Q.; *Bioorg. Med. Chem. Lett.* 2010, 20, 4503-4506. (m) Kamal, A.; Suresh, P.; Ramaiah, M. J.; Mallarddy, A.; Kumar, B. A.; Raju, P.; Gopal, J. V.; Pushpavalli, S. N. C. V. L.; Lavanya, A.; Sarma, P. *Bioorg. Med. Chem.* 2011, 19, 4589-4600. (n) Salerno, S.; Da Settuni, F.; Taliani, S.; Sunirubu, F.; La Motta, C.; Fornaciari, G.; Marini, A. M. *Curr. Med. Chem.* 2010, 17, 4270-4290. (o) Zhang, Z. W.; Zhang, J. Q.; Hui, J.-Q.; Chen, L. H.; Chen, S.-W.; Tian, X. *Eur. J. Med. Chem.* 2010, 45, 1673-1677. (p) Labruere, R.; Hautier, B.; Testud, M.; Seguin, J.; Lenoir, C.; Desbene-Finck, S.; Helissey, P.; Garbay, C.; Chabot, G. G.; Vidal, M.; Giorgi-Renault, S. *ChemMedChem* 2010, 5, 2016-2025.
(21) (a) Pettit, G. R.; Alkalay, D. S. *J. Org. Chem.* 1960, 25, 1363-1365. (b) Pettit, G. R.; Baumann, M. F.; Rangammal, K. N. *J. Med. Pharm. Chem.* 1962, 5, 800-808.
(22) Pinney, K. G.; Jelinek, C.; Edvardsen, K.; Chaplin, D. J.; Pettit, G. R. In *Anticancer Agents from Natural Products*; Cragg, G. M.; Kingston, D. G. I.; Newman, D. J.; Eds.; Taylor and Francis: Boca Raton, Fla., 2005; pp 23-46.
(23) (a) Wilstermann, A. M.; Bender, R. P.; Godfrey, M.; Choi, S.; Anklin, C.; Berkowitz, D. B.; Osheroff, N.; Graves, D. E. Biochemistry 2007, 46, 8217-8225. (b) Dong, W.; Zhang, L.; Niu, Y.; Fan, D.; Wu, X.; Tang, X.; Cai, C. *Expert Opin. Drug. Deliv.* 2013, 10, 559-571.
(24) (a) Tratrat, C.; Georgi-Renault, S.; Husson, H.-P. *Org. Lett.* 2002, 4, 3187-3189. (b) Giorgi-Renault, S. *Ann. Pharm. Fr.* 2005, 63, 63-68.
(25) Hitotsuyanagi, Y.; Fukuyo, M.; Tsuda, K.; Kobayashi, M.; Ozeki, A.; Itokawa, H.; Takeya, K. *Bioorg. Med. Chem. Lett.* 2000, 10, 315-317.
(26) Botes, M. G.; Pelly, S. C.; Blackie, M. A. L.; Kornienko, A.; van Otterlo, W. A. L. *Chem. Heterocycl. Compd.* 2014, 50, 119-137.
(27) Wang, J. Z.; Tian, X.; Tsumura, H.; Shimura, K.; Ito, H. *Anticancer Drug Des.* 1993, 8, 193-202.
(28) Hanauske, A. R.; Wuester, K. C.; Lehmer, A.; Rotter, M.; Schneider, P.; Kaeser-Froelich, A.; Rastetter, J.; Depenbrock, H. *Eur. J. Cancer, Part A* 1995, 31A, 1677-1681.
(29) Utsugi, T.; Shibata, H.; Kumio, S.; Aoyagi, K.; Wierzba, K.; Kobunai, T.; Terada, T.; Oh-hara, T.; Tsuruo, T.; Yamada, Y. *Cancer Res.* 1996, 56, 2809-2814.
(30) Lee, C. C.; Huang, T. S. *Pharm. Res.* 2001, 18, 846-851.
(31) Kumar, A.; Alegria, A. E. *J. Heterocycl. Chem.* 2010, 47, 1275-1282.
(32) Snyder, H. R.; Konecky, M. S.; Lennarz, W. J. *J. Am. Chem. Soc.* 1958, 80, 3611-3615.
(33) Ley, S. V.; Thomas, A. W. *Angew. Chem. Intl. Ed.* 2003, 42, 5400-5449.
(34) Beletskaya, I. P.; Cheprakov, A. V. *Coord. Chem. Rev.* 2004, 248, 2337-2364.
(35) Monks, A.; Scudiero, D.; Skehan, P.; Shoemaker, R.; Paull, K.; Vistica, D.; Hose, C.; Langley, J.; Cronise, P.; Viagro-Wolff, A.; Gray-Goodrich, M.; Campbell, H.; Mayo, J.; Boyd, M. *J. Natl. Cancer Inst.* 1991, 83, 757-766.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed is:
1. A compound selected from the group consisting of:
6,7-Methylenedioxy-4-(cyclobutyl)-9-(3,4,5-trimethoxyphenyl)-4,9-dihydro-3H-furo[3,4-b]quinolin-1-one (Compound 17);
6,7-Methylenedioxy-4-(cyclopentyl)-9-(3,4,5-trimethoxyphenyl)-4,9-dihydro-3H-furo[3,4-b]quinolin-1-one (Compound 18);
6,7-Methylenedioxy-4-(cyclohexyl)-9-(3,4,5-trimethoxyphenyl)-4,9-dihydro-3H-furo[3,4-b]quinolin-1-one (Compound 19);
6,7-Methylenedioxy-4-(2-piperidin-1-yl-ethyl)-9-(3,4,5-trimethoxyphenyl)-4,9-dihydro-3H-furo[3,4-b]quinolin-1-one (Compound 21);
6,7-Methylenedioxy-4-(2-morpholin-4-yl-ethyl)-9-(3,4,5-trimethoxyphenyl)-4,9-dihydro-3H-furo[3,4-b]quinolin-1-one (Compound 22);
6,7-Methylenedioxy-4-(cyclopentyl)-9-(4-hydroxy-3,5-dimethoxy-phenyl)-4,9-dihydro-3H-furo[3,4-b]quinolin-1-one (Compound 30);
and
a pharmaceutically acceptable salt thereof.

2. A pharmaceutical composition comprising a compound of claim 1 or a pharmaceutically acceptable salt thereof and a pharmaceutically acceptable carrier.

3. A method for treating cancer in a patient in need thereof comprising administering to the patient a compound of claim 1, wherein the compound is administered in an amount effective to treat cancer.

4. The compound of claim 1, wherein the compound is selected from the group consisting of:
- 6,7-Methylenedioxy-4-(cyclobutyl)-9-(3,4,5-trimethoxyphenyl)-4,9-dihydro-3H-furo[3,4-b]quinolin-1-one (Compound 17);
- 6,7-Methylenedioxy-4-(cyclopentyl)-9-(3,4,5-trimethoxyphenyl)-4,9-dihydro-3H-furo[3,4-b]quinolin-1-one (Compound 18);
- 6,7-Methylenedioxy-4-(cyclohexyl)-9-(3,4,5-trimethoxyphenyl)-4,9-dihydro-3H-furo[3,4-b]quinolin-1-one (Compound 19);
- 6,7-Methylenedioxy-4-(cyclopentyl)-9-(4-hydroxy-3,5-dimethoxy-phenyl)-4,9-dihydro-3H-furo[3,4-b]quinolin-1-one (Compound 30);

and
a pharmaceutically acceptable salt thereof.

* * * * *